(12) United States Patent
Srivastava et al.

(10) Patent No.: US 10,287,587 B2
(45) Date of Patent: May 14, 2019

(54) PROSTATE CANCER-SPECIFIC ALTERATIONS IN ERG GENE EXPRESSION AND DETECTION AND TREATMENT METHODS BASED ON THOSE ALTERATIONS

(71) Applicant: THE HENRY M. JACKSON FOUNDATION FOR THE ADVANCEMENT OF MILITARY MEDICINE, INC., Bethesda, MD (US)

(72) Inventors: Shiv Srivastava, Potomac, MD (US); Albert Dobi, Rockville, MD (US); Taduru Sreenath, Germantown, MD (US); Gyorgy Petrovics, Bethesda, MD (US); Chen Sun, Bethesda, MD (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 1068 days.

(21) Appl. No.: 13/974,007

(22) Filed: Aug. 22, 2013

(65) Prior Publication Data
US 2015/0044670 A1  Feb. 12, 2015

Related U.S. Application Data

(63) Continuation of application No. 12/444,903, filed as application No. PCT/US2007/080826 on Oct. 9, 2007, now Pat. No. 8,541,169.

(60) Provisional application No. 60/929,505, filed on Jun. 29, 2007, provisional application No. 60/850,254, filed on Oct. 10, 2006.

(51) Int. Cl.
*C12Q 1/68* (2018.01)
*C12N 15/113* (2010.01)
*C12Q 1/6886* (2018.01)

(52) U.S. Cl.
CPC ........ *C12N 15/1135* (2013.01); *C12Q 1/6886* (2013.01); *C12N 2310/11* (2013.01); *C12N 2310/14* (2013.01); *C12N 2320/30* (2013.01); *C12Q 2600/118* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | | |
|---|---|---|---|---|
| 5,830,645 | A | * | 11/1998 | Pinkel .................. C12Q 1/6816 382/128 |
| 6,790,619 | B2 | | 9/2004 | Meissner et al. |
| 2002/0182586 | A1 | | 12/2002 | Morris et al. |
| 2004/0241707 | A1 | | 12/2004 | Gao et al. |
| 2005/0031623 | A1 | | 2/2005 | Pastorek et al. |
| 2005/0202428 | A1 | | 9/2005 | Andrews et al. |
| 2007/0048738 | A1 | | 3/2007 | Donkena et al. |
| 2007/0050146 | A1 | | 3/2007 | Bentwich et al. |
| 2007/0212702 | A1 | | 9/2007 | Tomlins et al. |
| 2008/0038743 | A1 | | 2/2008 | Gocke et al. |
| 2008/0269157 | A1 | | 10/2008 | Srivastava et al. |

FOREIGN PATENT DOCUMENTS

| | | |
|---|---|---|
| WO | 2001/57274 | 8/2001 |
| WO | 2002/010449 | 2/2002 |
| WO | 2003/073826 | 9/2003 |
| WO | 2005/113816 | 12/2005 |

OTHER PUBLICATIONS

Goode et al. (Nested RT-CPR Sensitivity controls are essential to determine the biological significance of detected mRNA From Methods in Molecular Blolgy Vo. 193 edited by J. O'Connell).*
European Patent Office Communication issued in European Application No. 12163605.4 dated Jan. 8, 2013, 19 Pages.
Petrovics, G et al. Frequent overexpression of ETS-related gene-1 (ERG1) in prostate cancer transcriptome. Oncogene, vol. 24, No. 23, May 26, 2005, pp. 3847-3852.
Ueki, A. et al. Intramolecular epitope spreading among anti-caspase-8 autoantibodies in patients with silicosis, systemic sclerosis and systemic lupus erythematosus, as well as in healthy individuals Clinical and Experimental Immunology. 2, vol. 129. No. 3, pp. 556-561.
Oligonucleic SEQ ID No. 34952 for detecting SNP TSC0011099. Feb. 20, 2002, 1 Page, XP002682957.
Wang, J et al. Expression of Variant TMPRSS2/ERG Fusion Messenger RNAs is Associated with Aggressive Prostate Cancer. Cancer Research, vol. 66, No. 17, Sep. 1, 2006, pp. 8347-8351.
Perner, S et al. TMPRSS2:ERG Fusion-Associated Deletions Provide Insight into the Heterogeneity of Prostate Cancer. Cancer Research, vol. 66, No. 17, Sep. 1, 2006, pp. 8337-8341.
Tomlins, S A et al. Recurrent Fusion of TMPRSS2 and ETS Transcription Factor Genes in Prostate Cancer. Science, vol. 310, No. 5748, Oct. 28, 2005, pp. 644-648.
Owczarek, C M et al. Detailed mapping of the ERG-ETS2 interval of human chromosome 21 and comparison with the region of conserved synteny on mouse chromosome. Gene, vol. 324, Jan. 7, 2004, pp. 65-77.

(Continued)

*Primary Examiner* — Katherine D Salmon
(74) *Attorney, Agent, or Firm* — MH2 Technology Law Group, LLP

(57) ABSTRACT

The disclosure describes alterations in ERG gene expression. ERG isoforms and promoter sequence of the ERG gene that are involved in, or associated with, prostate cancer are provided. The disclosure further provides therapeutic compositions and methods of detecting, diagnosing, prognosing, and treating prostate cancer, including biomarkers for detecting the expression of two or more of the following genes: PSA/KLK3, PMEPA1, NKX3.1, ODC1, AMD1, and ERG.

6 Claims, 18 Drawing Sheets
Specification includes a Sequence Listing.

(56) References Cited

OTHER PUBLICATIONS

Shand, R L et al. Molecular biology of prostate-cancer pathogenesis. Current Opinion in Urology, vol. 16, No. 3, May 1, 2006, pp. 123-131.
Sequence 14907 from Patent WO0157274, Jan. 21, 2004, 1 Page, XP002682891.
Hu, Y et al. Delineation of TMPRSS2-ERG Splice Variants in Prostate Cancer. Clinical Cancer Research, vol. 14, No. 15, Aug. 1, 2008, pp. 4719-4725.
Sequence 1 from Patent WO2005113816, Jan. 4, 2006, 1 Page, XP002682890.
Communication Pursuant to Article 94(3) EPC from the European Patent Office for European Patent Application No. 07 868 397.6 dated Sep. 13, 2012, pp. 1-6.
Gala, J. L. et al. High expression of bcl-2 is the rule in acute lymphoblastic leukemia, except in Burkitt subtype at presentation, and is not correlated with the prognosis. Ann Hematol, 1994, vol. 69, p. 17-24.
Pusztai, L. et al. Clinical trial design for microarray predictive marker discovery and assessment. Annals of Oncology, 2004, vol. 15, pp. 1731-1737.
Golub, T. R. et al. Molecular Classification of Cancer: Class Discovery and Class Prediction by Gene Expression Monitoring. Science, Oct. 1999, vol. 286, pp. 531-537.
Benner, et al. Evolution, language and analogy in function genomics. Trends in Genetics, Jul. 2001, vol. 17, No. 7, pp. 414-418.
Cobb, J. Perren et al. Sepsis gene expression profiling: Murine splenic compared with hepatic responses determined by using complementary DNA microarrays. Crit. Care Med., 2002, vol. 30, No. 12. pp. 2711-2721.
Enard, W. et al. Intra-and Interspecific Variation in Primate Gene Expression Patterns. Science, 2002, vol. 296, pp. 340-343.
Zhu, H. et al. Screening of Novel Epilepsy-Related Genes and Isolation and Identification of cDNAs. Journal of Tongji Medical University, 2000, vol. 20, pp. 10-12.
Tsay, Y. H. et al. Cloning and Characterization of ERG8, an Essential of *Saccharomyces cerevisiae* That Encodes Phosphomevalonate Kinase. Molecular and Cellular Biology, Feb. 1991, vol. 11, No. 2, pp. 620-631.
Rinehart, C. A. et al. Aging and Cancer: The Role of Stromal Interactions With Epithelial Cells. Molecular Carcinogenesis, 1997, vol. 18, pp. 187-192.
International Search Report from International Application No. PCT/US2007/080826 dated Oct. 30, 2008.
Communication Relating to the Results of the Partial International Search from International Application No. PCT/US2008/004580 dated Dec. 8, 2008.
International Preliminary Report on Patentability from International Application No. PCT/US2007/080826 dated Apr. 23, 2009.
International Search Report and Written Opinion from International Application No. PCT/US2008/004580 dated Feb. 26, 2009.
Non-Final Office Action dated Jun. 27, 2014 from U.S. Appl. No. 12/081,101, filed Apr. 10, 2008, 19 pages.
Final Office Action dated Apr. 23, 2015 from U.S. Appl. No. 12/081,101, filed Apr. 10, 2008, 11 pages.

\* cited by examiner

Figure 5

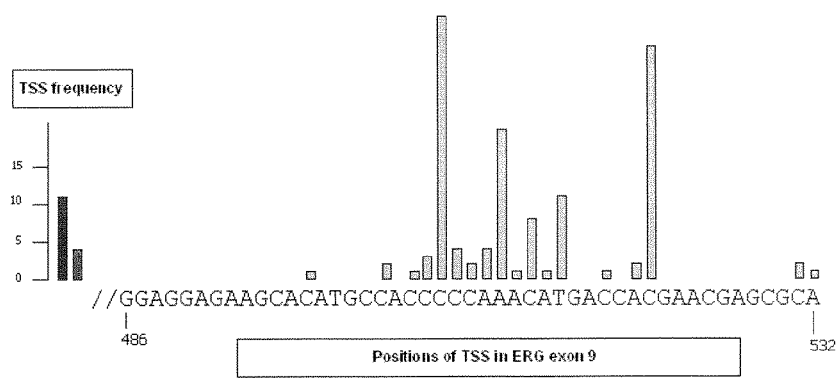

CapMap of cancer-specific ERG alternative transcription start sites (TSS)

Total RNA from 6 prostate cancer patients with ERG-TMPRSS2 fusion transcript expressing tumors were subjected to oligocapping. Oligocap-ligated mRNA species were converted to cDNA and were cloned into pUC19 vector. Nuclotide sequences were determined by DNA sequencing. 152 clones were sequenced. In 137 clones TSS was identified in ERG exon9 (yellow bars). TMPRSS2-ERG fusion transcripts were identified only in fifteen clones (red bar and purple bar respectively).

Figure 7

| Correlation | | No fusion detected | | | ERG Fusion A | | | High ERG fusion A* (Mean=0.61) | | | Low ERG fusion A* (Mean=4.64) | | |
|---|---|---|---|---|---|---|---|---|---|---|---|---|---|
| | | N | R | P value | N | R | P value | N | R | P value | N | R | P value |
| ERG fusion | ERG1 | - | - | - | 59 | 0.49 | <.0001 | 30 | 0.49 | 0.0055 | 29 | 0.33 | 0.079 |
| | AR | - | - | - | 61 | 0.22 | 0.0862 | 30 | 0.4 | 0.0303 | 31 | 0.08 | 0.672 |
| | PSA | - | - | - | 58 | 0.48 | 0.0001 | 31 | 0.56 | 0.0011 | 27 | 0.25 | 0.2037 |
| | PMEPA1 | | | | 50 | 0.55 | <.0001 | 24 | 0.59 | 0.0026 | 26 | 0.36 | 0.0718 |
| | LTF | - | - | - | 45 | 0.12 | 0.439 | 20 | 0.36 | 0.1203 | 25 | -0.11 | 0.6048 |
| ERG1 | AR | 26 | 0.48 | 0.0126 | 56 | 0.38 | 0.0039 | 27 | 0.57 | 0.002 | 29 | 0.06 | 0.7669 |
| | PSA | 27 | -0.01 | 0.9428 | 52 | 0.59 | <.0001 | 28 | 0.67 | 0.0001 | 24 | 0.09 | 0.6807 |
| | PMEPA1 | 22 | 0.28 | 0.1993 | 48 | 0.68 | <.0001 | 23 | 0.78 | <.0001 | 25 | 0.46 | 0.0211 |
| | LTF | 20 | 0.36 | 0.1125 | 43 | 0.01 | 0.9391 | 19 | -0.07 | 0.7717 | 24 | 0.01 | 0.9556 |

* Median split (median=2.635), N=65

Figure 8
A. Effect of ERG inhibition on AR regulated genes which are prostate differentiation marker (PSA) and CaP tumor suppressor gene (NKX3.1)
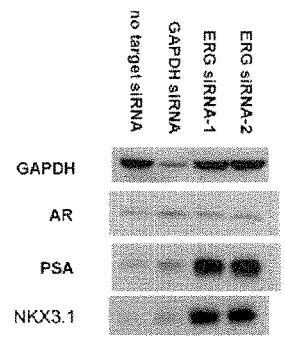
B. PSA levels in the VCaP cell line supernatant
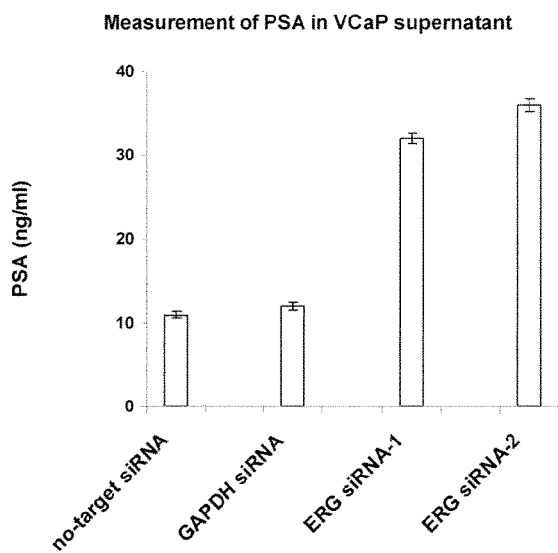

Figure 10
A.
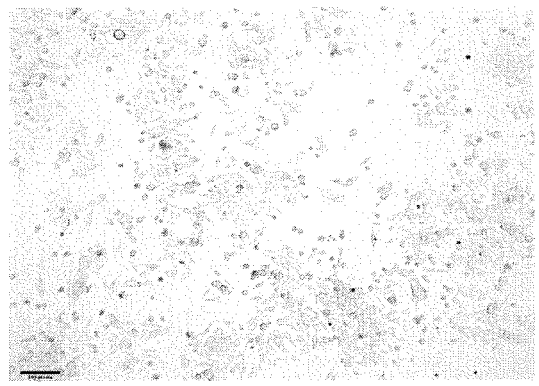
B.
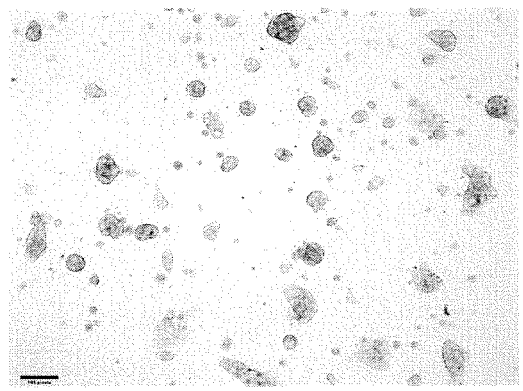

SEQUENCE LISTING

<160> NUMBER OF SEQ ID NOS: 29

<210> SEQ ID NO 1
<211> LENGTH: 1168
<212> TYPE: DNA
<213> ORGANISM: Homo sapiens

<400> SEQUENCE: 1
taggcgcgag ctaagcagga ggcggaggcg gaggcggagg gcgaggggcg gggagcgccg    60

```
cctggagcgc ggcaggaagc cttatcagtt gtgagtgagg accagtcgtt gtttgagtgt      120
gcctacggaa cgccacacct ggctaagaca gagatgaccg cgtcctcctc cagcgactat      180
ggacagactt ccaagatgag cccacgcgtc cctcagcagg attggctgtc tcaaccccca      240
gccagggtca ccatcaaaat ggaatgtaac cctagccagt gaatggctc aaggaactct       300
cctgatgaat gcagtgtggc caaaggcggg aagatggtgg gcagcccaga caccgttggg      360
atgaactacg gcagctacat ggaggagaag cacatgccac ccccaaacat gaccacgaac      420
gagcgcagag ttatcgtgcc agcagatcct acgctatgga gtacagacca tgtgcggcag      480
tggctggagt gggcggtgaa agaatatggc cttccagacg tcaacatctt gttattccag      540
aacatcgatg ggaaggaact gtgcaagatg accaaggacg acttccagag gctcacccccc    600
agctacaacg ccgacatcct tctctcacat ctccactacc tcagagagac tcctcttcca     660
catttgactt cagatgatgt tgataaagcc ttacaaaact ctccacggtt aatgcatgct     720
agaaacacag ggggtgcagc ttttattttc ccaaatactt cagtatatcc tgaagctacg     780
caaagaatta aactaggcc aggtacgaaa acaccccctgt gtgatctctt cattgagaga     840
catcccagat gtcctgctga gatccgtgcc ctaagtcacg tgatacaaag agagctgatc    900
ccggagctga agccagtccc agacagtctt attctgcctc tgttgatttg agactaaat    960
ccactcaaac catttcattc aaagaccaca ctaaaggaat taagagcaga ttagcccttt   1020
aactagcttt tcagaaagac agatgggcaa agaaggcatc ctggatgcct ggcagttagg    1080
aataggccga cttttgaact aacagaagga tctgtccctc ctcggggaa gagcacaaaa     1140
caaggacact ccccagattc acagtgac                                      1168

<210> SEQ ID NO 2
<211> LENGTH: 286
<212> TYPE: PRT
<213> ORGANISM: Homo sapiens

<400> SEQUENCE: 2

Met Thr Ala Ser Ser Ser Ser Asp Tyr Gly Gln Thr Ser Lys Met Ser
1               5                   10                  15

Pro Arg Val Pro Gln Gln Asp Trp Leu Ser Gln Pro Pro Ala Arg Val
                20                  25                  30

Thr Ile Lys Met Glu Cys Asn Pro Ser Gln Val Asn Gly Ser Arg Asn
            35                  40                  45

Ser Pro Asp Glu Cys Ser Val Ala Lys Gly Gly Lys Met Val Gly Ser
        50                  55                  60

Pro Asp Thr Val Gly Met Asn Tyr Gly Ser Tyr Met Glu Glu Lys His
65                  70                  75                  80

Met Pro Pro Pro Asn Met Thr Thr Asn Glu Arg Arg Val Ile Val Pro
                85                  90                  95

Ala Asp Pro Thr Leu Trp Ser Thr Asp His Val Arg Gln Trp Leu Glu
            100                 105                 110

Trp Ala Val Lys Glu Tyr Gly Leu Pro Asp Val Asn Ile Leu Leu Phe
        115                 120                 125

Gln Asn Ile Asp Gly Lys Glu Leu Cys Lys Met Thr Lys Asp Asp Phe
    130                 135                 140

Gln Arg Leu Thr Pro Ser Tyr Asn Ala Asp Ile Leu Leu Ser His Leu
145                 150                 155                 160

His Tyr Leu Arg Glu Thr Pro Leu Pro His Leu Thr Ser Asp Asp Val
                165                 170                 175
```

```
Asp Lys Ala Leu Gln Asn Ser Pro Arg Leu Met His Ala Arg Asn Thr
            180                 185                 190

Gly Gly Ala Ala Phe Ile Phe Pro Asn Thr Ser Val Tyr Pro Glu Ala
        195                 200                 205

Thr Gln Arg Ile Thr Thr Arg Pro Gly Thr Lys Thr Pro Leu Cys Asp
    210                 215                 220

Leu Phe Ile Glu Arg His Pro Arg Cys Pro Ala Glu Ile Arg Ala Leu
225                 230                 235                 240

Ser His Val Ile Gln Arg Glu Leu Ile Pro Glu Leu Lys Pro Val Pro
                245                 250                 255

Asp Ser Leu Ile Leu Pro Leu Leu Ile Trp Arg Leu Asn Pro Leu Lys
            260                 265                 270

Pro Phe His Ser Lys Thr Thr Leu Lys Glu Leu Arg Ala Asp
        275                 280                 285

<210> SEQ ID NO 3
<211> LENGTH: 1019
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gcaggaggcg gaggcggagg cggagggcga ggggcgggga gcgccgcctg gagcgcggca        60
ggaagcctta tcagttgtga gtgaggacca gtcgttgttt gagtgtgcct acggaacgcc       120
acacctggct aagacagaga tgaccgcgtc ctcctccagc gactatggac agacttccaa       180
gatgagccca cgcgtccctc agcaggattg gctgtctcaa cccccagcca gggtcaccat       240
caaaatggaa tgtaacccta gccaggtgaa tggctcaagg aactctcctg atgaatgcag       300
tgtggccaaa gcggaagata gtgtgggcag cccagacacc gttgggatga actacggcag       360
ctacatggag gagaagcaca tgccacccc aaacatgacc acgaacgagc gcagagttat       420
cgtgccagca gatcctacgc tatggagtac agaccatgtg cggcagtggc tggagtgggc       480
ggtgaaagaa tatggccttc cagacgtcaa catcttgtta ttccagaaca tcgatgggaa       540
ggaactgtgc aagatgacca aggacgactt ccagaggctc accccagct acaacgccga       600 catccttctc tcacatctcc actacctcag agagactcct cttccacatt tgacttcaga       660
tgatgttgat aaagccttac aaaactctcc acggttaatg catgctagaa acacagggg       720 tgcagctttt atttccccaa atacttcagt atatcctgaa gctacgcaaa gaattacaac       780
taggccagtc tcttacagat aaaacaacag aaccagtgcc agaaagcagc cttcccttac       840
atgggcactt ctgccaagca tatgagttca ttgccttgaa gatcaaagtc aaagagaat       900 ggagagggtg ttgaaatgat cagcgaaaat taaatgtaaa atatattctt attggaagtc       960
tgatgctcta ttatcaataa aggacacata gcaaagataa aaaaaaaaa aaaaaaaa       1019

<210> SEQ ID NO 4
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Thr Ala Ser Ser Ser Ser Asp Tyr Gly Gln Thr Ser Lys Met Ser
```

```
1               5                   10                  15
Pro Arg Val Pro Gln Gln Asp Trp Leu Ser Gln Pro Pro Ala Arg Val
            20                  25                  30

Thr Ile Lys Met Glu Cys Asn Pro Ser Gln Val Asn Gly Ser Arg Asn
            35                  40                  45

Ser Pro Asp Glu Cys Ser Val Ala Lys Gly Gly Lys Met Val Gly Ser
 50                  55                  60

Pro Asp Thr Val Gly Met Asn Tyr Gly Ser Tyr Met Glu Glu Lys His
 65                  70                  75                  80

Met Pro Pro Asn Met Thr Thr Asn Glu Arg Arg Val Ile Val Pro
                85                  90                  95

Ala Asp Pro Thr Leu Trp Ser Thr Asp His Val Arg Gln Trp Leu Glu
            100                 105                 110

Trp Ala Val Lys Glu Tyr Gly Leu Pro Asp Val Asn Ile Leu Leu Phe
            115                 120                 125

Gln Asn Ile Asp Gly Lys Glu Leu Cys Lys Met Thr Lys Asp Asp Phe
            130                 135                 140

Gln Arg Leu Thr Pro Ser Tyr Asn Ala Asp Ile Leu Leu Ser His Leu
145                 150                 155                 160

His Tyr Leu Arg Glu Thr Pro Leu Pro His Leu Thr Ser Asp Asp Val
                165                 170                 175

Asp Lys Ala Leu Gln Asn Ser Pro Arg Leu Met His Ala Arg Asn Thr
            180                 185                 190

Gly Gly Ala Ala Phe Ile Phe Pro Asn Thr Ser Val Tyr Pro Glu Ala
            195                 200                 205

Thr Gln Arg Ile Thr Thr Arg Pro Val Ser Tyr Arg
            210                 215                 220

<210> SEQ ID NO 5
<211> LENGTH: 807
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
acatcttgtt attccagaac atcgatggga aggaactgtg caagatgacc aaggacgact    60
tccagaggct caccccagc tacaacgccg acatccttct ctcacatctc cactacctca    120
gagagagtaa gctccccctt cctccaagga tagatggctg tggctatggt tcttatgacc    180
cgagcttcag agggttcaac caggtgtgtc gacagcatcc tcctgccctc gcccagttcc    240
cactggggat ccgagggagc acatgcttg ggtcctgcga ccaagaagat ggaatgtcaa    300 agggggaaagg aagcgttaac tggtcacaca ttagttaagt ctccatgata ccccgaatca    360
aaatagaatc attaaggctt ctctttcgta ggaattaggg ggattattct ccctaaagct    420
acatgaagcc ccactttata ttctaacctg agcacagaac aagggaagtt ttcactttgt    480
atcatgtgat tcggcttaac ctgacagaaa gggatggcat gttggcatga atccagaatg    540
tttgctgcat gctttaattt ctacaacgtc cagcatggtg agaaggaagt agtgtgacag    600
acagtgaggt ggataaaattc tcctccattg ctttgcctgg catcccaacc acttcttccc    660
tgaattaaag acgggccccc atgtaggttt taacatgcta acaagtagca ggttgctgga    720
aatagttata agcttcccat gatgttagtg tgggagtggg ggaacggttt ctttctttct    780
ttttctttct ttttttttt tttttt                                         807
```

<210> SEQ ID NO 6
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Thr Lys Asp Asp Phe Gln Arg Leu Thr Pro Ser Tyr Asn Ala Asp
1               5                   10                  15

Ile Leu Leu Ser His Leu His Tyr Leu Arg Glu Ser Lys Leu Pro Leu
            20                  25                  30

Pro Pro Arg Ile Asp Gly Cys Gly Tyr Gly Ser Tyr Asp Pro Ser Phe
        35                  40                  45

Arg Gly Phe Asn Gln Val Cys Arg Gln His Pro Pro Ala Leu Ala Gln
    50                  55                  60

Phe Pro Leu Gly Ile Arg Gly Ser His Met Leu Gly Ser Cys Asp Gln
65                  70                  75                  80

Glu Asp Gly Met Ser Lys Gly Lys Gly Ser Val Asn Trp Ser His Ile
                85                  90                  95

Ser

<210> SEQ ID NO 7
<211> LENGTH: 650
<212> TYPE: DNA
<213> ORGANISM: Homo sapiens

<400> SEQUENCE: 7
tctgtcgcca gtctggagtg cagtggcatg atctcagctc actgcaacct ccacctcccg      60
gattcaagca attttcctgc ctcagcctcc tgagtagctg ggactacagg catgcccagc     120
taatttttgt attttagta gagacggggt ttcaccatgt tggccaggat ggtctggatc     180
tcttgacctc atgatccgcc cacctcggca tcccaaagtg ttgggactac aggcatgagc     240
cacggcaccc cgcctgtatt tggcttttca cacttgtcct ttctccccca gtctcttccg     300
ccttgccctt ctttggttct ctctgtgtat tgtgagaagt cgatggagac atgctctttg     360
attgctgtta taatgaaga atatttcttc tcctccagga actctcctga tgaatgcagt      420
gtggccaaag gcgggaagat ggtgggcagc ccagacaccg ttgggatgaa ctacggcagc     480
tacatggagg agaagcacat gccaccccca aacatgacca cgaacgagcg cagagttatc     540
gtgccagcag gtcaggtgcc cacagcttca ctgccctcgg cagatcgcaa cttccccaag     600
gctaggctga gcctcaggga gctcttctcc cccacctgtg gcattgatca                650

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
taggcgcgag ctaagcagga g                                                21

<210> SEQ ID NO 9
<211> LENGTH: 23
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 9
ccaggatgcc ttctttgccc atc                                              23

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
accgttggga tgaactacgg ca                                               22

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccaggatgcc ttctttgccc atc                                              23

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ccctcccaag agtctttgga tctc                                             24

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cctggatttg caaggcggct act                                              23

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ctctccacgg ttaatgcatg ctag                                             24

<210> SEQ ID NO 15
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 15
cagaaagcag ccttcccttg                                                    20

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ttgataatag agcatcagac ttcca                                              25

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ttcagaaaga cagatgggca aa                                                 22

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gttcaaaagt cggcctattc ctaa                                               24

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
aaggcatcct ggatgcctgg ca                                                 22

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gcacttctgc caagcatatg agt                                                23

<210> SEQ ID NO 21
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 21
cgctgatcat ttcaacaccc t                                              21

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
tgccttgaag atcaaagtca aagagaaatg ga                                  32

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ttcagatgat gttgataaag ccttaca                                        27

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tccaggctga tctcctggg                                                 19

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
atgcatgcta gaaacacaga tttaccat                                       28

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ggcgttgtag ctgggggtga g                                              21

<210> SEQ ID NO 27
<211> LENGTH: 32
<212> TYPE: DNA
<213> ORGANISM: Artificial Sequence
<220> FEATURE:
<223> OTHER INFORMATION: Description of Artificial Sequence: Synthetic
```

```
      primer

<400> SEQUENCE: 27
caatgaattc gtctgtactc catagcgtag ga                                    32

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tgatgttgat aaagcctta                                                   19

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
cgacatcctt ctctcacat                                                   19
```

PROSTATE CANCER-SPECIFIC ALTERATIONS IN ERG GENE EXPRESSION AND DETECTION AND TREATMENT METHODS BASED ON THOSE ALTERATIONS

CROSS REFERENCE TO RELATED APPLICATIONS

This application is a continuation application of U.S. application Ser. No. 12/444,903 filed Apr. 9, 2009, which is a U.S. National Phase of International Application No. PCT/US2007/080826 filed Oct. 9, 2007, which claims the benefit of U.S. provisional application Nos. 60/929,505, filed Jun. 29, 2007, and 60/850,254 filed Oct. 10, 2006, the entire disclosure of each application is relied upon and incorporated by reference.

GOVERNMENT INTEREST

This invention was made with government support under grant numbers DK065977 and CA162383 awarded by the National Institutes of Health and contract number HU001-04-C-1502 awarded by the Uniformed Services University. The government has certain rights in the invention.

TECHNICAL FIELD

The invention relates to ERG polynucleotide and polypeptide sequences, as well as alterations in ERG gene expression, including splice variants of and promoter sequences of, the ERG gene that are involved in, or associated with, prostate cancer. The invention further relates to therapeutic compositions and to methods of detecting, diagnosing, and treating prostate cancer. The invention also relates to a panel of prostate cancer biomarkers that can be used to evaluate the functional status of androgen receptor signaling and in methods of prognosing prostate cancer, including biomarkers for detecting the expression of two or more of the following genes: PSA/KLK3, PMEPA1, NKX3.1, ODC1, AMD1, and ERG.

BACKGROUND

ETS Related Gene (ERG), a member of the ETS transcription family, was initially isolated and described in 1987 (Reddy et al., (1987) PROC. NATL. ACAD. SCI. USA 84:6131-35; Rao et al., (1987) SCIENCE 237: 635-39). Like other members of the ETS family, it plays a central role in mediating mitogenic signals transmitted by major cellular pathways, including the MAPK pathway. Proteins in the ETS family show a wide variety of expression patterns in human tissues. ERG is expressed in endothelial tissues, hematopoietic cells, kidney, and in the urogenital track. (Oikawa and Yamada, (2003) Gene, 303: 11-34.) Expression of ERG has also been detected in endothelial cells (microvessels) of the stroma in a small proportion of prostate cancer. (Gavrilov et al., (2001) EUR. J. CANCER, 37: 1033-40.)

The ERG protein participates in the regulation of gene expression by binding both to DNA comprising a 5'-GGA (A/T)-3' consensus sequence and to the Jun/Fos heterodimer. These interactions occur via the highly conserved ETS domain. (Verger et al., (2001) J. BIOL. CHEM., 276: 17181-89.) Splice variants exist, and of the nine that have been reported, ERG6 and ERG9 have multiple stop codons that likely render them non-functional. (Owczarek et al., (2004) GENE, 324: 65-77.) ERG7 and ERG8 can be distinguished from ERG1-5 by the absence of exon 16. (Id.) In addition, the ERG8 transcript is unique in its inclusion of a 3' sequence following exon 12, a portion of which forms part of the open reading frame. (Id.)

ERG, like other members of the ETS family, is a proto-oncogene with transforming activity. (Oikawa and Yamada, (2003) Gene, 303: 11-34; Hsu et al., (2004) J. Cell Biochem., 91:896-903; Reddy et al., (1987) Proc. Natl. Acad. Sci. USA, 84:6131-35; Hart et al., (1995) Oncogene, 10:1423-30; Sementchenko et al., (1998) Oncogene, 17:2883-88.) Chromosomal translocations involving ERG have been linked to Ewing sarcoma, myeloid leukemia, and cervical carcinoma. (Oikawa and Yamada, (2003) Gene, 303: 11-34.) It has recently been shown that ERG1 is the most commonly overexpressed proto-oncogene in malignant prostatic tissue. (Petrovics et al., (2005) Oncogene 24: 3847-52.) Independently, Tomlins et al., (2005) Science 310: 644-48, described novel gene fusions involving ERG and TMPRSS2, an androgen-sensitive gene, that may provide at least one possible mechanism for ERG1 overexpression. At least two additional studies have confirmed ERG rearrangements in prostate cancer. (Soller et al., (2006) Genes Chromosomes Cancer, 45:717-19; Yoshimoto et al., (2006) Neoplasia, 8: 465-69.)

Although prostate cancer is the most common non-skin cancer in North American men and the third leading cause of cancer mortality (Jemal et al., (2005) CA Cancer J. Clin., 56:106-30) remarkably little is known about critical events in prostatic carcinogenesis. While recent reports of high frequency genomic rearrangements involving the ERG locus and ERG1 overexpression are intriguing, there remains a need in the art to identify and characterize the gene expression products of the ERG locus in prostate cancer. Cancer-derived transcripts, splice variant transcripts, and altered expression ratios between transcripts are highly specific tools that can be used for cancer diagnosis throughout the different stages of cancer development. In addition, targeted inhibition or activation of these products, and/or direct manipulation of cancer-specific promoters, can be used as highly selective therapeutic strategies to target the causative root of cancer. Thus, the identification of molecular alterations specific for prostate cancer would not only permit optimization of diagnosis and prognosis but also would permit establishment of individualized treatments tailored to the molecular profile of the tumor.

In addition, while prostate cancer is increasingly detected early, the prognosis of individual patients remains a challenge. Identification of molecular biomarkers representing functionally relevant pathways that can distinguish between aggressive and indolent forms of prostate cancer at early stages will have tremendous impact in improving prognostic and therapeutic decisions. Other than serum PSA, currently there are no rational (tumor biology based) prognostic or therapeutic molecular biomarkers available in the clinical practice of prostate cancer.

While 80% of prostate cancer patients respond well to surgery, radiation therapy or watchful waiting, about 20% will develop metastasis that is often fatal to patients. Initially, prostate cancer development is driven by the androgen receptor (AR) pathway. (Heinlein et al., *Endocrine Rev* 25:276-308 (2004); Linja et al., *J Steroid Biochem Mol Biol* 92: 255-64 (2004); Shaffer et al., *Lancet Oncol* 4:407-14 (2003); Chen et al., *Nat Med* 10: 26-7 (2004).) However, frequent alterations of AR structure and/or function are well recognized during prostate cancer progression especially with metastatic disease. Other genetic pathways that are often altered in these late stage androgen-independent tumors include p53 mutations, BCL2 overexpression and mutations or reduced expression of PTEN. (Shaffer et al., *Lancet Oncol* 4:407-14 (2003).) Importantly, both p53 and PTEN pathways may affect AR functions.

Defects in AR-mediated signaling are increasingly highlighted for potential causal roles in prostate cancer progression. (Heinlein et al., *Endocrine Rev* 25:276-308 (2004); Dehm et al., *J Cell Biochem* 99: 333-344 (2006).) Prostate cancer associated alterations of AR functions by various mechanisms, including AR mutations, AR gene amplification, altered AR mRNA or AR protein levels, changes in AR interaction with co-activators/co-repressors and ligand independent AR activation by growth factors/cytokines, may all contribute to prostate cancer progression. (Gelmann E P. *J Clin Oncol* 20:3001-15 (2002); Grossman et al., *J Natl Cancer Inst* 93: 1687-97 (2001).) Due to the lack of precise knowledge of AR dysfunctions in pathologic specimens, it is difficult to identify patients with functional defects of AR.

The choice of therapy for late stage prostate cancer is systemic androgen ablation, which eventually fails in most patients. Therefore, the knowledge of AR pathway dysfunctions that are predictive of androgen ablation therapy failure would significantly impact the patient stratification for new emerging therapeutic strategies.

Unlike in breast cancer where estrogen receptor protein status in primary tumor is effectively used in making therapeutic and prognostic decisions (Yamashita et al., *Breast Cancer* 13(1):74-83 (2006); Martinez et al., *Am J Surg*. 191(2):281-3 (2006); Giacinti et al., *Oncologist* 11(1):1-8 (2006); Regan et al., *Breast* 14(6):582-93(2005); Singh et al., *J Cell Biochem.* 96(3):490-505 (2005)), AR protein expression status does not appear to be useful in prostate cancer, likely because many factors besides AR protein expression level may affect AR activity. Although AR expression can be detected throughout the progression of prostate cancer, it is heterogeneous and changes over time. Several studies have indicated that AR expression is reduced in poorly differentiated areas with higher Gleason score. (Heinlein et al., *Endocrine Rev* 25:276-308 (2004); Linja et al., *J Steroid Biochem Mol Biol* 92: 255-64 (2004); Shaffer et al., *Lancet Oncol* 4:407-14 (2003); Chen et al., *Nat Med* 10: 26-7 (2004); Gelmann E P. *J Clin Oncol* 20:3001-15 (2002); Grossman et al., *J Natl Cancer Inst* 93: 1687-97 (2001); Krishnan et al., *Clin Cancer Res* 6:1922-30 (2000).) In contrast, some recent reports found that higher AR expression is associated with higher clinical stage, higher Gleason score, and with decreased PSA recurrence-free survival. (Linja et al., *Cancer Res* 61:3550-55 (2001); Sweat et al., *J Urol* 161:1229-32 (1999); Li et al., *Am J Surg Pathol* 28:928-34 (2004).) Part of the reason for this controversy is the inherent heterogeneity of AR expression in the prostate and the semi-quantitative nature of immunohistochemical evaluations. (Krishnan et al., *Clin Cancer Res* 6:1922-30 (2000).) In recent years, our laboratory has established novel insights into the androgen regulated transcriptome and identified AR targets which have promise in defining the role of AR dysfunctions in prostate cancer, as well as in providing novel biology based biomarkers and therapeutic targets during prostate cancer progression. (Xu et al., *Cancer Res*. 63(15):4299-304 (2003); Segawa et al., *Oncogene* 21(57): 8749-58 (2002); Xu et al., *Int J Cancer* 92(3):322-8 (2001); Xu et al., *Genomics* 66(3): 257-263 (2000); Masuda et al., *J Mol Biol.* 353(4):763-71 (2005); Richter et al., *Prostate Cancer Prostatic Dis.* 2007 Feb. 13; [Epub ahead of print].)

Nevertheless, a need still exists to streamline the functional evaluation of AR defects at early stages of prostate cancer, when the impact of this knowledge on disease management will be more profound. The present application meets this need by providing a read out for the measurement of the expression of carefully selected AR downstream targets. This read out provides information on the in vivo functional status of AR in prostate cancer cells, which helps to stratify patients based on AR signal amplitude and can be used to help prognose prostate cancer and provide new ways of managing and treating these patients.

Citation of references herein shall not be construed as an admission that such references are prior art to the present invention.

SUMMARY

Transcription of the ERG gene is altered in prostate cancer cells compared to benign cells. The present application describes for the first time the predominant expression of the ERG8 isoform in cancerous cells. It also provides the sequence and characterization of two unique, cancer-specific transcripts of the ERG locus, ERG Prostate Cancer-specific Isoform 1 (EPC1) and EPC2. The disclosed ERG isoforms can be used alone or in combination as biomarkers of prostate cancer, as targets for therapeutic intervention, or to develop therapeutic agents. In addition, the disclosure describes a novel, prostate cancer-specific ERG promoter. The ERG promoter can be used to selectively target expression of therapeutic proteins, such as cellular toxins, to prostate cancer cells. Polynucleotide transcripts produced from this novel promoter can also be detected as biomarkers for prostate cancer diagnosis, or to aid in prognosis of prostate cancer.

In one aspect, the disclosure provides the nucleic acid sequences and encoded protein sequences for cancer-specific gene transcripts of the ERG locus, including ERG Prostate Cancer-specific Isoform 1 (EPC1) and EPC2. Antibodies to the encoded polypeptides, and to fragments of those polypeptides, are also described. In some embodiments, the antibody binds an epitope of the polypeptide or polypeptide fragment that is linear, whereas in other embodiments the epitope is conformational. In some embodiments, the epitope is contained within, or comprising, the unique carboxy-terminus of the EPC1 or EPC2 polypeptide. Some of the antibodies that bind an epitope in the carboxy terminus of EPC1 or EPC2 also bind the respective EPC1 or EPC2 polypeptide.

The disclosure further provides kits for detecting prostate cancer. These kits can be used to detect (either qualitatively or quantitatively) nucleic acids or proteins that serve as prostate cancer markers. For example, the expression of prostate cancer-specific isoforms of the ERG gene, such as ERG8, EPC1, EPC2, or the transcripts produced by the prostate cancer-specific promoter, when detected in a biological sample from a subject, either alone or in combination with other cancer markers, can be used to indicate the presence of prostate cancer in the subject or a higher predisposition of the subject to develop prostate cancer, or they can be used to predict the severity or stage of prostate cancer, such as whether the cancer is high risk or a moderate risk cancer.

In some embodiments, the kits comprise a nucleic acid probe, such as the probes described elsewhere in the disclosure, that hybridizes under defined conditions to an ERG sequence. The nucleic acid probe can hybridize to SEQ ID NO: 1 (ERG8), to SEQ ID NO: 3 (EPC1), to SEQ ID NO: 5 (EPC2) (or sequences complimentary to SEQ ID NO: 1, SEQ ID NO: 3, or SEQ ID NO: 5), or a combination of probes can be used to hybridize to ERG8 and EPC1, ERG8 and EPC2, EPC1 and EPC2, or even ERG8, EPC1, and EPC2. In other embodiments, the kits comprise first and second oligonucleotide primers that hybridize to non-overlapping sequences in ERG8 (SEQ ID NO: 1), EPC1 (SEQ ID NO: 3), or EPC2 (SEQ ID NO: 5). In some embodiments, primer pairs that hybridize to ERG8 and EPC1, ERG8 and EPC2, EPC1 and EPC2, or ERG8, EPC1, and EPC2, are used in combination. In such cases, one or more of the ERG8, EPC1, or EPC2 primers may be the same.

The disclosure additionally describes diagnostic kits comprising an anti-ERG isoform-specific antibody, for example, an anti-ERG8 antibody, an anti-EPC1 antibody, or anti-EPC2 antibody. In one embodiment, the disclosure provides an anti-EPC1 antibody that binds an epitope comprising acids amino acids 217 to 220 of SEQ ID NO: 4. In another embodiment, the antibody is an anti-EPC2 antibody that binds an epitope within or comprising amino acids 28 to 97 of SEQ ID NO: 6. In each case, the epitope can be a linear epitope or a conformational epitope. In some embodiments, combinations of antibodies can be included in the kit. For example, a kit can comprise anti-ERG8 and anti-EPC1 antibodies, anti-ERG8 and anti-EPC2 antibodies, anti-EPC1 and anti-EPC2 antibodies, or anti-ERG8, anti-EPC1, and anti-EPC2 antibodies. The antibodies can be, optionally, detectably labeled.

ERG isoform expression can be used to diagnose or prognose prostate cancer. The disclosure therefore also provides methods for detecting the expression of one or more of ERG8, EPC1, or EPC2 in a biological sample, such as prostate tissue, blood, serum, plasma, urine, saliva, or prostatic fluid. For example, in some embodiments, the methods comprise detecting amplification products of ERG8, EPC1, or EPC2 using hybridization-based techniques. In other embodiments, amplification products are size separated and visualized as part of the detection methods. The methods of diagnosing or prognosing prostate cancer can further comprise measuring the expression level (e.g. mRNA or polypeptide) of ERG8, EPC1, or EPC2, and correlating the expression level of the ERG isoform with the presence of prostate cancer or a higher predisposition to develop prostate cancer in the subject, or with the severity or stage of prostate cancer, such as high risk or moderate risk prostate cancer.

In some embodiments, the methods comprise detecting the expression of the ERG8 isoform. In other embodiments, it is the expression of the EPC1 isoform that is detected. In yet other embodiments, the EPC2 isoform is detected. In still other embodiments, the methods comprise detecting the ERG8 and EPC1 isoforms in combination, the ERG8 and EPC2 isoforms in combination, the EPC1 and EPC2 isoforms in combination, or the combination of the ERG8, EPC1, and EPC2 isoforms. In each case, each ERG isoform can be detected and/or measured by detecting and/or measuring the transcript, or by detecting and/or measuring the corresponding polypeptide.

Therapeutic methods of treating prostate cancer and treating disorders of prostate hyperproliferation are also disclosed. For example, the disclosure provides method of treating prostate cancer comprising destabilizing a prostate cancer-specific ERG gene transcript in prostate cancer cells. In some embodiments, the methods comprise destabilizing one, all, or any combination of ERG8, EPC1, EPC2, ERG1, ERG2, and/or ERG3 transcripts, resulting in degradation of those transcripts and inhibition of expression of the encoded polypeptide(s). In one embodiment, the destabilization employs siRNA. In another embodiment, the methods employ small hairpin RNAs (shRNA). In yet another embodiment, an antisense molecule is used to destabilize the transcript(s). In still another embodiment, a ribozyme is used to cause destabilization. Small molecule inhibitors can also be used to inhibit expression of one or more ERG isoforms. The disclosure also provides methods of using an antibody to one or more ERG isoforms to treat prostate cancer or disorders of prostate hyperproliferation. Thus, in varying embodiments the disclosure provides methods of treating prostate cancer or disorders of prostate hyperproliferation comprising administering an anti-ERG8, an anti-EPC1, an anti-EPC2, an anti-ERG1, and anti-ERG2, an anti-ERG3 antibody, or a combination of those antibodies. In some embodiments, a single antibody may be specific for one or more proteins encoded by the disclosed ERG isoforms.

In another embodiment, the present application provides a panel of biomarkers for prostate cancer, methods and systems for using those biomarkers to diagnose and prognose prostate cancer, and diagnostic and prognostic kits comprising reagents used to detect the biomarkers. In one embodiment the panel comprises a combination of two or more of a set of six androgen inducible/co-regulated genes (PSA/KLK3, PMEPA1, NKX3.1, ODC1, AMD1, and ERG). In some embodiments, the ERG gene is ERG8, EPC1, EPC2, ERG1, ERG2, ERG3, or combinations thereof.

The present application also provides prognostic kits that detect or measure the levels of two or more androgen inducible/co-regulated genes. The prognostic kits are used in methods of predicting the functional status of in vivo androgen receptor signaling or in methods of predicting prostate cancer progression or severity, such as predicting whether the prostate cancer is a moderate risk prostate cancer or a high risk prostate cancer, predicting the prostate cancer stage (e.g., using the T staging system (pTX, pT0, PT1, pT2, pT3, pT4) or the Whitmore-Jewett system (A,B, C,D)), or predicting whether the prostate cancer is progressing, regressing, or in remission. The prognostic kits can also be used to predict disease-free survival following prostatectomy, which can be defined, for example, by serum PSA level equal or higher than 0.2 ng/ml after prostatectomy. In some embodiments, the prognostic panel comprises two or more of the following genes: PSA/KLK3, PMEPA1, NKX3.1, ODC1, AMD1, and ERG. In certain embodiments, the ERG gene is ERG8, EPC1, EPC2, ERG1, ERG2, ERG3, or combinations thereof. Accordingly, assays using the prognostic kits can detect or measure the levels of two or more of these genes. For example, a prognostic kit can be used to measure the levels of two, three, four, five, six, or even more androgen inducible/co-regulated genes.

In certain embodiments, the prognostic assay further comprises detecting or measuring PSA, % fPSA, PSA doubling time, PSA velocity, prostate volume or a combination of these indicators.

In prognostic embodiments, the method of prognosing prostate cancer can comprise:

(a) detecting or measuring in a biological sample from an individual the expression of two or more of genes chosen from PSA/KLK3, PMEPA1, NKX3.1, ODC1, AMD1, and ERG; and (b) comparing, for the expression of each gene detected or measured in (a), the results obtained in (a) with the expression of the same gene in a control sample.

In a prognostic method, the altered expression of the two or more genes in the patient sample relative to the control sample is predictive of disease severity, for example a moderate risk prostate cancer or a high risk prostate cancer, or is predictive of whether the prostate cancer is progressing, regressing, or in remission. Alternatively, a threshold value of gene expression can be selected and used as the control sample. In this case, if the gene expression level is less than the threshold value, it is considered reduced. The threshold value can be determined using known techniques. For example, the value can be determined from the mRNA copy number or the cycle threshold value.

Although increases and decreases of at least 10% relative to a control or threshold value can be used in the prognostic methods, other values may also be used. For example, the increase or decrease may be at least 20, 30, 40, 50, 60, 70, 80, 90, 100, 200, 300, 400, or even 500%. The increase or decrease may also be expressed in terms of statistical significance, where a statistically significant increase or decrease in expression, such as $p<0.05$, $p<0.01$, $p<0.005$, or $p<0.001$, indicates the presence of prostate cancer or a higher predisposition to develop prostate cancer, prostate cancer progression, or disease severity.

In some prognostic embodiments, a decrease in expression levels of the androgen inducible/co-regulated gene(s) is used to predict compromised androgen receptor signaling, which in turn is predictive of the presence or predisposition to develop high risk or advanced stage prostate cancer or a reduced disease-free survival time following prostatectomy.

The disclosure also provides methods for detecting the expression of two or more of PSA/KLK3, PMEPA1, NKX3.1, ODC1, AMD1, and ERG (including ERG8, EPC1, EPC2, ERG1, ERG2, or ERG3) in a biological sample, such as prostate tissue or a biofluid, such as, blood, serum, plasma, urine, saliva, or prostatic fluid. For example, in some embodiments, the methods comprise detecting amplification products of PSA/KLK3, PMEPA1, NKX3.1, ODC1, AMD1, or ERG using hybridization-based techniques. In other embodiments, amplification products are size separated and visualized as part of the detection methods. The methods of prognosing prostate cancer can also comprise measuring the expression level of the proteins encoded by PSA/KLK3, PMEPA1, NKX3.1, ODC1, AMD1, or ERG, for example by using an antibody.

Additional objects will be set forth in part in the description that follows, and in part will be understood from the description, or may be learned by practice of the invention. It is to be understood that both the foregoing general description and the following detailed description are exemplary and explanatory only and are not restrictive of the invention as claimed.

BRIEF DESCRIPTION OF THE DRAWINGS

FIG. 4 shows the number of copies of the ERG isoforms.

FIG. 5 shows a map of alternative transcription start sites in ERG exon 9 (nucleotides 486 to 532 of SEQ ID NO: 7).

FIG. 7 provides the results of a Pearson correlation analysis of TMPRSS2-ERG fusion A transcript expression with ERG1, AR, PSA, PMEPA1 and LTF expression in tumor tissue.

FIG. 8 shows that downregulating ERG increases the expression of androgen receptor responsive genes. FIG. 8A is a gel showing that inhibition of ERG with two different siRNAs results in increased expression of androgen-inducible PSA and NKX3.1 transcripts. FIG. 8B shows that PSA levels also increase in the culture supernatant of VCaP cells when ERG is inhibited with siRNAs.

FIG. 10 presents the results of siRNA inhibition of ERG expression in VCaP prostate cancer cells. FIG. 10A is a microscope field of VCaP cells treated with control, while FIG. 10B is a microscope field of cells treated with siRNA-1.

DETAILED DESCRIPTION

I. Definitions

Figure 1:
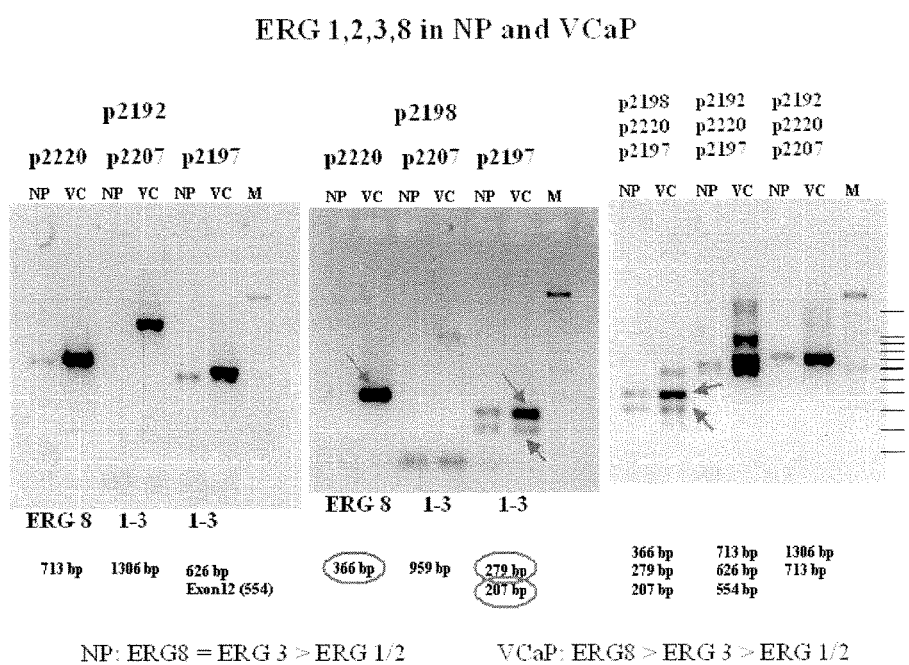
FIG. 1 presents PCR amplification gels of different ERG transcripts in normal prostate tissue (NP) and in the prostate cancer cell line VCaP.

The term "ERG" refers to the ERG gene, as well as to the various ERG cDNAs and mRNAs described in the disclosure. Unless a specific isoform or subset of isoforms is indicated, the term ERG includes ERG1, ERG2, ERG3, ERG4, ERG5, ERG6, ERG7, ERG8, ERG9, EPC1, EPC2, and the truncated ERG transcripts that result from activation of the prostate cancer-specific promoter described herein. The phrasing "ERG, but not" one or more specifically mentioned ERG isoforms may be used in embodiments in which several different, but not all, of the ERG isoforms are contemplated. The cDNA sequence of the ERG1 gene is published in GenBank under the accession number M21535. The cDNA sequence of the ERG2 gene is published in GenBank under the accession number M17254. The exon usage of ERG isoforms 1-9 is presented in Owczarek et al., (2004) GENE, 324: 65-77. When the context does not clearly exclude it, ERG also refers to the various ERG polypeptides encoded by the different isoforms. Further, although italics are generally used to refer to nucleic acids, the use of italics is not to be construed as excluding the encoded polypeptide.

To "destabilize" one or more transcripts means to cause degradation of that/those transcript(s) such that expression of the encoded polypeptide(s) is inhibited or knocked-down. Silent interfering RNA (siRNA), small hairpin RNA (shRNA) (for example, as described by Paddison et al., (2002) GENES DEV. 16 (8): 948-58), antisense molecules, ribozymes, and combinations of these approaches can be used in methods of destabilizing a transcript(s).

A "moderate risk" prostate cancer is cancer in which the patient has, for example, no PSA recurrence, a Gleason score of 6-7, T2a-T3b stage, no seminal vesicle invasion, and well or moderate tumor differentiation.

A "high risk" prostate cancer is cancer in which the patient has, for example, PSA recurrence, a Gleason score of 8-9, T3c stage, seminal vesicle invasion, and poor tumor differentiation.

The term "altered expression" refers both to qualitative differences (i.e., that gene or protein expression is detectable versus undetectable) and to quantitative differences (i.e., differences in measured levels of gene or protein expression).

The term "isolated" refers to a molecule that is substantially free of its natural environment. Any amount of that molecule elevated over the naturally occurring levels due to any manipulation, e.g., over expression, partial purification, etc., is encompassed with the definition. With regard to partially purified compositions only, the term refers to an isolated compound that is at least 50-70%, 70-90%, 90-95% (w/w), or more pure.

The phrase "substantially identical," or "substantially as set out," means that a relevant sequence is at least 70%, 75%, 80%, 85%, 90%, 95%, 97, 98, or 99% identical to a given sequence. By way of example, such sequences may be allelic variants, sequences derived from various species, or they may be derived from the given sequence by truncation, deletion, amino acid substitution or addition. For polypeptides, the length of comparison sequences will generally be at least 20, 30, 50, 100 or more amino acids. For nucleic acids, the length of comparison sequences will generally be at least 50, 100, 150, 300, or more nucleotides. Percent identity between two sequences is determined by standard alignment algorithms such as, for example, Basic Local Alignment Tool (BLAST) described in Altschul et al. (1990) J. Mol. Biol., 215:403-410, the algorithm of Needleman et al. (1970) J. Mol. Biol., 48:444-453, or the algorithm of Meyers et al. (1988) Comput. Appl. Biosci., 4:11-17.

"Protein" is used interchangeably with the terms "peptide" and "polypeptide" and refers to any chain of amino acids, regardless of length or posttranslational modification (e.g., glycosylation or phosphorylation), or source (e.g., species).

The terms "polynucleotide," "oligonucleotide," "nucleic acid," and "DNA" are used interchangeably herein and refer to deoxyribonucleic acid (DNA), and, where appropriate, ribonucleic acid (RNA). The term should also be understood to include nucleotide analogs, and single or double stranded polynucleotides. Examples of polynucleotides include, but are not limited to, plasmid DNA or fragments thereof, viral DNA or RNA, anti-sense RNA, etc. The term "plasmid DNA" refers to double stranded DNA that is circular.

As used herein the term "hybridization under defined conditions," or "hybridizing under defined conditions," is intended to describe conditions for hybridization and washes under which nucleotide sequences that are significantly identical or homologous to each other remain bound to each other. The conditions are such that sequences, which are at least about 6 and more preferably at least about 20, 30, 40, 50, 100, 150, 300, or more nucleotides long and at least about 70%, more preferably at least about 80%, even more preferably at least about 85-90% identical, remain bound to each other. The percent identity can be determined as described in Altschul et al. *Nucleic Acids Res.*, 25: 3389-3402 (1997). Appropriate hybridization conditions can be selected by those skilled in the art with minimal experimentation as exemplified in Ausubel et al. (2004), Current Protocols in Molecular Biology, John Wiley & Sons. Additionally, stringent conditions are described in Sambrook et al. (2001) Molecular Cloning: A Laboratory Manual, $3^{rd}$ ed., Cold Spring Harbor Laboratory Press.

A nonlimiting example of defined conditions of low stringency is as follows: Filters containing DNA are pretreated for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA. Hybridizations are carried out in the same solution with the following modifications: 0.02% PVP, 0.02% Ficoll, 0.2% BSA, 100 μg/ml salmon sperm DNA, 10% (wt/vol) dextran sulfate, and 5-20×$10^6$ cpm $^{32}$P-labeled probe is used. Filters are incubated in hybridization mixture for 18-20 hours at 40° C., and then washed for 1.5 hours at 55° C. in a solution containing 2×SSC, 25 mM Tris-HCl (pH 7.4), 5 mM EDTA, and 0.1% SDS. The wash solution is replaced with fresh solution and incubated an additional 1.5 hours at 60° C. Filters are blotted dry and exposed for autoradiography. Other conditions of low stringency well known in the art may be used (e.g., as employed for cross-species hybridizations).

A non-limiting example of defined conditions of high stringency is as follows: Prehybridization of filters containing DNA is carried out for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 μg/ml denatured salmon sperm DNA. Filters are hybridized for 48 hours at 65° C. in the prehybridization mixture containing 100 μg/ml denatured salmon sperm DNA and 5-20×$10^6$ cpm of $^{32}$P-labeled probe. Washing of filters is done at 37° C. for 1 hour in a solution containing 2×SSC, 0.01% PVP, 0.01% Ficoll, and 0.01% BSA. This is followed by a wash in 0.1×SSC at 50° C. for 45 minutes. Another non-limiting example of defined conditions of high stringency is as follows: Prehybridization of filters containing DNA is carried out for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 μg/ml denatured salmon sperm DNA. Filters are hybridized for 12 hours at 65° C. in the prehybridization mixture containing 100 µg/ml denatured salmon sperm DNA and 5-20×10$^6$ cpm of $^{32}$P-labeled probe. Washing of filters is done at 37° C. for 1 hour in a solution containing 2×SSC, 0.01% PVP, 0.01% Ficoll, and 0.01% BSA. This is followed by a wash in 0.1×SSC at 50° C. for 45 minutes. Other conditions of high stringency well known in the art may be used. An oligonucleotide hybridizes specifically to a target sequence under high stringency conditions.

The term "primer" or "oligonucleotide primer" means an oligonucleotide capable of binding to a region of a target nucleic acid, or its complement, and promoting nucleic acid amplification of the target nucleic acid. Generally, a primer will have a free 3' end that can be extended by a nucleic acid polymerase. Primers also generally include a base sequence capable of hybridizing via complementary base interactions either directly with at least one strand of the target nucleic acid or with a strand that is complementary to the target sequence. A primer may comprise target-specific sequences and optionally other sequences that are non-complementary to the target sequence. These non-complementary sequences may comprise, for example, a promoter sequence or a restriction endonuclease recognition site.

The term "solid support" means a material that is essentially insoluble under the solvent and temperature conditions of the assay method, comprising free chemical groups available for joining an oligonucleotide or nucleic acid. Preferably, the solid support is covalently coupled to an oligonucleotide designed to directly or indirectly bind a target nucleic acid. When the target nucleic acid is an mRNA, the oligonucleotide attached to the solid support is preferably a poly-T sequence. A preferred solid support is a particle, such as a micron- or submicron-sized bead or sphere. A variety of solid support materials are contemplated, such as, for example, silica, polyacrylate, polyacrylamide, a metal, polystyrene, latex, nitrocellulose, polypropylene, nylon or combinations thereof. In some embodiments, the solid support is capable of being attracted to a location by means of a magnetic field, such as a solid support having a magnetite core.

The term "detecting" or "detection" means any of a variety of methods known in the art for determining the presence of a nucleic acid or a protein. For example, hybridizing a labeled probe to a portion of a nucleic acid is one way to detect that nucleic acid. Binding an antibody that is either directly or indirectly labeled to a protein of interest is an example of a method for detecting that protein. Methods for labeling nucleic acids and antibodies (as well as other proteins) are well known in the art. Labels can be either detectable or functional labels, and include radiolabels (e.g., $^{131}$I, $^{125}$I, $^{35}$S, and $^{99}$Tc), enzymatic labels (e.g., horseradish peroxidase or alkaline phosphatase), chemiluminescent labels, and other chemical moieties (e.g., biotin). A labeled probe is an oligonucleotide that specifically binds to another sequence and contains a detectable group which may be, for example, a fluorescent moiety, a chemiluminescent moiety (such as an acridinium ester (AE) moiety that can be detected chemiluminescently under appropriate conditions (as described in U.S. Pat. No. 5,283,174)), a radioisotope, biotin, avidin, enzyme, enzyme substrate, or other reactive group. Other well know detection techniques include, for example, gel filtration, gel electrophoresis and visualization of the amplicons by, for example, staining with ethidium bromide, and High Performance Liquid Chromatography (HPLC). Antibody-based detection methods include ELISA, western blotting, RIA, immunohistochemistry, and other techniques that are well known in the art. As used throughout the specification, the term "detecting" or "detection" includes either qualitative or quantitative detection.

The term "treatment" is used interchangeably herein with the term "therapeutic method" and refers to both therapeutic treatment and prophylactic/preventative measures. Those in need of treatment may include individuals already having a particular medical disorder as well as those who may ultimately acquire the disorder.

The term "effective dose," or "effective amount," refers to that amount of the compound that results in amelioration of symptoms in a patient or a desired biological outcome, e.g., inhibition of cell proliferation. The effective amount can be determined as described in the subsequent sections.

The term "modulatory compound" is used interchangeably with the term "therapeutic" and as used herein means any compound capable of "modulating" either prostate cancer-specific gene expression at the transcriptional, translational, or post-translational levels or modulating the biological activity of a prostate cancer-specific polypeptide. The term "modulate" and its cognates refer to the capability of a compound acting as either an agonist or an antagonist of a certain reaction or activity. The term modulate, therefore, encompasses the terms "activate" and "inhibit." The term "activate," for example, refers to an increase in the expression of the prostate cancer-specific gene or activity of a prostate cancer-specific polypeptide in the presence of a modulatory compound, relative to the activity of the gene or the polypeptide in the absence of the same compound. The increase in the expression level or the activity is preferably at least about 10%, 20%, 30%, 40%, 50%, 60%, 70%, 80%, 90%, or higher. Analogously, the term "inhibit" refers to a decrease in the expression of the prostate cancer-specific gene or activity of a prostate cancer-specific polypeptide in the presence of a modulatory compound, relative to the activity of the gene or the polypeptide in the absence of the same compound. The decrease in the expression level or the activity is preferably at least about 10%, 20%, 30%, 40%, 50%, 60%, 70%, 80%, 90%, or higher. The expression level of the prostate cancer-specific gene or activity of a prostate cancer-specific polypeptide can be measured as described herein or by techniques generally known in the art.

"Antibody" refers to an immunoglobulin or fragment thereof, and encompasses any polypeptide comprising an antigen-binding fragment or an antigen-binding domain. The term includes but is not limited to polyclonal, monoclonal, monospecific, polyspecific, humanized, human, single-chain, chimeric, synthetic, recombinant, hybrid, mutated, grafted, and in vitro generated antibodies. Unless preceded by the word "intact", the term "antibody" includes antibody fragments such as Fab, F(ab')$_2$, Fv, scFv, Fd, dAb, and other antibody fragments that retain antigen-binding function. Unless otherwise specified, an antibody is not necessarily from any particular source, nor is it produced by any particular method.

The terms "specific interaction," "specific binding," or the like, mean that two molecules form a complex that is relatively stable under physiologic conditions. The term is also applicable where, e.g., an antigen-binding domain is specific for a particular epitope, which is carried by a number of antigens, in which case the specific binding member carrying the antigen-binding domain will be able to bind to the various antigens carrying the epitope. Specific binding is characterized by a high affinity and a low to moderate capacity. Nonspecific binding usually has a low affinity with a moderate to high capacity. Typically, the binding is considered specific when the affinity constant $K_a$ is higher than $10^6 M^{-1}$, more preferably higher than $10^7 M^{-1}$, and most preferably $10^8 M^{-1}$. If necessary, non-specific binding can be reduced without substantially affecting specific binding by varying the binding conditions. Such conditions are known in the art, and a skilled artisan using routine techniques can select appropriate conditions. The conditions are usually defined in terms of concentration of antibodies, ionic strength of the solution, temperature, time allowed for binding, concentration of non-related molecules (e.g., serum albumin, milk casein), etc.

9 of the ERG gene. In the case of ERG8, this splice variant of the ERG gene has been described (Owczarek et al., GENE 324: 65-77 (2004)), but its overexpression in the context of prostate cancer was not previously known. The protein encoded by ERG8 lacks the DNA binding domain found in ERG1 and ERG2 but retains the entire protein-protein interaction domain. The expression of ERG8, therefore, likely results in the functional nullification of protein interaction partners of ERG1 and ERG2, resulting in a dominant negative effect.

The disclosure also shows that fusions occur between ERG8 and TMPRSS2. An example of a TMPRSS2-ERG8 fusion transcript is:

```
TAGGCGCGAG CTAAGCAGGA GGCGGAGGCG GAGGCGGAGG GCGAGGGGCG    50

GGGAGCGCCG CCTGGAGCGC GGCAGGAAGC CTTATCAGTT GTGAGTGAGG   100

ACCAGTCGTT GTTTGAGTGT GCCTACGGAA CGCCACACCT GGCTAAGACA   150

GAGATGACCG CGTCCTCCTC CAGCGACTAT GGACAGACTT CCAAGATGAG   200

CCCACGCGTC CCTCAGCAGG ATTGGCTGTC TCAACCCCCA GCCAGGGTCA   250

CCATCAAAAT GGAATGTAAC CCTAGCCAGG TGAATGGCTC AAGGAACTCT   300

CCTGATGAAT GCAGTGTGGC CAAAGGCGGG AAGATGGTGG GCAGCCCAGA   350

CACCGTTGGG ATGAACTACG GCAGCTACAT GGAGGAGAAG CACATGCCAC   400

CCCCAAACAT GACCACGAAC GAGCGCAGAG TTATCGTGCC AGCAGATCCT   450

ACGCTATGGA GTACAGACCA TGTGCGGCAG TGGCTGGAGT GGGCGGTGAA   500

AGAATATGGC CTTCCAGACG TCAACATCTT GTTATTCCAG AACATCGATG   550

GGAAGGAACT GTGCAAGATG ACCAAGGACG ACTTCCAGAG GCTCACCCCC   600

AGCTACAACG CCGACATCCT TCTCTCACAT CTCCACTACC TCAGAGAGAC   650

TCCTCTTCCA CATTTGACTT CAGATGATGT TGATAAAGCC TTACAAAACT   700

CTCCACGGTT AATGCATGCT AGAAACACAG GGGGTGCAGC TTTTATTTTC   750

CCAAATACTT CAGTATATCC TGAAGCTACG CAAAGAATTA CAACTAGGCC   800

AGGTACGAAA ACACCCCTGT GTGATCTCTT CATTGAGAGA CATCCCAGAT   850

GTCCTGCTGA GATCCGTGCC CTAAGTCACG TGATACAAAG AGAGCTGATC   900

CCGGAGCTGA AGCCAGTCCC AGACAGTCTT ATTCTGCCTC TGTTGATTTG   950

GAGACTAAAT CCACTCAAAC CATTTCATTC AAAGACCACA CTAAAGGAAT  1000

TAAGAGCAGA TTAGCCCTTT AACTAGCTTT TCAGAAAGAC AGATGGGCAA  1050

AGAAGGCATC CTGGATGCCT GGCAGTTAGG AATAGGCCGA CTTTTGAACT  1100

AACAGAAGGA TCTGTCCCTC CTCGGGGGAA GAGCACAAAA CAAGGACACT  1150

CCCCAGATTC ACAGTGAC
```

II. Prostate Cancer-Specific ERG Nucleic Acids

The disclosure describes prostate cancer-specific ERG isoform nucleic acids, in particular, ERG8, EPC1, EPC2, and a prostate cancer-specific promoter located within exon (SEQ ID NO: 1). The TMPRSS2-derived sequence is shown in bold. Exon junctions are shown in grey boxes. The initiation codon and stop codon are shown in bold italics. The unique 3' sequence is underlined. The amino acid sequence of ERG8 is:

```
MTASSSSDYG QTSKMSPRVP QQDWLSQPPA RVTIKMECNP SQVNGSRNSP    50

DECSVAKGGK MVGSPDTVGM NYGSYMEEKH MPPPNMTTNE RRVIVPADPT   100

LWSTDHVRQW LEWAVKEYGL PDVNILLFQN IDGKELCKMT KDDFQRLTPS   150

YNADILLSHL HYLRETPLPH LTSDDVDKAL QNSPRLMHAR NTGGAAFIFP   200
```

```
NTSVYPEATQ RITTRPGTKT PLCDLFIERH PRCPAEIRAL SHVIQRELIP    250

ELKPVPDSLI LPLLIWRLNP LKPFHSKTTL KELRAD
```

(SEQ ID NO: 2). The unique carboxy terminus of ERG8 is underlined.

EPC1 is an ERG isoform that is selectively expressed in cancerous prostate cells. The nucleic acid sequence of EPC1 is:

```
GCAGGAGGCG GAGGCGGAGG CGGAGGGCGA GGGGCGGGGA GCGCCGCCTG    50

GAGCGCGGCA ░AAGCCTTA TCAGTTGTGA GTGAGGACCA GTCGTTGTTT    100

GAGTGTGCCT ACGGAACGCC ACACCTGGCT AAGACAGAGA TGCGCGTC     150

CTCCTCCAGC GACTATGGAC AGACTTCCAA GATGAGCCCA CGCGTCCCTC   200

AGCAGGATTG GCTGTCTCAA CCCCCAGCCA GGGTCACCAT CAAAATGGAA   250

TGTAACCCTA GCCAGGTGAA TGGCTCAA░ AACTCTCCTG ATGAATGCAG    300

TGTGGCCAAA GGCGGGAAGA TGGTGGGCAG CCCAGACACC GTTGGGATGA   350

ACTACGGCAG CTACATGGAG GAGAAGCACA TGCCACCCCC AAACATGACC   400

ACGAACGAGC GCAGAGTTAT CGTGCCAGCA ░TCCTACGC TATGGAGTAC    450

AGACCATGTG CGGCAGTGGC TGGAGTGGGC GGTGAAAGAA TATGGCCTTC   500

CAGACGTCAA CATCTTGTTA TTCCAGAACA TCGATGGGAA GGAACTGTGC   550

AAGATGACCA AGGACGACTT CCAGAGGCTC ACCCCCAGCT ACAACGCCGA   600

CATCCTTCTC TCACATCTCC ACTACCTCAG AGAGACTCCT CTTCCACATT   650

TGACTTCAGA TGATGTTGAT AAAGCCTTAC AAAACTCTCC ACGGTTAATG   700

CATGCTAGAA ACACAGGGGG TGCAGCTTTT ATTTTCCCAA ATACTTCAGT   750

ATATCCTGAA GCTACGCAAA GAATTACAAC TAGGCCAGTC TCTTACAGAT   800

AAAACAACAG AACCAGTGCC AGAAAGCAGC CTTCCCTTAC ATGGGCACTT   850

CTGCCAAGCA TATGAGTTCA TTGCCTTGAA GATCAAAGTC AAAGAGAAAT   900

GGAGAGGGTG TTGAAATGAT CAGCGAAAAT TAAATGTAAA ATATATTCTT   950

ATTGGAAGTC TGATGCTCTA TTATCAATAA AGGACACATA GCAAAGATAA   1000

AAAAAAAAAA AAAAAAAA
```

(SEQ ID NO: 3). In the sequence, the TMPRSS2-derived sequence is shown in bold. Exon junctions are shown in grey boxes. The initiation codon and stop codon are shown in bold italics. The 3' end of the EPC1 transcript is distinct from all known ERG isoforms. This unique sequence is underlined. The amino acid sequence of EPC1 is:

```
MTASSSSDYG QTSKMSPRVP QQDWLSQPPA RVTIKMECNP SQVNGSRNSP    50

DECSVAKGGK MVGSPDTVGM NYGSYMEEKH MPPPNMTTNE RRVIVPADPT   100

LWSTDHVRQW LEWAVKEYGL PDVNILLFQN IDGKELCKMT KDDFQRLTPS   150

YNADILLSHL HYLRETPLPH LTSDDVDKAL QNSPRLMHAR NTGGAAFIFP   200

NTSVYPEATQ RITTRPVSYR
```

(SEQ ID NO: 4). EPC1 comprises additional nucleotides at its 3' end that encode four unique amino acids at the carboxy terminus of the EPC1 protein. These four unique amino acids are underlined in SEQ ID NO: 4. Because EPC1, like ERG8, lacks the coding sequences for the DNA-binding domain, it may also have a dominant negative effect.

EPC2 is also selectively expressed in cancerous prostate cells. The nucleic acid sentience of EPC2 is:

```
ACATCTTGTT ATTCCAGAAC ATCGATGGGA AGGAACTGTG CAAGATGACC      50

AAGGACGACT TCCAGAGGCT CACCCCCAGC TACAACGCCG ACATCCTTCT     100

CTCACATCTC CACTACCTCA GAGAGA TAA GCTCCCCCTT CCTCCAAGGA     150

TAGATGGCTG TGGCTATGGT TCTTATGACC CGAGCTTCAG AGGGTTCAAC     200

CAGGTGTGTC GACAGCATCC TCCTGCCCTC GCCCAGTTCC CACTGGGGAT     250

CCGAGGGAGC CACATGCTTG GGTCCTGCGA CCAAGAAGAT GGAATGTCAA     300

AGGGGAAAGG AAGCGTTAAC TGGTCACACA TTAGTTAAGT CTCCATGATA     350

CCCCGAATCA AAATAGAATC ATTAAGGCTT CTCTTTCGTA GGAATTAGGG     400

GGATTATTCT CCCTAAAGCT ACATGAAGCC CCACTTTATA TTCTAACCTG     450

AGCACAGAAC AAGGGAAGTT TTCACTTTGT ATCATGTGAT TCGGCTTAAC     500

CTGACAGAAA GGGATGGCAT GTTGGCATGA ATCCAGAATG TTTGCTGCAT     550

GCTTTAATTT CTACAACGTC CAGCATGGTG AGAAGGAAGT AGTGTGACAG     600

ACAGTGAGGT GGATAAATTC TCCTCCATTG CTTTGCCTGG CATCCCAACC     650

ACTTCTTCCC TGAATTAAAG ACGGGCCCCC ATGTAGGTTT TAACATGCTA     700

ACAAGTAGCA GOTTGCTGGA AATAGTTATA AGCTTCCCAT GATGTTAGTG     750

TGGGAGTGGG GGAACGGTTT CTTTCTTTCT TTTTCTTTCT TTTTTTTTT     800

TTTTTTT
```

(SEQ ID NO: 5). The initiation codon and stop codon are shown in bold italics. An exon junction is shown in the grey box. The unique 3' sequence is underlined. The amino acid sequence of EPC2 is:

```
MTKDDFQRLT PSYNADILLS HLHYLRESKL PLPPRIDGCG YGSYDPSFRG      50

FNQVCRQHPP ALAQFPLGIR GSHMLGSCDQ EDGMSKGKGS VNWSHIS
```

(SEQ ID NO: 6). The unique carboxy terminus of EPC2 is underlined in SEQ ID NO: 6.

The disclosure also describes the activation of a promoter in prostate cancer cells. Activation of this promoter produces transcripts coding for ERG isoforms lacking the N-terminal protein-protein interaction domain of wild type ERG. Therefore, expression products of this promoter sequence in prostate cancer cells appear to act as dominant negative or gain-of-function molecules. The promoter is located within the following sequence from exon 9 of the ERG gene:

```
TCTGTCGCCA GTCTGGAGTG CAGTGGCATG ATCTCAGCTC ACTGCAACCT      50

CCACCTCCCG GATTCAAGCA ATTTTCCTGC CTCAGCCTCC TGAGTAGCTG     100

GGACTACAGG CATGCCCAGC TAATTTTTGT ATTTTTAGTA GAGACGGGGT     150

TTCACCATGT TGGCCAGGAT GGTCTGGATC TCTTGACCTC ATGATCCGCC     200

CACCTCGGCA TCCCAAAGTG TTGGGACTAC AGGCATGAGC CACGGCACCC     250

CGCCTGTATT TGGCTTTTCA CACTTGTCCT TTCTCCCCCA GTCTCTTCCG     300

CCTTGCCCTT CTTTGGTTCT CTCTGTGTAT TGTGAGAAGT CGATGGAGAC     350

ATGCTCTTTG ATTGCTGTTA TAATGGAAGA ATATTTCTTC TCCTCCAGGA     400

ACTCTCCTGA TGAATGCAGT GTGGCCAAAG GCGGGAAGAT GGTGGGCAGC     450

CCAGACACCG TTGGGATGAA CTACGGCAGC TACATGGAGG AGAAGCACAT     500

GCCACCCCCA AACATGACCA CGAACGAGCG CAGAGTTATC GTGCCAGCAG     550

GTCAGGTGCC CACAGCTTCA CTGCCCTCGG CAGATCGCAA CTTCCCCAAG     600

GCTAGGCTGA GCCTCAGGGA GCTCTTCTCC CCCACCTGTG GCATTGATCA     650
```

(SEQ ID NO: 7). In the sequence, the most 3' transcription start site is bolded and shown in a grey box. A sequence comprising at least nucleotides 521 to 650 of SEQ ID NO: 7 retain promoter activity.

III. Diagnostic Compositions and Methods

The ERG isoform nucleic acids, the polypeptides they encode, and antibodies to those polypeptides can be employed in various diagnostic and prognostic applications for prostate cancer because ERG8, EPC1, EPC2, and the transcripts from the prostate cancer-specific promoter are each associated with prostate cancer.

Accordingly, the disclosure provides methods for detecting prostate cancer in a biological sample, comprising:
  (a) combining the biological sample with at least a first and a second oligonucleotide primer under hybridizing conditions, wherein the first oligonucleotide primer contains a sequence that hybridizes to a first sequence in a target sequence from ERG8, EPC1, EPC2, or the transcripts from the prostate cancer-specific promoter and the second oligonucleotide primer contains a sequence that hybridizes to a second sequence in a nucleic acid strand complementary to the target sequence, wherein the first sequence does not overlap with the second sequence;
  (b) amplifying a plurality of amplification products when the target sequence is present in the biological sample by adding at least one polymerase activity to the biological sample containing the first and second oligonucleotide primers;
  (c) immobilizing the plurality of amplification products on a solid support;
  (d) combining an oligonucleotide probe with the immobilized plurality of amplification products to thereby permit the probe to hybridize to at least one immobilized amplification product; and
  (e) detecting whether a signal results from hybridization between the oligonucleotide probe and at least one amplification product, wherein detection of the signal indicates the expression of ERG8, EPC1, EPC2, or the transcripts from the prostate cancer-specific promoter and the presence of prostate cancer in the biological sample. Detecting a signal resulting from hybridization between the oligonucleotide probe and the at least one amplification product can be used to diagnose or prognose prostate cancer.

In some embodiments in which the ERG isoform is fused to TMPRSS2, the first oligonucleotide primer contains a sequence that hybridizes to a first sequence in a target sequence from TMPRSS2 and the second oligonucleotide primer contains a sequence that hybridizes to a second sequence in a nucleic acid strand complementary to a target sequence from ERG8, EPC1, EPC2, or the transcripts from the prostate cancer-specific promoter.

Accordingly, the disclosure provides methods for detecting prostate cancer in a biological sample, wherein the target sequence comprises all or part of SEQ ID NO: 1, SEQ ID NO: 3, SEQ ID NO: 5, or SEQ ID NO: 7. In other embodiments, the target sequence comprises nucleotides 75 to 1168 of SEQ ID NO: 1, nucleotides 803 to 1168 of SEQ ID NO: 1, nucleotides 61 to 1019 of SEQ ID NO: 3, nucleotides 788 to 1019 of SEQ ID NO: 3, a nucleic acid molecule comprising SEQ ID NO: 5, or nucleotides 127 to 807 of SEQ ID NO: 5.

In some embodiments, the oligonucleotide probe(s), rather than the amplification products, may be optionally fixed to a solid support.

In yet other embodiments, steps (c) to (e) are omitted and the plurality of amplification products are detected by size separation followed by staining with a reagent, such as ethidium bromide, that detects DNA. This embodiment may optionally further comprise photographing the stained DNA to preserve the results. In these embodiments, detection of the amplification products can be used to diagnose or prognose prostate cancer as well.

When detecting ERG isoform expression in a biological sample, the oligonucleotide probe, first oligonucleotide primer, and second oligonucleotide primer, each comprise a nucleic acid sequence that is capable of hybridizing under defined conditions (for example under high stringency hybridization conditions; such as hybridization for 12 hours at 65° C. in 6×SSC followed by a wash in 0.1×SSC at 50° C. for 45 minutes) to a nucleic acid sequence of an ERG isoform. Thus, the oligonucleotide probe, first oligonucleotide primer, and second oligonucleotide primer comprises, for example, a nucleic acid sequence of an ERG isoform, such as SEQ ID NO: 1 (ERG8), SEQ ID NO: 3 (EPC1), SEQ ID NO: 5 (EPC2), a transcript from the prostate cancer-specific promoter (SEQ ID NO: 7) or a nucleic acid molecule comprising a fragment thereof, or a sequence complementary thereto. The oligonucleotide probe, first oligonucleotide primer, or second oligonucleotide primer can be a fragment comprising at least about 15, at least about 20, at least about 30, at least about 40, or at least about 50 contiguous nucleotides of a nucleic acid sequence of ERG8, EPC1, EPC2, or a transcript from the prostate cancer-specific promoter, or a sequence complementary thereto.

In some embodiments, the methods comprise detecting the expression of the ERG8 isoform. In other embodiments, expression of the EPC1 isoform is detected. In yet other embodiments, expression of the EPC2 isoform is detected. While in some embodiments, transcripts from the prostate cancer-specific promoter are detected. In still other embodiments, the methods comprise detecting the ERG8 and EPC1 isoforms in combination, the ERG8 and EPC2 isoforms in combination, the EPC1 and EPC2 isoforms in combination, or the combination of the ERG8, EPC1, and EPC2 isoforms. In other embodiments, the method comprises detecting one or more transcripts from the prostate cancer-specific promoter either alone or in combination with one or more of ERG8, EPC1, or EPC2. In some embodiments, the methods further comprise detecting other prostate cancer-specific markers, such as ERG1, ERG2, PSA, DD3, AMAR, LTF, NPY, SPOCK, CRISP3, PLA2G7, TMEFF2, F5, SMOC, ACPP, TGM4, MSMB, WIF1, OLFM4, PI15, PDGFD, CHGA, CAV1, RLN1, IGFBP7, BGN, FMOD, AGR2, SERPINA3, AZGP1, FAM3B, CD164, or the presence of an TMPRSS-ERG fusion.

Polypeptides encoded by ERG8, EPC1, or EPC2 can also be detected and/or measured in a biological sample. For example, antibodies, optionally labeled, can be used to detect each polypeptide using well known techniques, such as ELISA.

The biological sample can be prostate tissue, blood, serum, plasma, urine, saliva, or prostatic fluid.

In another aspect, the disclosure provides a method of diagnosing or prognosing prostate cancer, comprising:
  (a) measuring the expression level (e.g. mRNA or polypeptide) of ERG8, EPC1, EPC2 or a transcript from the prostate cancer-specific promoter; and (b) correlating the expression level of an ERG isoform with the presence of prostate cancer or a higher predisposition to develop prostate cancer in the subject.

The skilled artisan will understand how to correlate expression levels or patterns of ERG8, EPC1, EPC2, or a transcript from the prostate cancer-specific promoter with the presence of prostate cancer or a higher predisposition to develop prostate cancer. For example, the expression levels can be quantified such that increased or decreased expression levels relative to a control sample or other standardized value or numerical range indicate the presence of prostate cancer or a higher predisposition to develop prostate cancer.

The increased or decreased expression levels may be measured relative to the expression level of ERG8, EPC1, EPC2, or a transcript from the prostate cancer-specific promoter, or the corresponding polypeptide, in normal, matched tissue, such as benign prostate epithelial cells from the same subject. Alternatively, the expression level of ERG8, EPC1, EPC2, or a transcript from the prostate cancer-specific promoter, or the corresponding polypeptide, may be measured relative to the expression of the gene or polypeptide in other noncancerous samples from the subject or in samples obtained from an individual who does not have cancer. Expression of a gene or the corresponding polypeptide may also be normalized by comparing it to the expression of other cancer-specific markers. For example, a prostate specific marker, such as PSA or TMPRSS2-ERG, can be used as a control to compare and/or normalize expression levels of ERG8, EPC1, EPC2, or a transcript from the prostate cancer-specific promoter, or the corresponding polypeptide.

By way of example, the method of diagnosing or prognosing prostate cancer can comprise measuring the expression levels of the ERG8, EPC1, EPC2, or a transcript from the prostate cancer-specific promoter, isoforms, or any combination thereof, and diagnosing or prognosing prostate cancer, where an increased expression level of ERG8, EPC1, or EPC2 of at least 10%, 20%, 30%, 40%, 50%, 60%, 70%, 80%, 90%, 100%, 200%, or more, as compared to the control sample indicates the presence of prostate cancer or a higher predisposition in the subject to develop prostate cancer, or indicates the severity or stage of prostate cancer, such as whether the cancer is a high risk or a moderate risk prostate cancer.

The expression levels of ERG8, EPC1, EPC2, or a transcript from the prostate cancer-specific promoter (e.g., mRNA or polypeptide expression) can be detected according to the methods described herein or using any other known detection methods, including, without limitation, immunohistochemistry, Southern blotting, northern blotting, western blotting, ELISA, and nucleic acid amplification procedures that include but not limited to PCR, transcription-mediated amplification (TMA), nucleic acid sequence-based amplification (NASBA), self-sustained sequence replication (3SR), ligase chain reaction (LCR), strand displacement amplification (SDA), and loop-mediated isothermal amplification (LAMP).

Nucleic acids are also provided for detecting prostate cancer, and one or more of these nucleic acids may optionally be provided as part of a kit. In some embodiments, the nucleic acid is a nucleic acid probe, such as the probes described elsewhere in the disclosure, that hybridizes to a prostate cancer-specific transcript. In one embodiment the nucleic acid probe hybridizes to SEQ ID NO: 1, or to a sequence within nucleotides 75 to 1168 or 801 to 1168 of SEQ ID NO: 1 (ERG8), or to the complement thereof, under defined hybridization conditions. For example, in one embodiment, the probe is capable of hybridizing to the desired sequence under high stringency hybridization conditions, such as hybridization for 12 hours at 65° C. in 6×SSC followed by a wash in 0.1×SSC at 50° C. for 45 minutes. The probe can include SEQ ID NO: 1 itself, or a fragment of SEQ ID NO: 1 comprising at least about 15, 20, 30, 40, 50, 60, 70, 80, 90, 100, 150, or 200 contiguous nucleotides of SEQ ID NO: 1, or a sequence complementary thereto. In one embodiment, the fragment comprises all or part of nucleotides 75 to 1168 of SEQ ID NO: 1. For example, the fragment may comprise nucleotides 801 to 1168 of SEQ ID NO: 1, or a nucleic acid molecule comprising at least about 15, 20, 30, 40, 50, 60, 70, 80, 90, 100, 150, or 200 contiguous nucleotides of nucleotides 801 to 1168 of SEQ ID NO: 1. In some embodiments, the probe selectively hybridizes to the ERG8 isoform but does not hybridize to ERG1, ERG2, ERG3, ERG4, ERG5, ERG6, ERG7, ERG9, EPC1, EPC2, a transcript from the prostate cancer-specific promoter, or TMPRSS2 under defined conditions, including, for example, high stringency hybridization conditions. The length of the probe may vary depending, for example, on the hybridization conditions and the percent identify between the target sequence and the probe, and, therefore can be up to about 6, 10, 20, 30, 40, 50, 100, 150, 200, 300, 400, or 500 nucleotides long.

In some embodiments, therefore, the disclosure provides an isolated nucleic acid comprising at least about 15 contiguous nucleotides of nucleotides 801 to 1168 of SEQ ID NO: 1, wherein the nucleic acid is capable of hybridizing to SEQ ID NO: 1, or the complement thereof, under conditions of high stringency but not to ERG1, ERG2, ERG3, ERG4, ERG5, ERG6, ERG7, ERG9, EPC1, EPC2, a transcript from the prostate cancer-specific promoter, or TMPRSS2. In some embodiments, the nucleic acid is up to about 50 nucleotides long. In other embodiments the probe is capable of hybridizing to the desired sequence under conditions of high stringency comprising hybridization for 12 hours at 65° C. in 6×SSC followed by a wash in 0.1×SSC at 50° C. for 45 minutes.

In another embodiment, the probe hybridizes to SEQ ID NO: 3, or to a sequence within nucleotides 61 to 1019 or 788 to 1068 of SEQ ID NO: 3 (EPC1), or to the complement thereof, under defined hybridization conditions. For example, in one embodiment, the probe is capable of hybridizing to the desired sequence under high stringency hybridization conditions, such as, hybridization for 12 hours at 65° C. in 6×SSC followed by a wash in 0.1×SSC at 50° C. for 45 minutes. The probe can include SEQ ID NO: 3 itself, or a fragment of SEQ ID NO: 3 comprising at least about 15, 20, 30, 40, 50, 60, 70, 80, 90, 100, 150, or 200 contiguous nucleotides of SEQ ID NO: 3, or a sequence complementary thereto. In one embodiment, the fragment comprises all or part of nucleotides 61 to 1019 of SEQ ID NO: 3. For example, the fragment may comprise nucleotides 788 to 1019 of SEQ ID NO: 3, or a nucleic acid molecule comprising at least about 15, 20, 30, 40, 50, 60, 70, 80, 90, 100, 150, or 200 contiguous nucleotides of nucleotides 788 to 1019 of SEQ ID NO: 3. In some embodiments, the probe selectively hybridizes to EPC1 but not to ERG1, ERG2, ERG3, ERG4, ERG5, ERG6, ERG7, ERG8, ERG9, EPC2, a transcript from the prostate cancer-specific promoter, or TMPRSS2 under defined conditions, including, for example, high stringency hybridization conditions. The length of the probe may vary depending, for example, on the hybridization conditions and the percent identify between the target sequence and the probe, and, therefore can be up to about 6, 10, 20, 30, 40, 50, 100, 150, 200, 300, 400, or 500 nucleotides long.

In some embodiments, therefore, the disclosure provides an isolated nucleic acid comprising at least about 15 contiguous nucleotides of nucleotides 788 to 1019 of SEQ ID NO: 3, wherein the nucleic acid is capable of hybridizing to SEQ ID NO: 3, or the complement thereof, under conditions of high stringency but not to ERG1, ERG2, ERG3, ERG4, ERG5, ERG6, ERG7, ERG8, ERG9, EPC2, a transcript from the prostate cancer-specific promoter, or TMPRSS2. In some embodiments, the nucleic acid is up to about 50 nucleotides long. In other embodiments the probe is capable of hybridizing to the desired sequence under conditions of high stringency comprising hybridization for 12 hours at 65° C. in 6×SSC followed by a wash in 0.1×SSC at 50° C. for 45 minutes.

In yet another embodiment, the probe hybridizes to SEQ ID NO: 5 (EPC2) or to nucleotides 127 to 807 of SEQ ID NO: 5, or to the complement thereof, under defined hybridization conditions. For example, in one embodiment, the probe is capable of hybridizing to the desired sequence under high stringency hybridization conditions, such as, hybridization for 12 hours at 65° C. in 6×SSC followed by a wash in 0.1×SSC at 50° C. for 45 minutes. The probe can include SEQ ID NO: 5 itself, or a fragment of SEQ ID NO: 5 comprising at least about 15, 20, 30, 40, 50, 60, 70, 80, 90, 100, 150, or 200 contiguous nucleotides of SEQ ID NO: 5 or a sequence complementary thereto. In one embodiment, the fragment comprises all or part of nucleotides 127 to 807 of SEQ ID NO: 5. For example, the fragment may comprise nucleotides 127 to 807 of SEQ ID NO: 5, or a nucleic acid molecule comprising at least about 15, 20, 30, 40, 50, 60, 70, 80, 90, 100, 150, or 200 contiguous nucleotides of nucleotides 127 to 807 of SEQ ID NO: 5. In some embodiments, the probe selectively hybridizes to EPC2 but not to ERG1, ERG2, ERG3, ERG4, ERG5, ERG6, ERG7, ERG8, ERG9, EPC1, a transcript from the prostate cancer-specific promoter, or TMPRSS2 under defined conditions, including, for example, high stringency hybridization conditions. The length of the probe may vary depending, for example, on the hybridization conditions and the percent identify between the target sequence and the probe, and, therefore can be up to about 6, 10, 20, 30, 40, 50, 100, 150, 200, 300, 400, or 500 nucleotides long.

In some embodiments, therefore, the disclosure provides an isolated nucleic acid, comprising at least about 15 contiguous nucleotides of nucleotides 127 to 807 of SEQ ID NO: 5, wherein the nucleic acid is capable of hybridizing to SEQ ID NO: 5, or the complement thereof, under conditions of high stringency but not to ERG1, ERG2, ERG3, ERG4, ERG5, ERG6, ERG7, ERG8, ERG9, EPC2, a transcript from the prostate cancer-specific promoter, or TMPRSS2. In some embodiments, the nucleic acid is up to about 50 nucleotides long. In other embodiments the probe is capable of hybridizing to the desired sequence under conditions of high stringency comprising hybridization for 12 hours at 65° C. in 6×SSC followed by a wash in 0.1×SSC at 50° C. for 45 minutes.

A nucleic acid probe may be optionally fixed to a solid support.

In other embodiments, the nucleic acid is an oligonucleotide primer. The disclosure provides a number of oligonucleotide primers and primer pairs, such as those described in the examples. In some embodiments, an oligonucleotide primer pair comprise a first oligonucleotide primer and a second oligonucleotide primer, where the first oligonucleotide primer contains a sequence that hybridizes to a first sequence in SEQ ID NO: 1 and the second oligonucleotide primer contains a sequence that hybridizes to a second sequence in a nucleic acid strand complementary to SEQ ID NO: 1, wherein the first sequence does not overlap with the second sequence. The first and second oligonucleotide primers are capable of amplifying a target sequence of interest in ERG8. Thus, in some embodiments the primer pairs amplify a target sequence comprising all or part of nucleotides 75 to 1168 of SEQ ID NO: 1 or all or part of nucleotides 801 to 1168 of SEQ ID NO: 1. In other embodiments, the target sequence comprises a nucleic acid molecule within nucleotides 75 to 1168 of SEQ ID NO: 1 or nucleotides 801 to 1168 of SEQ ID NO: 1. In some embodiments, the primer pair amplify a target sequence that selectively hybridizes to the ERG8 isoform but does not hybridize to ERG1, ERG2, ERG3, ERG4, ERG5, ERG6, ERG7, ERG9, EPC1, EPC2, a transcript from the prostate cancer-specific promoter, or TMPRSS2 under defined conditions, including, for example, high stringency hybridization conditions, such as, hybridization for 12 hours at 65° C. in 6×SSC followed by a wash in 0.1×SSC at 50° C. for 45 minutes.

In yet other embodiments, an oligonucleotide primer pair comprise a first oligonucleotide primer and a second oligonucleotide primer, where the first oligonucleotide primer contains a sequence that hybridizes to a first sequence in SEQ ID NO: 3 and the second oligonucleotide primer contains a sequence that hybridizes to a second sequence in a nucleic acid strand complementary to SEQ ID NO: 3, wherein the first sequence does not overlap with the second sequence. The first and second oligonucleotide primers are capable of amplifying a target sequence of interest in EPC1. Thus, in some embodiments the primer pairs amplify a target sequence comprising all or part of nucleotides 61 to 1019 of SEQ ID NO: 3 or all or part of nucleotides 788 to 1019 of SEQ ID NO: 3. In other embodiments, the target sequence comprises a nucleic acid molecule within nucleotides 61 to 1019 of SEQ ID NO: 3 or nucleotides 788 to 1019 of SEQ ID NO: 3. In some embodiments, the primer pair amplify a target sequence that selectively hybridizes to the EPC1 isoform but do not hybridize to ERG1, ERG2, ERG3, ERG4, ERG5, ERG6, ERG7, ERG8, ERG9, EPC2, a transcript from the prostate cancer-specific promoter, or TMPRSS2 under defined conditions, including, for example, high stringency hybridization conditions, such as, hybridization for 12 hours at 65° C. in 6×SSC followed by a wash in 0.1×SSC at 50° C. for 45 minutes.

In still other embodiments, an oligonucleotide primer pair comprise a first oligonucleotide primer and a second oligonucleotide primer, where the first oligonucleotide primer contains a sequence that hybridizes to a first sequence in SEQ ID NO: 5 and the second oligonucleotide primer contains a sequence that hybridizes to a second sequence in a nucleic acid strand complementary to SEQ ID NO: 5, wherein the first sequence does not overlap with the second sequence. The first and second oligonucleotide primers are capable of amplifying a target sequence of interest in EPC2. Thus, in some embodiments the primer pairs amplify a target sequence comprising all or part of SEQ ID NO: 5 or all or part of nucleotides 127 to 807 of SEQ ID NO: 5. In other embodiments, the target sequence comprises a nucleic acid molecule within SEQ ID NO: 5 or nucleotides 127 to 807 of SEQ ID NO: 5. In some embodiments, the primer pair amplify a target sequence that selectively hybridizes to the EPC2 isoform but do not hybridize to ERG1, ERG2, ERG3, ERG4, ERG5, ERG6, ERG7, ERG8, ERG9, EPC1, a transcript from the prostate cancer-specific promotor, or TMPRSS2 under defined conditions, including, for example, high stringency hybridization conditions, such as, hybridization for 12 hours at 65° C. in 6×SSC followed by a wash in 0.1×SSC at 50° C. for 45 minutes.

The oligonucleotide primers and primer pairs can be provided in kit form. In some embodiments, the kits comprise a pair of oligonucleotide primers that is capable of amplifying a target sequence of interest in ERG8, such as those discussed elsewhere in the disclosure, a pair of oligonucleotide primers that is capable of amplifying a target sequence of interest in EPC1, such as those discussed elsewhere in the disclosure, and/or a pair of oligonucleotide primers that is capable of amplifying a target sequence of interest in EPC2, such as those discussed elsewhere in the disclosure. In this and other embodiments, it is not necessary for the oligonucleotide primers to all have different sequences. For example, it is possible to amplify target sequences that are specific for each of ERG8, EPC1, EPC2, or a transcript from the prostate cancer-specific promoter, by selecting an oligonucleotide primer that hybridizes to a nucleotide sequence, or complement thereof, that is unique to ERG8, an oligonucleotide primer that hybridizes to a nucleotide sequence, or complement thereof, that is unique to EPC1, an oligonucleotide primer that hybridizes to a nucleotide sequence, or complement thereof, that is unique to EPC2, an oligonucleotide primer that hybridizes to a nucleotide sequence, or complement thereof, that is unique to a transcript from the prostate cancer-specific promoter, and an oligonucleotide primer that hybridizes to a nucleotide sequence, or complement thereof, that is shared by ERG8, EPC1, and EPC2. Thus, it is possible to use only four oligonucleotide primers to selectively amplify target sequences in each of ERG8, EPC1, and EPC2. Other combinations of primers can be selected to amplify, for example, ERG8 and EPC1, ERG8 and EPC2, EPC1 and EPC2, or one of more of those isoforms in combination with a transcript from the prostate cancer-specific promoter.

The disclosure additionally describes diagnostic kits comprising an anti-ERG isoform-specific antibody, for example, an anti-ERG8 antibody, an anti-EPC1 antibody, or anti-EPC2 antibody. In one embodiment, the disclosure provides an anti-EPC1 antibody that binds an epitope comprising amino acids 217 to 220 of SEQ ID NO: 4. In another embodiment, the antibody is an anti-EPC2 antibody that binds an epitope within or comprising amino acids 28 to 97 of SEQ ID NO: 6. In either case, the epitope can be a linear epitope or a conformational epitope. In some embodiments, combinations of antibodies can be included in the kit. For example, a kit can comprise an anti-ERG8 and an anti-EPC1 antibody, an anti-ERG8 and an anti-EPC2 antibody, an anti-EPC1 and an anti-EPC2 antibody, or an anti-ERG8, an anti-EPC1, and an anti-EPC2 antibody. The antibodies can be, optionally, detectably labeled. The antibodies can be used in both diagnostic and prognostic applications, as described for the nucleic acid probes and primers.

The nucleic acids, polypeptides, and antibodies for use in diagnosing and prognosing prostate cancer are generally formulated with a pharmaceutically acceptable carrier. When a nucleic acid, polypeptide, or antibody is part of a kit, an agent that reduces or inhibits the growth of microorganisms, such as sodium azide, can optionally be included in the formulation.

IV. Therapeutic Compositions and Methods

The ERG isoform (e.g., ERG8, EPC1, EPC2, a transcript from the prostate cancer-specific promoter, ERG1, ERG2, or ERG3) nucleic acids, the polypeptides they encode, and antibodies to those polypeptides can be combined with a suitable pharmaceutical carrier. The resulting pharmaceutical compositions can be used in various applications, such as diagnostic applications already described, and also in therapeutic applications. When the application is therapeutic, the compositions comprise a therapeutically effective amount of the nucleic acid, polypeptide, or antibody and a pharmaceutically acceptable carrier or excipient. Such a carrier includes, but is not limited to, saline, buffered saline, dextrose, water, glycerol, ethanol, and combinations thereof. The formulation should suit the mode of administration.

In therapeutic applications, the ERG isoform (e.g., ERG8, EPC1, EPC2, a transcript from the prostate cancer-specific promoter, ERG1, ERG2, or ERG3) nucleic acids, polypeptides, compounds used for destabilization, small molecule inhibitors, and antibody compositions will be formulated and dosed in a fashion consistent with good medical practice, taking into account the clinical condition of the individual subject, the site of delivery, the method of administration, the scheduling of administration, and other factors known to practitioners. The effective amount of ERG isoform (e.g., ERG8, EPC1, EPC2, a transcript from the prostate cancer-specific promoter, ERG1, ERG2, or ERG3) nucleic acids, polypeptides, compounds used for destabilization, small molecule inhibitors, and antibody compositions for purposes herein is thus determined by such considerations.

The disclosure also provides pharmaceutical packs or kits comprising one or more containers filled with one or more of the ingredients of the pharmaceutical compositions described. Associated with such container(s) can be a notice in the form prescribed by a governmental agency regulating the manufacture, use or sale of pharmaceuticals or biological products, which notice reflects approval by the agency of manufacture, use or sale for human administration. In addition, the ERG isoform (e.g., ERG8, EPC1, EPC2, a transcript from the prostate cancer-specific promoter, ERG1, ERG2, or ERG3) nucleic acids, polypeptides, compounds used for destabilization, small molecule inhibitors, and antibody compositions may be employed in conjunction with other therapeutic compounds.

The pharmaceutical compositions may be administered in a convenient manner such as by the oral, topical, intravenous, intraperitoneal, intramuscular, subcutaneous, intranasal, or intradermal routes. The pharmaceutical compositions are administered in an amount which is effective for treating and/or prophylaxis of the specific indication. In general, they are administered in an amount of at least about 10 micrograms/kg body weight and in most cases they will be administered in an amount not in excess of about 8 milligrams/kg body weight per day.

In pharmaceutical dosage forms, the disclosed compositions can be administered in the form of their pharmaceutically acceptable salts, or they can also be used alone or in appropriate association, as well as in combination, with other pharmaceutically active compounds. The subject compositions are formulated in accordance to the mode of potential administration. Administration of the agents can be achieved in various ways, including oral, buccal, nasal, rectal, parenteral, intraperitoneal, intradermal, transdermal, subcutaneous, intravenous, intra-arterial, intracardiac, intraventricular, intracranial, intratracheal, and intrathecal administration, etc., or otherwise by implantation or inhalation. Thus, the subject compositions can be formulated into preparations in solid, semi-solid, liquid or gaseous forms, such as tablets, capsules, powders, granules, ointments, solutions, suppositories, enemas, injections, inhalants and aerosols. Methods and excipients mentioned elsewhere in the disclosure are merely exemplary and are in no way limiting.

Compositions for oral administration can form solutions, suspensions, tablets, pills, granules, capsules, sustained release formulations, oral rinses, or powders. For oral preparations, the agents, polynucleotides, and polypeptides can be used alone or in combination with appropriate additives, for example, with conventional additives, such as lactose, mannitol, corn starch, or potato starch; with binders, such as crystalline cellulose, cellulose derivatives, acacia, corn starch, or gelatins; with disintegrators, such as corn starch, potato starch, or sodium carboxymethylcellulose; with lubricants, such as talc or magnesium stearate; and if desired, with diluents, buffering agents, moistening agents, preservatives, and flavoring agents.

The ERG isoform (e.g., ERG8, EPC1, EPC2, a transcript from the prostate cancer-specific promoter, ERG1, ERG2, or ERG3) nucleic acids, polypeptides, compounds used for destabilization, small molecule inhibitors, and antibody compositions can be formulated into preparations for injection by dissolving, suspending, or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Other formulations for oral or parenteral delivery can also be used, as conventional in the art.

The ERG isoform (e.g., ERG8, EPC1, EPC2, a transcript from the prostate cancer-specific promoter, ERG1, ERG2, or ERG3) nucleic acids, polypeptides, compounds used for destabilization, small molecule inhibitors, and antibody compositions can also be introduced into tissues or host cells by other routes, such as viral infection, microinjection, or vesicle fusion. For example, expression vectors can be used to introduce nucleic acid compositions into a cell as described herein. Further, jet injection can be used for intramuscular administration (Furth et al., *Anal. Biochem.* 205:365-368 (1992)). The DNA can be coated onto gold microparticles, and delivered intradermally by a particle bombardment device, or "gene gun" as described in the literature (Tang et al., *Nature* 356:152-154 (1992)), where gold microprojectiles are coated with the DNA, then bombarded into skin cells.

In some embodiments, nucleic acids comprising a sequence encoding an ERG isoform (e.g., ERG8, EPC1, EPC2, a transcript from the prostate cancer-specific promoter, ERG1, ERG2, or ERG3) protein or functional derivative thereof, are administered to promote ERG function, by way of gene therapy. Alternatively, nucleic acids comprising an siRNA, shRNA, or antisense of ERG8, EPC1, EPC2, a transcript from the prostate cancer-specific promoter, ERG1, ERG2, or ERG3 sequence are administered to antagonize ERG expression or function. Any of the methods for gene therapy available in the art can be used. For specific protocols, see Morgan (2001) Gene Therapy Protocols, $2^{nd}$ ed., Humana Press. For general reviews of the methods of gene therapy, see Goldspiel et al. (1993) *Clinical Pharmacy,* 12:488-505; Wu et al. (1991) Biotherapy, 3:87-95; Tolstoshev (1993) *Ann. Rev. Pharmacol. Toxicol.,* 32:573-596; Mulligan (1993) *Science,* 260:926-932; and Morgan et al. (1993) *Ann. Rev. Biochem.,* 62:191-217; May (1993) TIBTECH, 11(5):155-215). Methods commonly known in the art of recombinant DNA technology which can be used are described in Current Protocols in Molecular Biology (2004), Ausubel et al., eds., John Wiley & Sons, NY; and Kriegler (1990) Gene Transfer and Expression, A Laboratory Manual, Stockton Press, NY.

In some embodiments, the therapeutic comprises an ERG isoform, such as ERG8, EPC1, EPC2, a transcript from the prostate cancer-specific promoter, ERG1, ERG2, or ERG3, or an antisense of one or more of these ERG isoforms. The nucleic acid is part of a vector that has a regulatory sequence, such as a promoter, operably linked to the ERG isoform coding region or antisense molecule, said promoter being inducible or constitutive, and, optionally, tissue-specific. In another embodiment, a nucleic acid molecule is used in which an ERG isoform (e.g., ERG8, EPC1, EPC2, a transcript from the prostate cancer-specific promoter, ERG1, ERG2, or ERG3) coding sequence and any other desired sequences are flanked by regions that promote homologous recombination at a desired site in the genome, thus providing for intrachromosomal expression of the ERG isoform (Koller et al. (1989) Proc. Natl. Acad. Sci. U.S.A., 86:8932-8935; Zijlstra et al. (1989) Nature, 342:435-438).

In some embodiments, the nucleic acid to be introduced for purposes of gene therapy comprises an inducible promoter operably linked to the desired nucleic acids, such that expression of the nucleic acid is controllable by the appropriate inducer of transcription.

Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286, which is incorporated herein by reference), or by direct injection of naked DNA, or by use of microparticle bombardment (e.g., a gene gun; Biolistic, DuPont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see, e.g., Wu et al. (1987) J. Biol. Chem., 262:4429-4432). In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell-specific uptake and expression, by targeting a specific receptor (see, e.g., PCT Pubs. WO 92/06180; WO 92/22635; WO92/20316; WO93/14188; WO 93/20221). Alternatively, the nucleic acid can be introduced intracellularly and incorporated within host cell DNA for expression, by homologous recombination (Koller et al. (1989) Proc. Natl. Acad. Sci. U.S.A., 86:8932-8935; Zijistra et al. (1989) Nature, 342:435-438).

In some embodiments, a viral vector that contains an ERG isoform (e.g., ERG8, EPC1, EPC2, a transcript from the prostate cancer-specific promoter, ERG1, ERG2, or ERG3) nucleic acid or antisense nucleic acid is used. For example, a retroviral vector can be used. (Miller et al. (1993) Meth. Enzymol., 217:581-599). These retroviral vectors have been modified to delete retroviral sequences that are not necessary for packaging of the viral genome and integration into host cell DNA. The ERG isoform (e.g., ERG8, EPC1, EPC2, a transcript from the prostate cancer-specific promoter, ERG1, ERG2, or ERG3) nucleic acid to be used in gene therapy is cloned into the vector, which facilitates delivery of the gene into a patient. More detail about retroviral vectors can be found in Boesen et al. (1994) Biotherapy, 6:291-302, which describes the use of a retroviral vector to deliver the MDR1 gene to hematopoietic stem cells in order to make the stem cells more resistant to chemotherapy. Other references illustrating the use of retroviral vectors in gene therapy are: Clowes et al. (1994) J. Clin. Invest., 93:644-651; Kiem et al. (1994) Blood, 83:1467-1473; Salmons et al. (1993) Hum. Gene Ther., 4:129-141; and Grossman et al. (1993) Curr. Opin. Gen. Devel., 3:110-114.

Other viral vectors that can be used in gene therapy include adenoviruses, which are capable of infecting non-dividing cells. Kozarsky et al., Curr. Opin. Gen. Devel., 3:499-503 (1993) present a review of adenovirus-based gene therapy. Bout et al., Hum. Gene Ther., 5:3-10 (1994) demonstrated the use of adenovirus vectors to transfer genes to the respiratory epithelia of rhesus monkeys. Other instances of the use of adenoviruses in gene therapy can be found in Rosenfeld et al., Science, 252:431-434 (1991); Rosenfeld et al., Cell, 68:143-155 (1992); and Mastrangeli et al., J. Clin. Invest., 91:225-234 (1993). Adeno-associated virus (AAV) has also been proposed for use in gene therapy (Walsh et al., Proc. Soc. Exp. Biol. Med., 204:289-300 (1993)).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient. In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler et al., Meth. Enzymol., 217:599-618 (1993); Cohen et al., Meth. Enzymol., 217:618-644 (1993); Cline, Pharmac. Ther., 29:69-92 (1985)) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny. The resulting recombinant cells can be delivered to a patient by various methods known in the art.

The prostate cancer-specific transcripts encode protein products that are thought to either directly or indirectly contribute to the development of the cancerous cell. Accordingly, methods that destabilize these transcripts can be used to reduce or prevent expression of the encoded protein product, thereby preserving the cell in a non-cancerous state, or reverting the cell to a non-cancerous phenotype. In some embodiments, therefore, nucleic acids corresponding to ERG8, EPC1, EPC2, ERG1, ERG2, ERG3, or isoforms encoded by transcripts initiated from a prostate cancer-specific promoter (e.g., SEQ ID NO: 7), or a fragment thereof (such as a fragment comprising at least nucleotides 521 to 650 of SEQ ID NO: 7), are used to interfere with the production or translation of their corresponding transcript. In some cases, the nucleic acid is the complement of the transcript sequence. In these cases, the nucleic acids are therapeutic because they modulate the function of nucleic acids encoding an ERG isoform, such as ERG8, EPC1, EPC2, ERG1, ERG2, ERG3, or isoforms encoded by transcripts initiated from a prostate cancer-specific promoter, and thereby alter expression of the encoded isoform.

One method of modulating the function of one or more ERG isoforms is via RNA interference, for example, using siRNA or shRNA against the ERG isoform. The siRNA is a short double stranded RNA molecule of about 18-25 nucleotides that comprises a nucleotide sequence complementary to a region of the target. It can be introduced into a target cell or tissue, for example using an expression plasmid, where it interferes with the translation of an ERG isoform, such as ERG8, EPC1, EPC2, ERG1, ERG2, ERG3, or isoforms encoded by transcripts initiated from a prostate cancer-specific promoter, such as SEQ ID NO: 7 (or a fragment thereof). RNA interference techniques can be carried out using known methods as described, for example, in published U.S. Patent Applications 20060058255, 20040192626, 20040181821, and 20030148519, each of which is incorporated by reference.

Antisense compounds are another class of nucleic acid that is provided by the disclosure for use in modulating the function of nucleic acid molecules encoding one or more ERG isoforms, thereby modulating the amount of the ERG isoform(s) that is produced. This is accomplished by providing antisense compounds that hybridize with one or more nucleic acids encoding an ERG isoform to a cell, for example, by using a gene therapy technique. The nucleic acid can be DNA encoding an ERG isoform (e.g., ERG8, EPC1, EPC2, ERG1, ERG2, ERG3, or isoforms encoded by transcripts initiated from a prostate cancer-specific promoter, such as SEQ ID NO: 7), RNA (including pre-mRNA and mRNA) transcribed from such DNA, and can also be cDNA derived from such RNA. The hybridization of an antisense compound with its target nucleic acid interferes with the normal function of the nucleic acid. The interference can act at the level of replication or transcription of the DNA, translocation of the RNA to the site of protein translation, translation of protein from the RNA, splicing of the RNA to yield one or more mRNA species, or catalytic activity that may be engaged in or facilitated by the RNA. The overall effect of such interference with target nucleic acid function is the modulation of the expression of an ERG isoform, such as ERG8, EPC1, EPC2, ERG1, ERG2, ERG3, or isoforms encoded by transcripts initiated from a prostate cancer-specific promoter, such as SEQ ID NO: 7 (or a fragment thereof, such as a fragment comprising at least nucleotides 521 to 650 of SEQ ID NO: 7).

Antisense oligonucleotides are one form of antisense compound. These often comprise from about 8 to about 30 nucleobases (i.e. from about 8 to about 30 linked nucleosides). In some embodiments, the antisense oligonucleotide comprises from about 12 to about 25, from about 15 to about 22, or from about 18 to about 20 nucleobases. Antisense oligonucleotides can also comprise modified backbones or non-natural internucleoside linkages. Modified oligonucleotides that do not have a phosphorus atom in their internucleoside backbone are also considered oligonucleotides. Examples of modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonzites, phosphinates, phosphoramidates including 3'-amino phosplioramidate and aminoalkylphosphoramidates, thionophosphoiamidates, thionoalkylphosphonates, thionoalkylphosphotriesters, boranophosphates having normal 3'-5' linkages, 2'-5' linked analogs of these, and those having inverted polarity wherein the adjacent pairs of nucleoside units are linked 3'-5' to 5'-3' or 2'-5' to 5'-2', and backbones formed by morpholino linkages.

Peptide nucleic acid (PNA) compounds are also antisense compounds. In a PNA compound, however, the sugar-backbone of an oligonucleotide is replaced with an aminoethylglycine backbone. The nucleobases are retained and are bound directly or indirectly to aza nitrogen atoms of the amide portion of the backbone.

Antisense compounds, methods for their production, and their use to interfere with nucleic acid function are well known in the art. For example, U.S. Pat. No. 6,054,316, which is incorporated by reference, describes the production of antisense compounds for nucleic acids encoding Ets-2 and methods of using these antisense compounds. These same methods can be applied to the production of antisense compounds for nucleic acids encoding an ERG isoform, such as ERG8, EPC1, EPC2, ERG1, ERG2, ERG3, or isoforms encoded by transcripts initiated from a prostate cancer-specific promoter, such as SEQ ID NO: 7 (or a fragment thereof, such as a fragment comprising at least nucleotides 521 to 650 of SEQ ID NO: 7).

In addition to therapeutic applications related to inhibition of expression of ERG isoforms (e.g., ERG8, EPC1, EPC2, ERG1, ERG2, ERG3, or isoforms encoded by transcripts initiated from a prostate cancer-specific promoter, such as SEQ ID NO: 7), antisense compounds are also useful in diagnostic and prognostic methods because these compounds hybridize to nucleic acids encoding ERG isoforms, which can be detected using art-recognized techniques, such as conjugation of an enzyme to the antisense compound, radiolabelling of the antisense compound, or any other suitable detection methods. Kits comprising the antisense compound and a means for detecting it in a sample can also be prepared as described for kits comprising oligonucleotide probes generally.

Antisense modulation of ERG isoform expression can be assayed in a variety of ways known in the art. For example, mRNA levels can be quantitated by, e.g., northern blot analysis, competitive polymerase chain reaction (PCR), or real-time PCR (RT-PCR). RNA analysis can be performed on total cellular RNA or poly(A)+mRNA. Alternatively or in addition, levels of the encoded protein can be quantitated in a variety of ways well known in the art, such as immunoprecipitation, western blot analysis (immunoblotting), ELISA, or fluorescence-activated cell sorting (FACS).

It is also possible to kill or slow the growth of prostate cancer cells by delivering to those cells a cytotoxic or cytostatic gene product expressed under the control of a prostate cancer-specific promoter, such as the promoter sequence set forth in SEQ ID NO: 7. Truncations and variation of the nucleotide sequence set forth in SEQ ID NO: 7 can also be used, so long as they are sufficient to support expression of an operatively linked reporter gene in prostate cancer cells. Examples include promoter sequences comprising at least nucleotides 521 to 650, 404 to 650, or 138 to 650 of SEQ ID NO: 7. Gene therapy can be used to introduce a vector comprising the prostate cancer-specific promoter operably linked to a nucleic acid encoding the cytotoxic or cytostatic protein into a prostate cancer cell. Such gene therapy methods are described herein. When the prostate cancer-specific promoter is used in the gene therapy vector, however, the promoter is only active in the prostate cancer cells so that the cytotoxic or cytostatic protein is only expressed in the prostate cancer cells, irrespective of the cellular range of the gene therapy vector.

There are many different cytotoxic or cytostatic proteins that can be expressed by placing a heterologous gene under the control of a prostate cancer-specific promoter. Examples of such genes include genes encoding bacterial toxins, such as diphtheria toxin, *pseudomonas* toxin, ricin, cholera toxin, and PE40; tumor suppressor genes, such as APC, CYLD, HIN-1, KRAS2b, p16, p19, p21, p27, p27mt, p53, p57, p73, PTEN, Rb, Uteroglobin, Skp2, BRCA-1, BRCA-2, CHK2, CDKN2A, DCC, DPC4, MADR2/JV18, MEN1, MEN2, MTS1, NF1, NF2, VHL, WRN, WT1, CFTR, C-CAM, CTS-1, zac1, scFV, MMAC1, FCC, MCC, Gene 26 (CACNA2D2), PL6, Beta* (BLU), Luca-1 (HYAL1), Luca-2 (HYAL2), 123F2 (RASSF1), 101F6, and Gene 21 (NPRL2); genes encoding apoptosis-inducing proteins, such as CD95, caspase-3, Bax, Bag-1, CRADD, TSSC3, bax, hid, Bak, MKP-7, PERP, bad, bcl-2, MST1, bbc3, Sax, BIK, BID, and mda7; and genes encoding drug metabolizing enzymes that convert a pro-drug into a cytotoxic product, such as thymidine kinase (from herpes simplex or varicella zoster viruses), cytosine deaminase, nitroreductase, cytochrome p-450 2B1, thymidine phosphorylase, purine nucleoside phosphorylase, alkaline phosphatase, carboxypeptidases A and G2, linamarase, β-lactamase and xanthine oxidase.

Accordingly, the disclosure provides a method for treating prostate cancer comprising administering to a subject in need thereof an expression vector comprising a polynucleotide encoding a cytotoxic or cytostatic gene product operably linked to a promoter sequence comprising SEQ ID NO: 7 or a fragment of the nucleotide sequence set forth in SEQ ID NO: 7 that is sufficient to support expression of an operatively linked reporter gene in prostate cancer cells, including, for example, a sequence comprising at least nucleotides 521 to 650 of SEQ ID NO: 7. In another embodiment, the disclosure provides a method of reducing the growth of a prostate cancer cell comprising administering to the cell an expression vector comprising a polynucleotide encoding a cytotoxic or cytostatic gene product operably linked to a promoter sequence comprising SEQ ID NO: 7 or a fragment of the nucleotide sequence set forth in SEQ ID NO: 7 that is sufficient to support expression of an operatively linked reporter gene in prostate cancer cells, including, for example, a sequence comprising at least nucleotides 521 to 650 of SEQ ID NO: 7. In either embodiment, the cytotoxic or cytostatic gene product is chosen from bacterial toxins, tumor suppressor gene products, apoptosis-inducing proteins, and drug metabolizing enzymes that convert a pro-drug into a cytotoxic product.

Another way to kill a prostate cancer cell or to inhibit or slow its growth is by modulating the activity of proteins within the cell. For example, an antibody that binds a protein encoded by an ERG isoform can be used to inhibit or stimulate the function of that protein. In some embodiments, the antibody binds an epitope that is present in proteins encoded by more than one ERG isoforms. Other embodiments involve an antibody that binds the protein encoded by a particular ERG isoform, such as ERG8, EPC1, EPC2, ERG1, ERG2, ERG3, or an isoform encoded by a transcript initiated from a prostate cancer-specific promoter, such as SEQ ID NO: 7 (or a fragment thereof, such as a fragment comprising at least nucleotides 521 to 650 of SEQ ID NO: 7). Thus, in one embodiment the disclosure provides an antibody that binds an epitope comprising amino acid residues 217 to 220 of SEQ ID NO: 4. In another embodiment, the antibody binds an epitope within or comprising amino acids 28 to 97 of SEQ ID NO: 6. The antibody or combination of antibodies can be expressed intracellularly using gene therapy, as described herein. In another example, the antibody binds an epitope within or comprising amino acid residues 28 to 97 of SEQ ID NO: 6, and it also binds the protein consisting of SEQ ID NO: 6.

These various antibodies can be produced using techniques known in the art. For example, the protein(s) encoded by one or more ERG isoform (e.g., ERG8, EPC1, EPC2, ERG1, ERG2, ERG3, or an isoform encoded by a transcript initiated from a prostate cancer-specific promoter, such as SEQ ID NO: 7) can be used as an immunogen and then one or more antibodies with the desired specificity and functional properties can be selected. Such antibodies include, but are not limited to, polyclonal antibodies, monoclonal antibodies, chimeric antibodies, single chain antibodies, and antibody fragments. The antibodies may be from mice, rats, rabbits, hamsters, goats, llamas, humans, or other species.

Various procedures known in the art can be used for the production of polyclonal antibodies to one or more epitopes of a secreted protein. Rabbits, mice, rats, goats, llamas, etc. can be immunized with the native protein, a synthetic version of the protein, or a derivative (e.g., fragment) of the protein. Various adjuvants may be used to increase the immunological response, depending on the host species. Examples of adjuvants include, but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*.

For the preparation of monoclonal antibodies, any of a number of art-recognized techniques can be utilized. For example, monoclonal antibodies can be produced using the hybridoma technique (e.g., Kohler et al., Nature, 256:495-97 (1975); and as described in Antibodies: A Laboratory Manual, eds. Harlow et al., Cold Spring Harbor Laboratory, 1988; Current Protocols in Immunology, Chpt. 2; eds. Colligan et al., National Institutes of Health, Published by John Wiley & Sons, Inc., 2006). Antibodies can also be produced using recombinant DNA methods (e.g., U.S. Pat. No. 4,816,567) or using phage display antibody libraries (e.g., Clackson et al., Nature, 352: 624-28 (1991); Marks et al., J. Mol. Biol., 222: 581-97 (1991)). If desired, chimeric antibodies can be produced using methods known in the art (e.g., Morrison et al., Proc. Nat'l Acad. Sci. U.S.A., 81:6851-55 (1994); Neuberger et al., Nature, 312:604-08 (1984); Takeda et al., Nature, 314:452-54 (1985)). Single chain antibodies can also be produced (e.g., U.S. Pat. No. 4,946,778). Human antibodies can be prepared using human hybridomas (Cote et al., Proc. Natl. Acad. Sci. U.S.A., 80:2026-30 (1983)), by transforming human B cells with EBV virus in vitro (Cole et al. (1985) Monoclonal Antibodies and Cancer Therapy, Alan R. Liss, pp. 77-96), or by preparing hybridomas from animals transgenic for one or more human immunoglobulin genes (e.g., U.S. Pat. No. 5,939,598). A monoclonal antibody can be readily expressed using its encoding DNA sequence(s), and methods for such expression, including gene therapy methods, are well known in the art.

Antibody fragments can also be generated using known techniques. Fragments include but are not limited to: $F(ab')_2$ fragments, which can be produced by pepsin digestion of the antibody molecule; Fab' fragments, which can be generated by reducing the disulfide bridges of the $F(ab')_2$ fragment; Fab fragments, which can be generated by treating the antibody molecule with papain and a reducing agent; and Fv fragments, including single chain Fv (scFv) fragments.

Following the production of antibodies by, for example, hybridoma technology, screening for the desired antibody can be accomplished by techniques known in the art, e.g., ELISA, and involve no more than routine techniques (e.g., Antibodies: A Laboratory Manual, eds. Harlow et al., Cold Spring Harbor Laboratory, 1988; Current Protocols in Immunology, Chpt. 2; eds. Colligan et al., National Institutes of Health, Published by John Wiley & Sons, Inc., 2006). Thus, an antibody can be selected that binds a linear epitope or a conformational epitope. An antibody also can be selected for the property of binding both to a polypeptide fragment of a larger protein, and to the intact (e.g., full length or wild-type) protein.

When it is necessary to produce an antibody to a protein encoded by an ERG isoform (e.g., ERG8, EPC1, EPC2, ERG1, ERG2, ERG3, or an isoform encoded by a transcript initiated from a prostate cancer-specific promoter, such as SEQ ID NO: 7), the protein, its fragment, or other derivative, can be produced using standard techniques. Methods of manipulating nucleic acids to express proteins are well known in the art, and include those described in Molecular Cloning, A Laboratory Manual (2nd Ed., Sambrook, Fritsch and Maniatis, Cold Spring Harbor) and Current Protocols in Molecular Biology (Eds. Ausubel, Brent, Kingston, More, Feidman, Smith and Stuhl, Greene Publ. Assoc., Wiley-Interscience, NY, N.Y., 1992).

Generally, in order to express the protein encoded by an ERG isoform (e.g., ERG8, EPC1, EPC2, ERG1, ERG2, ERG3, or an isoform encoded by a transcript initiated from a prostate cancer-specific promoter, such as SEQ ID NO: 7), a suitable cell line is transformed with a DNA sequence encoding that protein under the control of known regulatory sequences. The transformed host cells are cultured and the protein recovered and isolated from the culture medium. The isolated expressed proteins are substantially free from other proteins with which they are co-produced as well as from other contaminants. Suitable cells or cell lines may be mammalian cells, such as Chinese hamster ovary cells (CHO), the monkey kidney COS-1 cell line, or mammalian CV-1 cells. The selection of suitable mammalian host cells and methods for transformation, culturing, amplification, screening, product production and purification are known in the art. (See, e.g., Gething and Sambrook, *Nature,* 293:620-625 (1981); Kaufman et al., *Mol Cell Biol.,* 5(7):1750-1759 (1985); Howley et al., U.S. Pat. No. 4,419,446.))

Bacterial cells may also be used as suitable hosts for expression of the secreted proteins. For example, the various strains of *E. coli* (e.g., HB101, MC1061) are well-known as host cells in the field of biotechnology. Various strains of *B. subtilis, Pseudomonas*, other bacilli and the like may also be used. For expression of a protein in bacterial cells, DNA encoding the propeptide is generally not necessary.

Many strains of yeast cells known to those skilled in the art may also be available as host cells for expression of the secreted protein biomarkers. Additionally, where desired, insect cells may be utilized as host cells in the method of the present invention. See, e.g., Miller et al., *Genetic Engineering,* 8:277-298 (Plenum Press 1986).

In some embodiments, the protein encoded by an ERG isoform (e.g., ERG8, EPC1, EPC2, ERG1, ERG2, ERG3, or an isoform encoded by a transcript initiated from a prostate cancer-specific promoter, such as SEQ ID NO: 7) is expressed using a vector that contains a full length DNA sequence encoding the protein and appropriate expression control sequences. Expression control sequences for such vectors are known to those skilled in the art and may be selected depending upon the host cells. Such selection is routine. In other embodiments, the secreted protein biomarker is expressed as a fusion protein comprising the protein sequence of the biomarker and, for example, a tag to stabilize the resulting fusion protein or to simplify purification of the secreted protein biomarker. Such tags are known in the art. Representative examples include sequences which encode a series of histidine residues, the epitope tag FLAG, the Herpes simplex glycoprotein D, beta-galactosidase, maltose binding protein, streptavidin tag or glutathione S-transferase.

In some embodiments, therefore, it is desirable that protein expression of ERG8, EPC1, EPC2, ERG1, ERG2, ERG3, or an isoform encoded by a transcript initiated from a prostate cancer-specific promoter, such as SEQ ID NO: 7, is entirely by an in vitro method. Of course, as already discussed, in other embodiments it is desirable that the protein expression occurs in vivo.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims. Moreover, advantages described in the body of the specification, if not included in the claims, are not per se limitations to the claimed invention.

It is to be understood that both the foregoing general description and the following detailed description are exemplary and explanatory only and are not restrictive of the invention, as claimed. Moreover, it must be understood that the invention is not limited to the particular embodiments described, as such may, of course, vary. Further, the terminology used to describe particular embodiments is not intended to be limiting, since the scope of the present invention will be limited only by its claims. The claims do not encompass embodiments in the public domain.

With respect to ranges of values, the invention encompasses each intervening value between the upper and lower limits of the range to at least a tenth of the lower limit's unit, unless the context clearly indicates otherwise. Further, the invention encompasses any other stated intervening values. Moreover, the invention also encompasses ranges excluding either or both of the upper and lower limits of the range, unless specifically excluded from the stated range.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test the invention. Further, all publications mentioned herein are incorporated by reference in their entireties.

It must be noted that, as used herein and in the appended claims, the singular forms "a," "or," and "the" include plural referents unless the context clearly dictates otherwise. Thus, for example, reference to "a subject polypeptide" includes a plurality of such polypeptides and reference to "the agent" includes reference to one or more agents and equivalents thereof known to those skilled in the art, and so forth.

Further, all numbers expressing quantities of ingredients, reaction conditions, % purity, polypeptide and polynucleotide lengths, and so forth, used in the specification and claims, are modified by the term "about," unless otherwise indicated. Accordingly, the numerical parameters set forth in the specification and claims are approximations that may vary depending upon the desired properties of the present invention. At the very least, and not as an attempt to limit the application of the doctrine of equivalents to the scope of the claims, each numerical parameter should at least be construed in light of the number of reported significant digits, applying ordinary rounding techniques. Nonetheless, the numerical values set forth in the specific examples are reported as precisely as possible. Any numerical value, however, inherently contains certain errors from the standard deviation of its experimental measurement.

The specification is most thoroughly understood in light of the references cited herein. Each of these references is hereby incorporated by the reference in its entirety.

V. ERG Isoform Expression in Prostate Cancer Tissue and Cell Lines

Example 1: ERG8 is Selectively Expressed in Prostate Cancer Tissue

ERG1 is the most commonly overexpressed proto-oncogene in malignant prostatic tissue. (Petrovics et al., (2005) Oncogene 24: 3847-52.) This overexpression may be due to the fusion of the TMPRSS2 gene with the ERG gene. (Tomlins et al., (2005) Science 310: 644-48.) Alternative splicing generates multiple ERG isoforms. (Owczarek et al., (2004) GENE 324: 65-77.) Thus, it is possible that other isoforms of ERG are also overexpressed, or are selectively expressed, in prostate cancer.

In an initial experiment, we sought to detect the ERG8 isoform in cDNA derived from laser microdissected (LCM) prostate tumor cells. The cDNA was amplified using a primer pair from the genomic sequence of exon 1 of the TMPRSS2 gene (primer p2178: 5'-TAGGCGCGAGCTAAGCAGGAG-3'—SEQ ID NO: 8) and from the ERG coding sequence (primer p2220: 5'-CCAGGATGCCTTCTTTGCCCATC-3'—SEQ ID NO: 9). The TMPRSS2 gene is often fused to the ERG gene in prostate cancer. The p2718 primer corresponds to nucleotides 1 to 21 of SEQ ID NO: 1, while p2220 corresponds to the reverse complement of nucleotides 1042 to 1062 of SEQ ID NO: 1. This primer pair resulted in a PCR product and sequencing confirmed it was ERG8.

We then undertook a more thorough examination of the expression ratios of the ERG1, ERG2, ERG3, and ERG8 isoforms in normal prostate cells and in the prostate cancer-derived cell line VCaP. We isolated mRNA from normal prostate of 11 individuals and from prostate cancer-derived VCaP cells, respectively. After converting the mRNA to cDNA, we assessed ERG isoform ratios by comparing the intensities of isoform-specific PCR products in a semi-quantitative multiplex PCR approach. FIG. 1 presents the results of the multiplex PCR analysis. The ERG primers used for the PCR were as follows: p2192 (exon 9): 5'-ACCGTTGGGATGAACTACGGCA-3' (SEQ ID NO: 10, which corresponds to nucleotides 352 to 373 of SEQ ID NO: 1); p2220: (ERG8 specific): 5'-CCAGGATGCCTTCTTTGCCCATC-3' (SEQ ID NO: 11, which corresponds to the reverse complement of nucleotides 1042 to 1064 of SEQ ID NO: 1); p2207: (exon 16): 5'-CCCTCCCAAGAGTCTTTG-GATCTC-3 (SEQ ID NO: 12); p2197: (exon 15): 5'-CCTG-GATTTGCAAGGCGGCTACT-3' (SEQ ID NO: 13); and p2198: (exon 11): 5'-CTCTCCACGGTTAATGCAT-GCTAG-3' (SEQ ID NO: 14, which corresponds to nucleotides 699 to 722 of SEQ ID NO: 1).

Primer pair p2192-p2220 results in a 713 bp PCR product when ERG8 is present. The combination of primers p2192 and p2207 amplifies ~1300 bp products representing ERG isoforms 1, 2 and 3. When p2192 (Exon 9) is paired with primer p2197 (Exon 15), that primer combination amplifies one or more of ERG isoforms 1, 2 and 3. Primer pair p2198-p2220 is also specific to the ERG8 isoform, and this primer pair amplifies a 366 bp PCR product when ERG8 is present. The combination of p2198 (Exon 11) and p2207 (Exon 16) results in a 959 bp product detecting ERG isoforms 1, 2 and 3, while the p2198-p2197 combination yields products of 279 bp (isoform 3) and 207 bp (isoforms 1 and 2).

In FIG. 1, the normal prostate samples are labeled "NP", while samples using the VCaP cells are labeled "VC". ERG8 is the predominant isoform detected in VCaP cells (FIG. 1, right photograph, upper arrow). It is also present at higher levels than ERG1 and ERG2 in normal prostate, but its level in normal prostate is comparable to that of ERG3.

Figure 2:
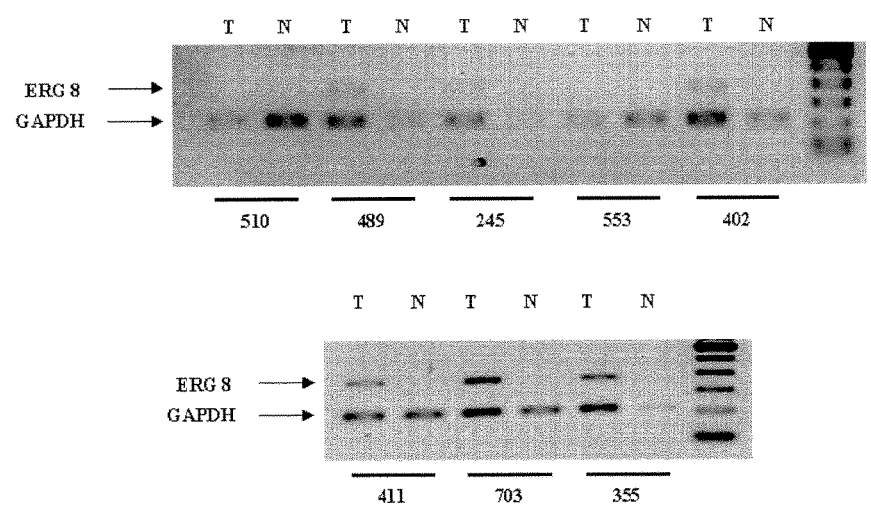
FIG. 2 shows the PCR amplification results for ERG8 transcript expression in tumor cells (T) and benign epithelial cells from eight patients.

We have also assayed the expression of ERG8 transcripts in RNA specimens extracted from laser microdissected (LCM) tumor and benign epithelial cells of 14 individual prostate cancer patients. Primers specifically recognizing the ERG8 isoform (p2198-p2220) were used together with GAPDH primers as internal controls in the same RT-PCR reaction tubes. FIG. 2 shows a photograph of a PCR gel with data for eight of the patients. Tumor cell samples are labeled "T", while the benign epithelial cell samples from each patient are labeled "N". ERG8 expression was detected in the tumor cell samples of 11 of the 14 prostate cancer patients tested. We did not detect ERG8 expression in the benign cells of any patient in this cohort. Thus, ERG8 isoform detection indicates the presence of cells with a cancerous phenotype. In FIG. 2, the level of ERG8 is below the detection limit in the normal samples, which include only epithelial cells. The difference between ERG8 detection in FIG. 1 and FIG. 2, therefore, can be explained by the presence of the other cell types (e.g., stroma and endothelial cells) included in the pooled prostate tissue used for the analysis in FIG. 1.

Interestingly, the ERG8 transcript (SEQ ID NO: 1) is a fusion between TMPRSS2 and ERG8. The open reading frame, however, is entirely encoded by the ERG8 sequence (nucleotides 75 to 1168 of SEQ ID NO: 1). The encoded protein (SEQ ID NO: 2), therefore, does not contain any amino acid sequences from TMPRSS2.

Cancer cells gain growth advantage by activating cell growth promoting genes and by silencing inhibitory genes of cell proliferation. Certain genes in these cell growth or proliferation pathways may produce alternative transcript that counteract the function of natural transcriptional products. In the case of ERG8, the encoded protein product lacks the DNA binding domain of, for example, ERG1 and ERG2, but it retains the entire protein-protein interaction domain. Overexpression of ERG8 in the context of prostate cancer, therefore, likely results in the functional nullification of protein interaction partners of ERG1 and ERG2, resulting in a dominant negative effect. ERG8 could also represent an oncogenic "gain of function" isoform.

The finding that ERG8 is selectively expressed in prostate cancer cells provides a powerful therapeutic option, as this oncogenic ERG8 product can be inhibited by selective targeting through its distinct 3' sequences. This selective targeting for cancer therapy can be accomplished using siRNA, shRNA, and other nucleic acid-based products capable of targeting the ERG8-specific sequence. At the protein level, antibodies and therapeutic agents such as small inhibitory peptides can be used to inhibit the activity of the protein produced by ERG8 or to target that protein for degradation. Moreover, ERG8 can differentiate tumor cells from normal epithelial cells in prostate specimens. Accordingly, detection of ERG8 using, for example, amplification primers or hybridization-based methods, can also be used to diagnose and prognose prostate cancer.

Example 2: EPC1 and EPC2 are Newly Identified Transcripts that are Selectively Expressed in Prostate Cancer Tissue To identify tumor specific ERG transcripts, we pooled prostate tumor tissue samples from six patients and extracted total RNA. Polyadenylated RNA (mRNA) was then isolated, converted into cDNA, and packaged into the Lambda Zap express system (Stratagene) to obtain a bacteriophage library. We screened phage plaques by hybridization of radioactively labeled ERG2 probes. The ERG2 sequence includes exons used by all other ERG isoforms; accordingly, it can be used as a general ERG probe. Hybridization was performed with $1 \times 10^6$ cpm $^{32}$P-radiolabelled human ERG2 cDNA/mL hybridization solution at 65° C. for overnight. Following hybridization, the membranes were washed sequentially with 2×SSC supplemented with 0.1% SDS, then 0.2×SSC supplemented with 0.1% SDS, at 65° C. Before we isolated DNA for sequencing, we subjected hybridization positive clones to two more rounds of plaque screening to obtain single plaques.

Two clones yielded novel ERG isoform transcripts. Each clone has a unique 3' sequence. Because these ERG transcripts have only been observed in prostate cancer tissue, we called the clones "EPC1" and "EPC2" for ERG Prostate Cancer-Specific Isoform 1 and 2.

The nucleic acid sequence of the EPC1 clone is set forth in SEQ ID NO: 3. This transcript is also a fusion between exons of TMPRSS2 and ERG. The TMPRSS2 derived sequence occurs at the 5' end upstream of the initiation methionine (ATG at position 140 to 142 of SEQ ID NO: 3). The last four carboxy-terminal amino acids of the EPC1 amino acid sequence (SEQ ID NO: 4) are not found in any ERG exon, and they appear to be derived from an ERG intronic sequence. The unique 3' end of EPC1 corresponds to nucleotides 788 to 1019 of SEQ ID NO: 3 and can be used in both nucleic acid (e.g., amplification and hybridization-based) and protein (e.g., antibody-based) detection methods for the detection of cancer cells or precancerous cells in specimens and biofluids.

The nucleic acid sequence of the EPC2 clone is set forth in SEQ ID NO: 5. The amino acid sequence of EPC2 is set forth in SEQ ID NO: 6. The unique 3' sequence corresponds to nucleotides 127 to 807 of SEQ ID NO: 5. The 5' end corresponds to sequences within ERG exon 10, and the sequence appears to continue into the adjacent 3' exon without splicing, resulting in a unique transcript sequence.

We next investigated the expression of EPC1 transcripts in RNA specimens extracted from laser microdissected (LCM) tumor and benign epithelial cells of 14 prostate cancer patients using RT-PCR. We selected primers specifically recognizing the EPC1 isoform (p2301-p2302) and used them together with GAPDH primers (p2135-p2144) as internal controls in the same reaction tubes. The EPC1 primer sequences were: p2302: 5'-CAGAAAGCAGCCTTC-CCTTA-3' (SEQ ID NO: 15, corresponding to nucleotides 820 to 839 of SEQ ID NO: 3); and p2301: 5'-TTGATAATA-GAGCATCAGACTTCCA-3 (SEQ ID NO: 16, corresponding to the reverse complement of nucleotides 953 to 977 of SEQ ID NO: 3).

Figure 3:
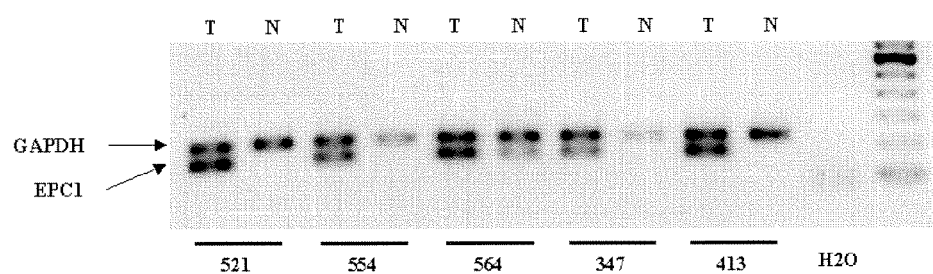
FIG. 3 shows the PCR amplification results for EPC1 transcript expression in tumor cells (T) and benign epithelial cells from five patients.

FIG. 3 shows a photograph of a PCR gel with data for 5 of the 14 patients. Tumor cell samples are labeled "T", while the benign epithelial cell samples from each patient are labeled "N". EPC1 expression was measured, along with the control gene GAPDH. EPC1 expression detected in the tumor cells of 11 of the 14 prostate cancer patients tested. In 7 patients, EPC1 expression could be detected only in their prostate tumor cells, while in four patients, EPC1 expression could be detected in both their tumor and benign epithelial cells. In those instance where EPC1 was detected in both tumor and benign epithelial cells, EPC1 expression was increased in tumor cells relative to benign epithelial cells.

EPC1 and EPC2 are ERG isoforms that are uniquely expressed in cancerous prostate. At the transcript level, the 3' end of each transcript is unique and distinct from all known ERG isoforms. It may be therapeutically beneficial to degrade EPC1 and/or EPC2 mRNA (e.g., using siRNA or shRNA) or to inhibit the EPC1 and/or EPC2 protein by using antibodies raised against each distinct C-terminal region.

Example 3: The ERG8 and EPC1 Isoforms are Abundantly Expressed

Figure 4A:
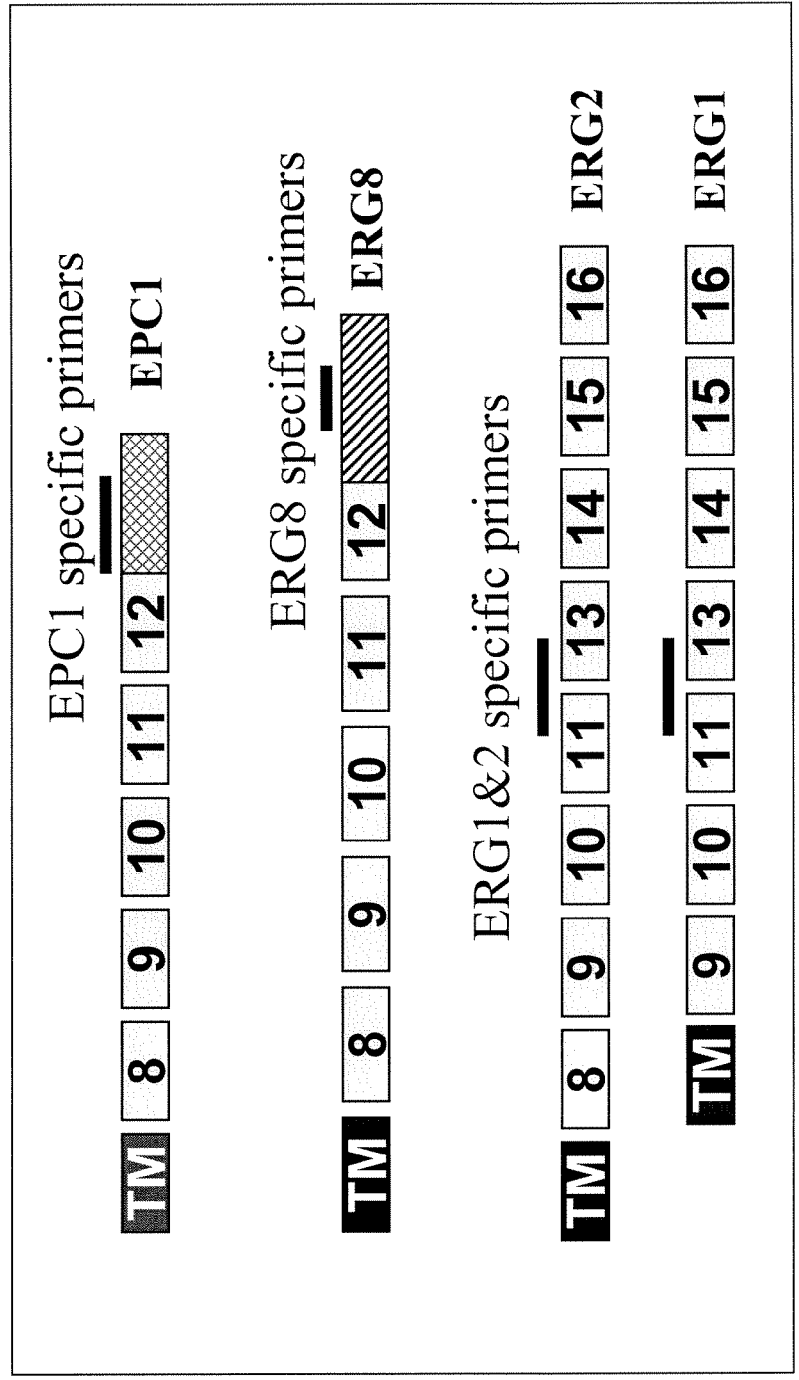
FIG. 4A presents a schematic diagram of the primer positions for EPC1, ERG8, and ERG1/2 specific primers.

In order to compare the relative abundance of ERG8 and EPC1 isoforms to that of ERG1, we prepared samples from prostate cancer-derived VCaP cells as well as from microdissected tumor cells from prostate cancer patients. We then used quantitative PCR to determine the copy numbers using primer pairs specific for EPC1, ERG8, and for a sequence in common between ERG1 and ERG2. The positions of the various primers and the domain structure of the ERG isoforms are shown in FIG. 4A. In the schematic diagram, "TM" denotes TMPRSS2 and the boxes numbered 8-16 correspond to exons, numbered according to Owczarek et al., (2004) GENE 324: 65-77). The ERG8 specific primers and probe were as follows:

```
ERG8 forward primer:
                                    (SEQ ID NO: 17)
TTCAGAAAGACAGATGGGCAAA;

ERG8 reverse primer:
                                    (SEQ ID NO: 18)
GTTCAAAAGTCGGCCTATTCCTAA;

ERG8 probe:
                                    (SEQ ID NO: 19)
AAGGCATCCTGGATGCCTGGCA;

EPC1 forward primer:
                                    (SEQ ID NO: 20)
GCACTTCTGCCAAGCATATGAGT;

EPC1 reverse primer:
                                    (SEQ ID NO: 21)
CGCTGATCATTTCAACACCCT;

EPC1 probe:
                                    (SEQ ID NO: 22)
TGCCTTGAAGATCAAAGTCAAAGAGAAATGGA;

ERG1/2 Ex 11-13 forward primer:
                                    (SEQ ID NO: 23)
TTCAGATGATGTTGATAAAGCCTTACA;

ERG1/2 Ex11-13 reverse primer:
                                    (SEQ ID NO: 24)
TCCAGGCTGATCTCCTGGG;

ERG1/2 Ex 11-13 probe:
                                    (SEQ ID NO: 25)
ATGCATGCTAGAAACACAGATTTACCAT.
```

Figure 4B:
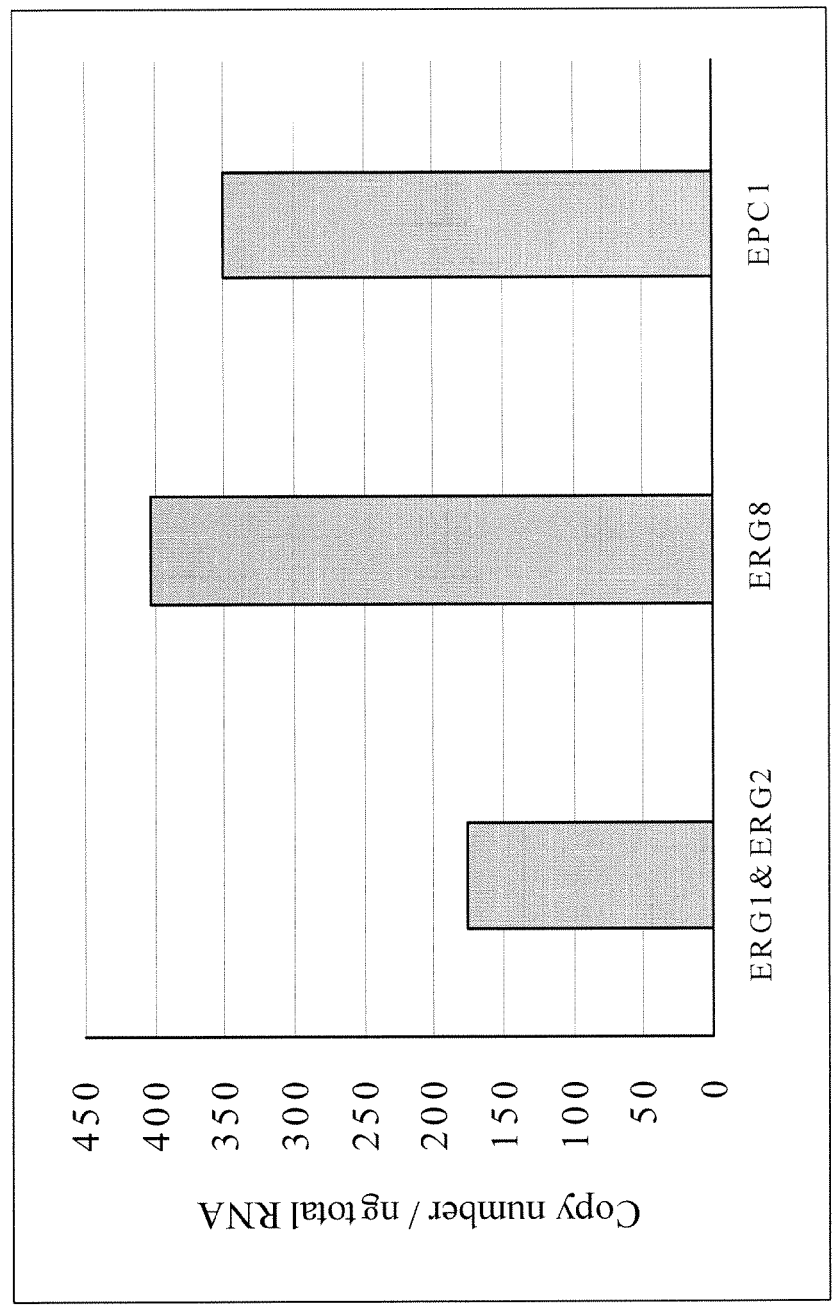
FIG. 4B presents the copy numbers of ERG1/2, ERG8, and EPC1 in VCaP cells.

The number of copies of different ERG isoforms was determined n VCaP cells by TaqMan QRT-PCR using the specific primers and probes shown in FIG. 4A and the results are shown in FIG. 4B. Plasmid constructs comprising a target gene (different ERG isoforms) insert were used to generate standard dilution series in which the copy number of plasmids in the dilution series is known. A formula was derived from the standard curve to correlate the Ct value with the target gene copy number. Using this formula and the standard curve, we calculated the copy numbers of the target genes in the samples.

Figure 4C:
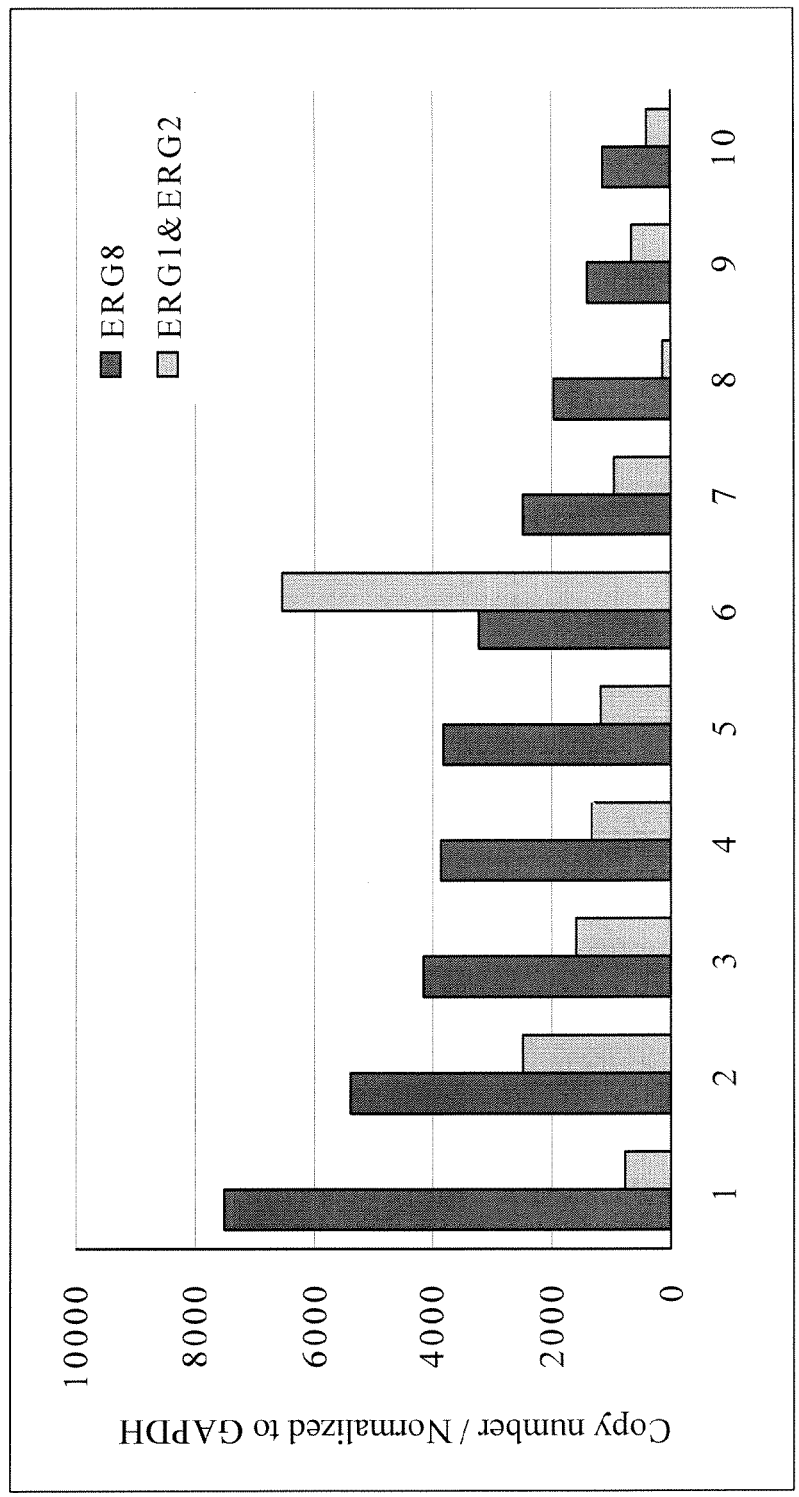
FIG. 4C presents the copy numbers of ERG8 and ERG1/2 using microdissected tumor cells of nine of ten prostate cancer patients.

As shown in FIG. 4B, the copy number of both ERG8 and EPC1 is two-fold or more greater than for the copy number of the combination of ERG1 and ERG2 in VCaP cells. In addition, microdissected tumor cells of nine of ten prostate cancer patients exhibited a higher copy number for ERG8 than for the ERG1 and ERG2 combination (FIG. 4C). These data indicate that the ERG8 and EPC1 isoforms are abundantly expressed and accordingly provide potential targets in diagnostic and prognostic applications.

Example 4: Combined Detection of ERG8 and EPC1 is Inclusive of all TMPRSS2-ERG Fusions Examined and Results in a Robust Detection System for Prostate Cancer Our finding that ERG8 is overexpressed in prostate cancer and that EPC1 is selectively expressed in prostate cancer tissue can be used to develop a particularly robust diagnostic and prognostic assays because these two genes possess unique 3' ends. The 3' end of an mRNA transcript is relatively resistant to degradation compared to its 5' end, making it possible to detect sequences near the 3' end in clinical samples that might be difficult to detect if they were located toward the 5' end of the sequence. Thus, although one mechanism of over- or selective expression of ERG8, EPC1, and EPC2 may involve a 5' fusion to TMPRSS2, the 3' portion of the ERG8, EPC1, and EPC2 sequences should be more stable and readily detectable in clinical samples than the 5' TMPRSS2 sequence. As a result, detecting the 3' end of ERG8, EPC1, and EPC2 transcripts can reduce false negatives compared to detecting 5' sequences such as the 5' TMPRSS2 sequence in TMPRSS2-ERG fusion transcripts. In addition, biofluids, such as urine, serum, plasma, saliva, and prostatic fluid that are easier and cheaper to obtain but more prone to mRNA degradation, can be used to detect 3' sequences of ERG8, EPC1, and EPC2.

Accordingly, we developed a simple PCR assay that detects aberrant expression due to any type of ERG fusion event. We tested an assay that utilizes three pairs of PCR primers. Namely, we used p2302 (SEQ ID NO: 15) and p2301 (SEQ ID NO: 16) to detect EPC1; p2220 (SEQ ID NO: 11) and p2198 (SEQ ID NO: 14) to detect ERG8; and p2236 and p2237, described in Petrovics et al., (2005) Oncogene 24: 3847-3852, to detect the 3' UTR of ERG1/2.

These primer combinations detect sequences in the 3' end that are retained following any 5' fusion, such as with TMPRSS2, and that are relatively resistant to degradation.

We used these three primer pairs to test the presence or absence of ERG isoforms in LCM selected prostate cancer cells. We divided the samples into two groups, based upon whether we could detect a TMPRSS2-ERG fusion transcript. Table 1 presents the results.

By using this combined signal approach, we could detect an amplification product in all samples bearing an ERG fusion. In addition, in those samples in which EPC1 was detected but ERG8 was not (e.g., FP480), we still obtained a combined signal. Although we examined ERG1 expression in several samples to validate the assay, the results show that it is not necessary to include ERG1 in the analysis. Instead, the combined signal from EPC1 and ERG8 was all that was

TABLE 1

| FP | ERGfusionA | ERGfusionA | EPC1 | ERG8 | ERG1 | Combined signal |
|---|---|---|---|---|---|---|
| FP347 | 0.865 | Yes | T | T |  | YES |
| FP411 | 8.07 | Yes | T | T |  | YES |
| FP413 | 2.52 | Yes | T | T |  | YES |
| FP473 | 5.105 | Yes | T | T | T | YES |
| FP480 | 12.005 | Yes | T | no |  | YES |
| FP519 | 1.44 | Yes | T | T |  | YES |
| FP521 | 1.07 | Yes | T | T | T | YES |
| FP554 | 3.9 | Yes | T | no |  | YES |
| FP564 | 2.24 | Yes | T and N | T |  | YES |
| FP703 | 2.66 | Yes | T and N | T |  | YES |
| FP245 | −3.305 | Yes | T and N | T |  | YES |
| FP349 | 1.315 | Yes | T | T |  | YES |
| FP355 | 2.12 | Yes | T | T | T | YES |
| FP391 | 2.16 | Yes | T | T |  | YES |
| FP402 | 3.595 | Yes | T | T | T (and N) | YES |
| FP430 | 2.77 | Yes | T | T |  | YES |
| FP441 | 6.2 | Yes | T and N | no |  | YES |
| FP489 | 3.6 | Yes | T | T |  | YES |
| FP504 | 5.435 | Yes |  | T |  | YES |
| FP510 | 4.47 | Yes | T | no |  | YES |
| FP553 | 2.94 | Yes | T | no |  | YES |
| FP320 |  | No | no | no |  |  |
| FP326 |  | No | no | no |  |  |
| FP346 |  | No | no | no |  |  |
| FP393 |  | No | no | no |  |  |
| FP513 |  | No | no | no |  |  |
| FP535 |  | No | no | no |  |  |
| FP573 |  | No | no | no |  |  |
| FP590 |  | No | no | no |  |  |
| FP598 |  | No | no | no |  |  |
| FP620 |  | No | no | no |  |  |
| FP257 |  | No | T and N | no |  | YES |
| FP260 |  | No | no | no |  |  |
| FP318 |  | No |  | no |  |  |
| FP394 |  | No | no | no |  |  |
| FP446 |  | No | no | no |  |  |
| FP488 |  | No, has fusionC | T and N | T |  | YES |
| FP491 |  | No | no | no |  |  |
| FP493 |  | No | no |  |  |  |
| FP495 |  | No | no | no |  |  |
| FP508 |  | No | no |  |  |  |
| FP523 |  | No | no | no |  |  |
| FP575 |  | No, has fusionC | T | T |  | YES |

In Table 1, the "FP" numbers in the left column are the coded specimen numbers. The first 21 samples presented are those in which we could detect the "A type" TMPRSS2-ERG fusion transcript. ERG fusion A is the most frequent fusion (95% of all fusion transcripts) and involves fusion of the first exon of TMRPSS2 to ERG exon 8. The numeric values in the first column labeled "ERGfusionA" indicate the threshold cycle numbers, normalized to GAPDH, in a quantitative RT-PCR analysis. In 22 samples, we were unable to detect ERG fusion A, but in two samples, FP488 and FP575, we detected ERG fusion C. Fusion "C" is a rare fusion between TMPRSS2 exon 1 and ERG exon 9. In the EPC1, ERG8, and ERG1 columns, "T" indicates detection in tumor cells, "N" indicates detection in normal epithelial cells, and "no" indicates that no signal was detected. The "combined signal" column summarizes the cumulative detection of ERG products ("YES"=expression of any of isoforms EPC1, ERG8, or ERG1).

needed to detect all fusion events. Accordingly, the combined signal approach can help to minimize false negatives that could arise by looking only at a particular ERG transcript. In addition, we expect that the combined approach can be readily used in clinical samples, such as biofluids, that would be inappropriate for use with primers for the more 5' TMPRSS2-ERG fusion event.

Example 5: A Novel ERG Promoter is Activated in Prostate Cancer

To determine whether there are additional alterations that occur in the ERG locus in prostate cancer, we systematically evaluated transcription initiation sites within the ERG locus using the 5' oligocapping method. This information was used to map cancer-specific ERG alternative transcription start sites. We isolated total RNA from prostate cancer tissues of six patients with verified ERG gene rearrangements, pooled the RNA, then treated it with dephosphatases to degrade non-capped RNA molecules, thereby enriching 5' cap protected mRNA molecules. An RNA oligonucleotide adapter was ligated to substitute the 5' capping structure and cDNA was generated by reverse transcription. We then used the oligocap adaptor and internal primers from ERG exon 10 to amplify 5' ERG sequences. In the first amplification we used ERG primer p2181: 5'-GGCGTTGTAGCTGGGGGT-GAG-3' (SEQ ID NO: 26). In the second amplification, we used ERG primer p2268: 5'-CAATGAATTCGTCTG-TACTCCATAGCGTAGGA-3' (SEQ ID NO: 27). The resulting PCR products were cloned into the pUC19 vector, then sequenced. DNA sequences indicating transcription initiation sites from ERG sequences in tumor tissue were matched to the ERG locus and analyzed by generating a score that represented the frequency of individual transcription start sites within the locus. The 5' capping frequency map (CapMap) of ERG gene transcripts is shown in FIG. 5. Of the 152 clones sequenced, 137 of the 5' capping clones had novel, prostate cancer-specific transcription initiation sites within a 23 bp ERG exon 9 region.

In a separate oligocapping experiment, 5' cap sites were assessed in RNA from normal prostates pooled from 11 individuals (AMBION) with negative prostate cancer diagnosis. In this experiment, we terminated our analysis after 30 clones because the products were homogenous. The results indicated that transcription initiation in normal prostate uniformly occurs in ERG exon 5, in sharp contrast to the multiple exon 9 initiation sites we observed in the tumor specimens. Transcription initiation in ERG exon 5 indicates that ERG isoform 3 is expressed in normal prostate. Also, our results suggest that ERG isoforms 1, 2, 5, 6, 7, 8 and 9 are either not expressed in normal prostate, or they are present only at low levels.

The transcription initiation sites detected in the prostate cancer samples indicated that the central segment of ERG exon 9 is a cancer-specific promoter site. The promoter region is defined as the area between −520 bp and +130 bp relative to the most 3' transcription initiation site detected in the mapping experiment. The promoter sequence is set forth below:

(SEQ ID NO: 7). In the sequence, the most 3' transcription start site that is frequently used is bolded and boxed.

Figure 6:
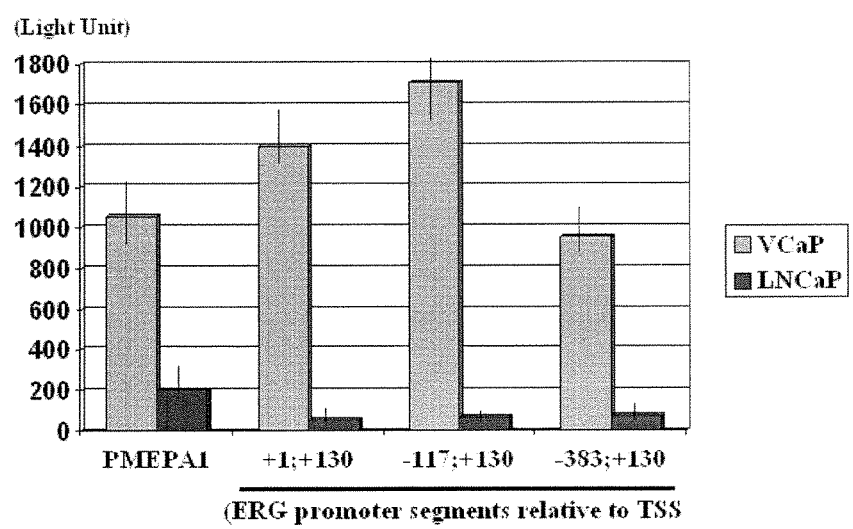
FIG. 6 plots the ability of three segments of the prostate cancer-specific ERG promoter to support expression of a luciferase report construct in the VCaP cell line in comparison to the LNCaP cell line.

The putative TATA-less promoter is predicted at −20; −40 bp from the transcription initiation site. Interestingly, there is also a MED (Multiple Elements of Initiation Downstream) in the +130 region, which may explain the multiple start sites we observed. We have verified that this promoter is functional by operably linking it to the luciferase reporter gene. FIG. 6 demonstrates that the prostate cancer-specific promoter is able to direct expression of luciferase protein in prostate cancer-derived VCaP cells (light grey bars), which contain a TMPRSS2-ERG fusion, but not in LNCaP cells (dark grey bars). A promoter fragment from −117 to +130 (nucleotides 404 to 650 of SEQ ID NO: 7) yielded the greatest expression levels in the luciferase assay, followed by the +1 to +130 fragment (nucleotides 521 to 650 of SEQ ID NO: 7), then the −383 to +130 fragment (nucleotides 138 to 650 of SEQ ID NO: 7).

Activation of a dormant promoter within the ERG gene locus in a cancer specific manner produces transcripts coding for N-terminal deletion mutants. The encoded protein products lack the protein-protein interaction domain of wild type ERG. Therefore, expression products of this dormant promoter may act as dominant negative or gain-of-function molecules. Nucleic acid or protein-based products that manipulate the activity of this promoter can therefore be used for prostate cancer therapy. In addition, the prostate-specific expression of this promoter means that expression vectors in which the promoter is operably linked to a gene encoding a toxin or other inhibitor of cell growth can be used to selectively express the encoded protein in prostate cancer cells.

Example 6: A Regulatory Loop Exists Between ERG and the Androgen Receptor

Gene rearrangements involving the fusion of the androgen receptor-regulated TMPRSS2 gene promoter and ERG occur at a high frequency (~60%) in prostate cancer and are likely to be a direct cause of prostate cell transformation, but the mechanism by which the genomic alteration leads to prostate cancer is thus far unexplained. It is likely that this

```
TCTGTCGCCA GTCTGGAGTG CAGTGGCATG ATCTCAGCTC ACTGCAACCT      50

CCACCTCCCG GATTCAAGCA ATTTTCCTGC CTCAGCCTCC TGAGTAGCTG     100

GGACTACAGG CATGCCCAGC TAATTTTTGT ATTTTTAGTA GAGACGGGGT     150

TTCACCATGT TGGCCAGGAT GGTCTGGATC TCTTGACCTC ATGATCCGCC     200

CACCTCGGCA TCCCAAAGTG TTGGGACTAC AGGCATGAGC CACGGCACCC     250

CGCCTGTATT TGGCTTTTCA CACTTGTCCT TTCTCCCCCA GTCTCTTCCG     300

CCTTGCCCTT CTTTGGTTCT CTCTGTGTAT TGTGAGAAGT CGATGGAGAC     350

ATGCTCTTTG ATTGCTGTTA TAATGGAAGA ATATTTCTTC TCCTCCAGGA     400

ACTCTCCTGA TGAATGCAGT GTGGCCAAAG GCGGGAAGAT GGTGGGCAGC     450

CCAGACACCG TTGGGATGAA CTACGGCAGC TACATGGAGG AGAAGCACAT     500

GCCACCCCCA AACATGACCA CGAACGAGCG CAGAGTTATC GTGCCAGCAG     550

GTCAGGTGCC CACAGCTTCA CTGCCCTCGG CAGATCGCAA CTTCCCCAAG     600

GCTAGGCTGA GCCTCAGGGA GCTCTTCTCC CCCACCTGTG GCATTGATCA     650
``` genomic alteration is responsible for, or at least contributes to, the overexpression of ERG1 in prostate cancer. It is also known that androgen receptor function is central to the growth and differentiation of the normal prostate gland. Further, androgen receptor dysfunction favors the growth and survival of prostate cancer cells and appears to play a role in prostate cancer progression. It is unclear, however, how these alterations interact to result in prostate cancer.

To investigate whether ERG protein contributes to prostate cancer by interfering with androgen receptor signaling, we correlated the expression of TMPRSS2-ERG fusion transcripts with ERG1, androgen receptor (AR), PSA, and the androgen-regulated gene PMEPA1. LTF was also analyzed as a negative control. The results of this analysis are shown in FIG. 7, which compares the quantitative RT-PCR data for the TMPRSS2-ERG fusion to quantitative RT-PCR data obtained by amplifying the 3' untranslated regions of ERG ("ERG1").

We next investigated the effect of ERG expression on transcriptional targets of the androgen receptor. We introduced two different ERG siRNAs into the VCaP prostate cancer cell line. The sequence of the siRNAs is: siRNA-1 (p2094): TGATGTTGATAAAGCCTTA (SEQ ID NO: 28), which targets exon 11, and siRNA-2 (p2095): CGACATC-CTTCTCTCACAT (SEQ ID NO: 29), which targets exon 10. VCaP cells possess a TMPRSS2-ERG fusion and overexpress ERG. The results of these experiment are shown in FIG. 8. Introduction of either siRNA led to the up regulation of NKX3.1 and PSA/KLK3 (FIG. 8A). The upregulation of PSA/KLK3 could also be detected as increased PSA levels in the VCaP culture supernatant (FIG. 8B).

Figure 9:
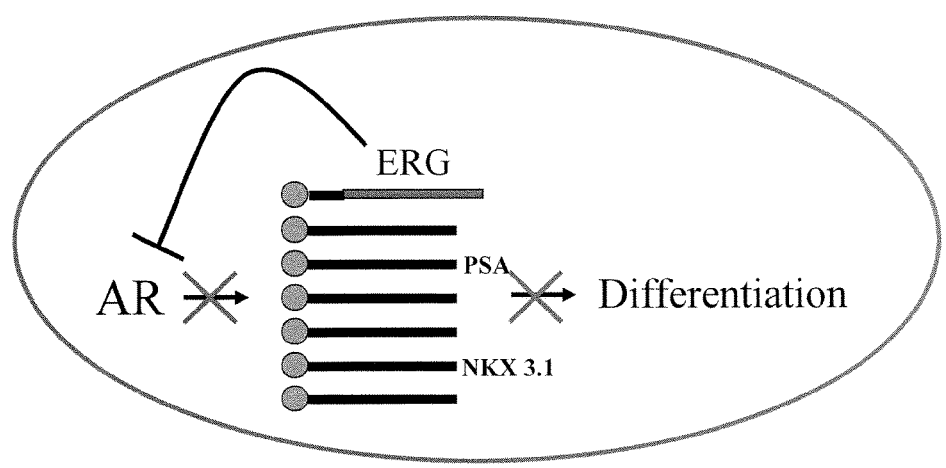
FIG. 9 is an illustration showing that ERG expression can result in inhibition of the androgen receptor responsive genes PSA and NKX3.1, thereby inhibiting cellular differentiation.

Thus, there is a relationship between the in vivo expression of TMPRSS2-ERG or ERG and the expression of other androgen-regulated genes, such as PSA/KLK3 and NKX3.1. Because downregulation of ERG expression correlates with increased expression of NKX3.1 and PSA/KLK3, this indicates that these androgen-regulated genes are downregulated by ectopic ERG expression. NKX3.1 is a tumor suppressor gene and also a transcriptional target of the androgen receptor. Suppression of NKX3.1 by ERG overexpression in prostate cancer cells may therefore interfere with androgen receptor-mediated cell differentiation and negative regulation of cell growth. A schematic of this model is shown in FIG. 9.

As an example of an application for the use of inhibitory molecules in targeting transcripts of the ERG locus for degradation, we used siRNA-1 to inhibit ERG expression in VCaP prostate cancer cells. As noted, siRNA-1 targets exon 11, which is found in ERG1, ERG2, ERG3, ERG8, EPC1, and EPC2 transcripts and in the predicted products of the alternative internal promoter. VCaP cells respond to androgen hormone treatment, therefore, the effect of ERG inhibition on cell growth can be tested by stimulating the cells with androgen hormone.

To perform the siRNA inhibition, cells were first plated to 30% confluence in 100 mm cell culture dishes. Growth was synchronized by incubating the cells in hormone depleted serum (cFBS) containing media for three days. Then the cells were transfected with siRNA-1 and non-targeting (NT) control siRNA using the lipofectamine 2000 reagent (Invitrogen, Carlsbad, Calif.). After transfection 0.1 nM of R1881 synthetic androgen was added to the media. The cells were incubated for 9 days, with a media change every 3 days. Cell cultures were then photographed and 100× magnification of representative view fields were captured.

A microscopic view of VCaP cells is shown in FIG. 10. Cells treated with the control NT siRNA are shown in FIG. 10A, while FIG. 10B shows cells treated with siRNA-1. VCaP cells treated with siRNA-1 exhibited a robust reduction in cell numbers. In addition, striking changes in cell morphology were also apparent. Thus, we were able to show that siRNA-1 treatment inhibited androgen-stimulated growth of VCaP cells.

Taken together, these data suggest that there is a regulatory loop between ERG and the androgen receptor and that negative regulation of the androgen receptor by ERG may contribute to prostate tumorigenesis. Accordingly, there are several therapeutic interventions that can be applied in an early stage prostate cancer (such as well to moderately differentiated tumors) harboring a TMPRSS2-ERG fusion or ERG overexpression. For example, ERG-siRNA, shRNA, or other small molecules can be used to reduce ERG expression in early stage prostate cancer, which is the most common stage of prostate cancer identified in post-PSA screening era. Alternatively or in addition, the androgen receptor can be selectively inhibited with beneficial effects.

It should be again noted that in the context of therapeutic interventions, any mention of "ERG" includes not only ERG8, EPC1, ECP2, and transcript products from the prostate cancer-specific promoter described herein, but also ERG1, ERG2, and ERG3, as well as their combinations, unless specifically indicated to the contrary by context or by an explicit exclusion of one or more of those isoforms. Thus, although we have exemplified inhibition of androgen-stimulated growth with an siRNA specific for exon 11, which is shared by ERG1, ERG2, ERG3, ERG8, EPC1 and EPC2 transcripts, siRNA, shRNA, or other small molecule inhibitors targeted to only one, or any combination of more than one, of those isoforms may also be employed. Such siRNA, shRNA, or other inhibitors that are specific for only one of ERG1, ERG2, ERG3, ERG8, EPC1, EPC2, or a transcript product from the prostate cancer-specific promoter, or that inhibit combinations of those isoforms, can be designed using the sequence data provided elsewhere in the Examples and may include the various primer and probe sequences mentioned.

Progressive tumors that do not express ERG, or express ERG only at low levels, reflect an escape from an intact androgen receptor signaling network. These tumors may be treated by selective upregulation of androgen-regulated genes (e.g., tumor suppressors or cell differentiation and growth inhibitors, such as NKX3.1 and PMEPA1), so as to restore the protective component of the feedback regulation between ERG and the androgen receptor.

VI. Androgen Receptor Function Index

The readout of androgen receptor ("AR") regulated genes ultimately reflects the status of in vivo AR function (ARF) in primary prostate cancer tissue, and consequently carries important information regarding prognosis and rational therapeutic decision making. Assessing the status of AR function in prostate cancer samples can provide early warning signs of androgen independence. (van Gils et al., *Eur Urol.* 48(6):1031-41 (2005).) Well characterized, annotated, and preserved human tissues (with long term follow-up data) from the CPDR Biospecimen Bank were used in high throughput screens to identify and validate prostate cancer biomarker genes.

In recent years, we have analyzed cell type specific gene expression from microdissected matched tumor and benign prostate epithelial cells. We found a general decrease in androgen regulated gene expression with prostate cancer progression. (Petrovics et al., *Oncogene* 24:3847-52 (2005)

.) Others have also recently noted a signature of attenuated AR function in late stage, especially in metastatic prostate cancer in human specimens (Tomlins et al., *Nat Genet.* 39(1): 41-51 (2007)), as well as in a xenograft model system (Hendriksen et al., *Cancer Res.* 66(10):5012-20 (2006)). As part of a 12-gene panel, PSA was found to be underexpressed in aggressive prostate cancer. (Bismar et al., *Neoplasia* 8(1):59-68 (2006).) It should be noted, however, that several laboratories reported high AR expression, amplification, or activity in late stage metastatic prostate cancer. (Heinlein et al., *Endocrine Rev* 25:276-308 (2004); Chen et al., *Nat Med* 10: 26-7 (2004); Dehm et al., *J Cell Biochem* 99: 333-344 (2006); Linja et al., *Cancer Res* 61:3550-55 (2001); Li et al., *Am J Surg Pathol* 28:928-34 (2004).) These different findings underline the heterogeneous nature of late stage, especially androgen independent, metastatic prostate cancer. (Shah et al., *Cancer Res.* 64(24):9209-16 (2004).)

To develop an in vivo readout of AR functional status in prostate cancer cells, we have been pursuing parallel quantitative measurements of various AR regulated genes in carefully isolated benign and tumor cells of over 200 specimens as shown in Example 7. Quantitative expression analyses of androgen regulated genes at the mRNA level, such as PSA/KLK3, PMEPA1, PCA3, as well as androgen independent genes (AMACR, LTF), representing over 2000 data points, suggest that PSA/KLK3 and other androgen regulated genes reflect in vivo functional status of the AR and that their expression levels can be used to measure positive or negative correlation with aggressiveness of prostate cancer, as defined, for example, by Gleason grade, pathological stage, and/or biochemical recurrence. Initially we chose to focus on PSA/KLK3 mRNA as it is one of the most robust direct transcriptional targets of AR and is easily detectable in prostate cancer cells. (Kim et al., *J Cell Biochem.* 93(2):233-41 (2004).)

Our most recent data show that quantitative gene expression patterns of a panel of AR regulated genes in primary prostate cancer provide prognostic fingerprints. Using high-throughput assays as well as rational candidate gene strategies, we defined a set of six androgen inducible/co-regulated genes (PSA/KLK3, PMEPA1, NKX3.1, ODC1, AMD1, and ERG). Different combinations of two or more of these six genes, or their isoforms, can be used to provide a quantitative measure of in vivo AR function in prostate cancer specimens, i.e., the androgen receptor function index, or ARF index (ARFI). Although real time, quantitative PCR (QRT-PCR) was used to measure the expression levels of these genes, other techniques known in the art, such as immunohistochemistry, can be used to detect RNA or protein levels.

The ARFI readout can be converted into a single number index representing the overall in vivo AR activity, which in turn can be incorporated into nomograms, such as the one created by Kattan et al. that demonstrated the importance of PSA, Gleason sum, extra-capsular extension, surgical margins, seminal vesicle invasion, lymph node involvement, treatment year, and adjuvant radiotherapy in predicting 10-year probability of prostate cancer recurrence after radical prostatectomy. The nomograms can be used to model time-to-event data, including prediction of prostate cancer progression, combined with established clinical and pathological characteristics that predict this endpoint. The concordance index, C, can be used to assess the improvement in model fit upon inclusion of ARFI. (Harrell et al., *JAMA* 247(18):2543-6 (1982).) Current nomogram calculators incorporate measurable patient factors in an attempt to use such factors to predict an outcome, such as PSA recurrence following surgery, to aid in treatment decision making in advance of invasive procedures.

The ARFI genes are either direct targets of AR or are tightly regulated by AR, and cover major biological functions regulated by AR in prostate cancer. The gene set includes five androgen regulated genes and ERG. Our original observations of frequent overexpression of certain isoforms of ERG in prostate cancer (Foley et al., *Endocr Relat Cancer* 11(3):477-88 (2004)), and subsequent independent study showing prevalent chromosomal rearrangements leading to the activation of ERG expression through AR-regulated TMPRSS2 gene promoter (Tomlins et al., *Science* 310(5748):644-8 (2005)), have highlighted ERG as an aberrant AR activated gene specific to prostate cancer. Therefore, the quantitative evaluation of ERG expression has been integrated in ARFI. The ERG read-out can be applied to TMPRSS2-ERG positive tumors, which account for greater than 60% of prostate cancer patients. (Id.)

It should be noted that although the following Examples use ERG1 as a model ERG isoform, ERG2, ERG3, ERG8, EPC1, ECP2, and combinations of those ERG isoforms can also be used, as may transcript products from the prostate cancer-specific promoter described in Example 5. Accordingly, any mention of "ERG" in the context of an ARFI readout includes not only ERG1, but also ERG2, ERG3, ERG8, EPC1, ECP2, and transcript products from the prostate cancer-specific promoter described herein, as well as their combinations, unless specifically indicated to the contrary by context or by an explicit exclusion of one or more of those isoforms. For example, ARFI readouts may employ an ERG gene that is not ERG1 or ERG2. Similarly, in some embodiments it may be desirable to include ERG8, EPC1, or EPC2 in the readout, but not ERG1 or ERG2.

Example 7: Co-Regulation of ARFI Genes Reflects Robust In Vivo Functional Linkage to AR Signaling We have recently completed a comprehensive gene expression analyses of microdissected prostate cancer cells and matched benign epithelial cells from radical prostatectomy specimens of 40 patients (80 GeneChips). (Petrovics et al., *Oncogene* 24:3847-52 (2005).) The GeneChip dataset was evaluated for androgen regulated gene expression. PSA/KLK3, PMEPA1, NKX3.1, ODC1 and AMD1, along with ERG (that can become androgen regulated in prostate cancer cells through fusion with a TMPRSS2 promoter in the majority of patients), were selected by their wide dynamic ranges of expression, as well as by their reported response to androgenic stimuli. (Heinlein et al., *Endocrine Rev* 25:276-308 (2004); Linja et al., *J Steroid Biochem Mol Biol* 92: 255-64 (2004); Shaffer et al., *Lancet Oncol* 4:407-14 (2003); Chen et al., *Nat Med* 10: 26-7 (2004); Dehm et al., *J Cell Biochem* 99: 333-344 (2006); Segawa et al., *Oncogene* 21(57):8749-58 (2002); Xu et al., *Int J Cancer* 92(3): 322-8 (2001).) Moreover, some of these genes (NKX3.1, ERG, PMEPA1) may be causally linked to prostate cancer development.

Figure 11:
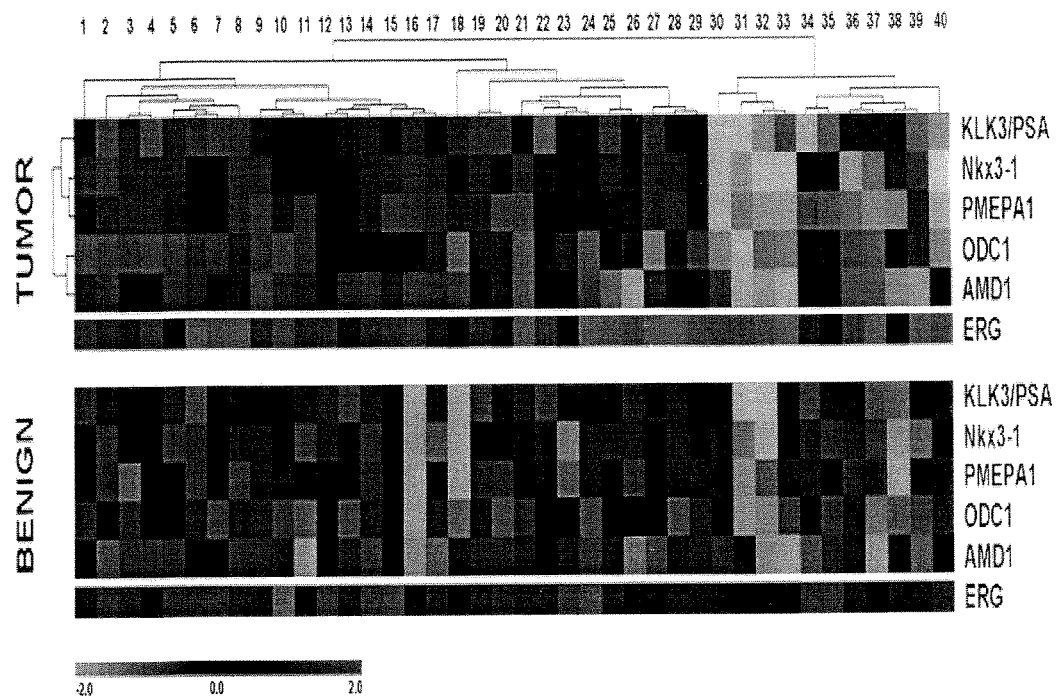
FIG. 11 compares the intensity of gene expression of the androgen regulated genes PSA/KLK3, NKX3.1, PMEPA1, ODC1, AMD1, and ERG in tumor and matched benign cells from 40 CaP patients. Z-score normalized GeneChip derived expression intensities are depicted by heat maps on a high-to-low scale after hierarchical clustering. Patient numbers (N=40) are listed above the heat map. Matched tumor and benign specimens are listed in the same order.

The concerted expression of this gene panel (ARFI) is reflective of the functional status of in vivo AR activity. Normalized expression intensity values are depicted in a heat map format (FIG. 11). A non-supervised hierarchical cluster analysis (software from TIGR, Gaithersburg, Md.) was performed both by patients and also by genes and revealed robust in vivo co-regulation of ARFI genes in the tumor cells of prostate cancer patients, reflecting either active or dysfunctional AR (FIG. 11). Two tight gene subclusters emerged: PSA/KLK3, NKX3.1, PMEPA1, and ODC1, AMD1 (polyamine pathway), differing in expression only in the middle 12-patient cluster, which underlines the importance of using a panel of ARFI genes representing different downstream AR pathways. The other two large patient clusters show tight co-regulation of all ARFI genes reflecting either active AR (left 17-patient cluster), or dysfunctional AR (right 11-patient cluster) (FIG. 11). ERG also co-regulates closely with other ARFI genes in tumor cells of the majority of prostate cancer patients, where ERG is likely fused to the androgen regulated TMPRSS2 promoter, providing a highly specific tumor cell marker.

Figure 12:
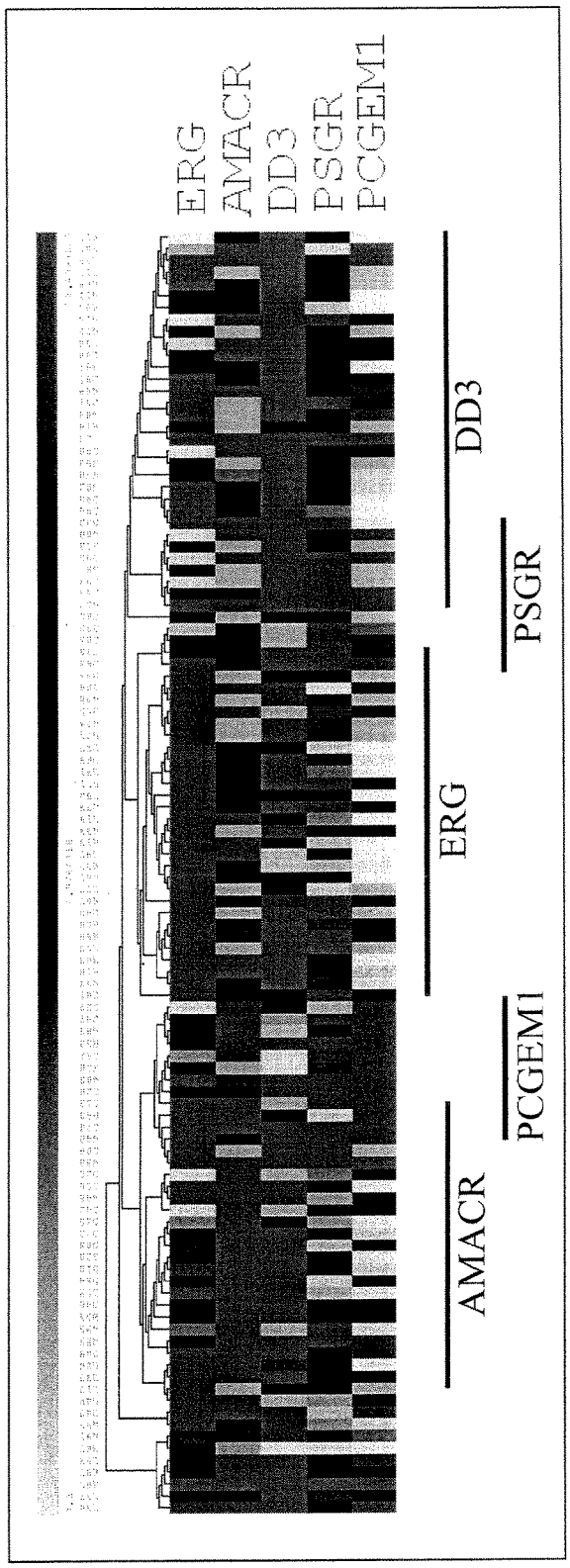
FIG. 12 shows a heat map display comparing the intensity of gene expression of the prostate cancer related genes ERG, AMACR, DD3, PSGR, and PCGEM1 in cells microdissected from prostate tissue sections.

We have also shown that ERG can be used as part of a multigene panel with other prostate cancer-associated genes that are not androgen regulated. FIG. 12 shows a heat map for a mutligene panel that includes ERG, AMACR, DD3, PSGR, and PCGEM1. The heat map is a non-supervised hierarchical clustering of tumor over normal gene expression ratios derived from TaqMan QRT-PCR analysis of microdissected cell samples from prostate tissue sections. When non-AR genes were used in the multigene panel, we found strong overexpression of the various marker genes in distinct, but overlapping subsets of patients.

Example 8: Validation of In Vivo Co-Regulation of ARFI Genes by QRT-PCR

Figure 13:
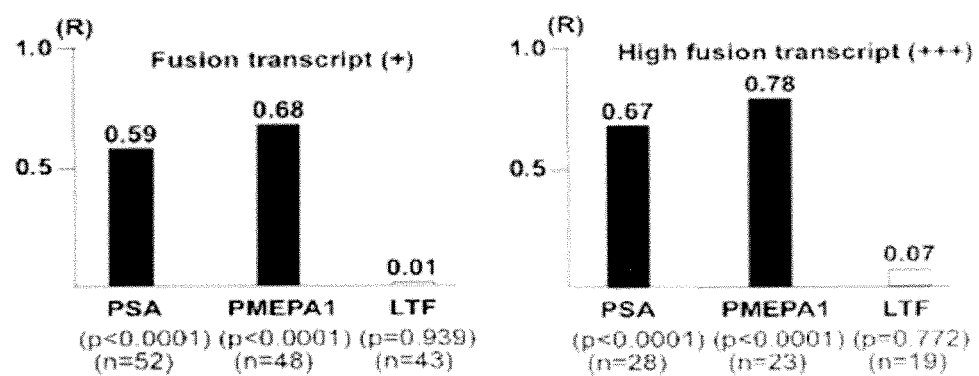
FIG. 13 shows the correlation of androgen regulated PSA/KLK3 and PMEPA1 genes with ERG expression in tumor cells of prostate cancer patients harboring TMPRSS2-ERG fusion using QRT-PCR.

Using QRT-PCR, we evaluated the expression of ERG transcripts for a relationship with the expression of the androgen-regulated genes, PSA/KLK3 and PMEPA1 (Dehm et al., *J Cell Biochem* 99: 333-344 (2006); Xu et al., *Cancer Res.* 63(15):4299-304 (2003)), in prostate cancer cells of patients with TMPRSS2-ERG fusion. LTF (Ward et al., *Cell Mol Life Sci.* 62(22):2540-8 (2005)), a non-androgen regulated control gene, was assayed in the same tumor cells (FIG. 13). In the figure, significant correlations (R>0.5) are marked by solid bars. LTF, a non-androgen regulated gene was used as a negative control. The Pearson correlation coefficient (R) is shown above the bars. P values and the number of patients (n) assessed in the experiments are indicated under the bars.

Sixty five patients with detectable TMPRSS2-ERG fusion transcript in prostate cancer cells were selected for this study. Striking co-regulation was observed between the expression levels of ERG, tissue PSA/KLK3 (p<0.0001) and PMEPA1 (p<0.0001) in patients with detectable TMPRSS2-ERG transcripts. The co-regulation is even stronger in the subset of these patients where the expression level of the TMPRSS2-ERG fusion transcript is above the median ("High fusion transcript", FIG. 13 right panel). These data indicate that the level of co-regulation within the ARFI genes (including TMPRSS2-ERG) reflects the overall functional status of AR in prostate cancer cells and that decreased expression of ARFI genes correlates with compromised or diminished androgen receptor signaling in prostate tumor cells. Furthermore, the data indicate that the expression levels of ARFI genes are reduced in advanced prostate cancer, such as pT3 stage prostate cancer.

Figure 14:
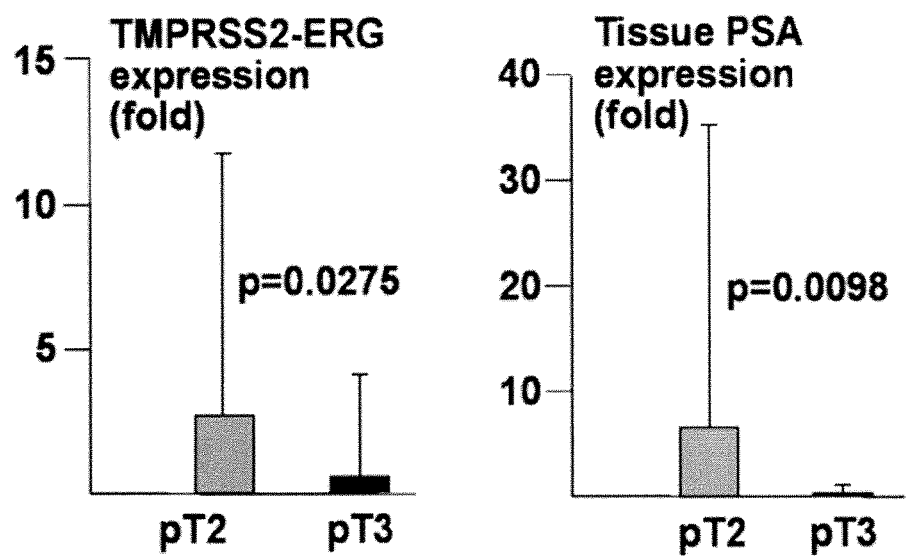
FIG. 14 demonstrates that ERG expression mirrors androgen signaling in prostate cancer tissue. TMPRSS2-ERG fusion (left panel) and PSA/KLK3 (right panel) transcript levels were compared in prostate cancer cells of pT3 and pT2 stage tumors by quantitative PCR. Y-axis scales represent fold changes of tissue expression levels relative to the expression of house keeping GAPDH gene.

Example 9: PSA/KLK3 and TMPRSS2-ERG Indicate a Decrease of In Vivo AR Activity During Prostate Cancer Progression PSA/KLK3 and ERG mRNA expression were further analyzed for their relationship to prostate cancer progression in a larger patient cohort. As shown in FIG. 14, patients with pT3 prostate cancer (locally invasive tumor growing outside the capsule) had significantly (p=0.0098) lower expression of PSA/KLK3 transcript levels as compared to patients with pT2 stage disease (organ confined). Moreover, decreased TMPRSS2-ERG fusion transcript levels were also apparent in the prostate cancer cells of pT3 patients (p=0.0275).

Figure 15:
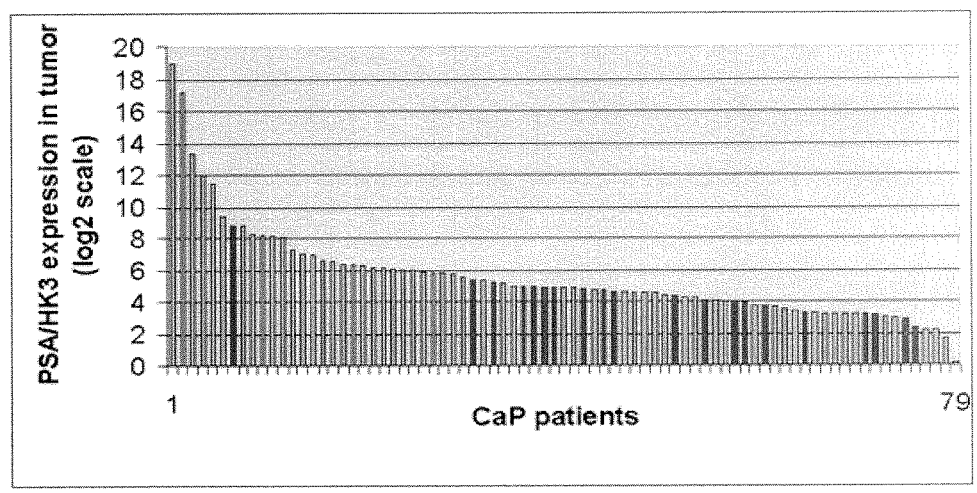
FIG. 15 shows the distribution of biochemical recurrence and tissue PSA/KLK3 mRNA expression in tumor cells of prostate cancer (CaP) patients. Relative expression of PSA/KLK3 mRNA in tumor cells, represented by vertical bars, is shown on a log 2 scale. Darkened bars indicate patients with biochemical recurrence.

To study patients with intermediate serum PSA levels, further analysis was limited to patients with serum PSA from 2 to 10 ng/mL (n=79). Based on serum PSA levels, these patients have an uncertain prognosis. FIG. 15 shows the distribution of PSA/KLK3 mRNA expression levels in tumor cells of prostate cancer patients with biochemical recurrence.

Figure 16:
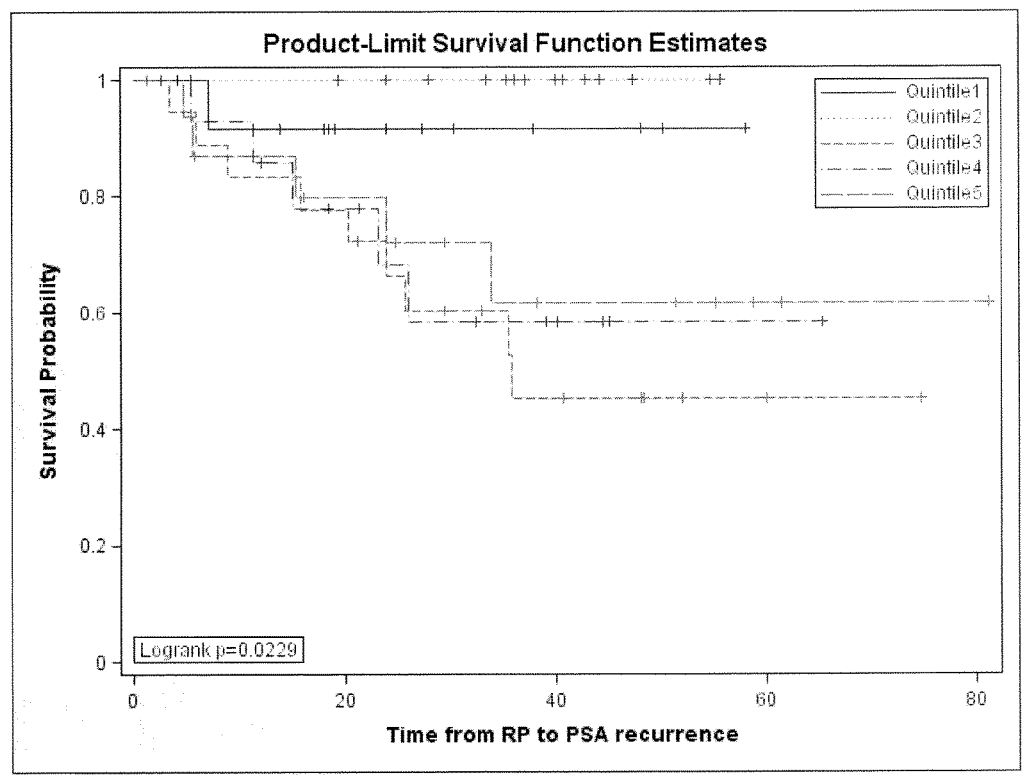
FIG. 16 shows a Kaplan-Meier survival estimation curve for time to PSA recurrence-free survival by tumor tissue PSA/KLK3 mRNA quintiles among patients with serum PSA 2-10 ng/ml. Quintiles are presented in decreasing order with quintile 1 referring to the highest and quintile 5 to the lowest PSA/KLK3 expression (N=79). Lower tissue PSA/KLK3 mRNA expression in prostate tumor cells correlates with an increased risk of biochemical recurrence.

Statistical analysis of the data presented in FIG. 15 demonstrates that the expression of tissue PSA/KLK3 mRNA in tumor cells of biochemical recurrence free patients was significantly higher than in patients with biochemical recurrence (p=0.0062, Student t-test). PSA/KLK3 mRNA expression in benign epithelial cells did not show such correlation. This prostate cancer patient cohort was divided into quintiles based on tissue PSA/KLK3 mRNA expression levels in tumor cells, and was compared with respect to time to biochemical relapse. As seen in FIG. 16, an unadjusted Kaplan-Meier analysis demonstrates improved biochemical survival for patients with the highest tissue PSA/KLK3 mRNA expression (Quintiles 1 and 2) (p=0.0229). Thus, PSA/KLK3 mRNA expression in tumor cells of prostate cancer patients inversely correlates with disease recurrence. High expression levels of tumor PSA/KLK3 mRNA correlates with biochemical recurrence free survival, whereas with low expression levels of PSA/KLK3 mRNA reflect an alteration of AR signaling in the tumor cell microenvironment, leading to an increased likelihood of tumor recurrence after prostatectomy.

The specification is most thoroughly understood in light of the teachings of the references cited within the specification which are hereby incorporated by reference. The embodiments within the specification provide an illustration of embodiments of the invention and should not be construed to limit the scope of the invention. The skilled artisan readily recognizes that many other embodiments are encompassed by the invention.

What is claimed is:

1. A method of detecting the expression of Ets Related Gene 8 (ERG8) mRNA in a biological sample comprising nucleic acid isolated from human prostate epithelial cells, the method comprising:
    (a) combining the nucleic acid sample isolated from human prostate epithelial cells with at least a first and a second oligonucleotide primer under hybridizing conditions, wherein the entire nucleotide sequence of at least one of the first or the second oligonucleotide primers hybridizes to a region within nucleotides 803 to 1168 of SEQ ID NO: 1 or a nucleic acid strand complementary to said region;
    (b) amplifying a plurality of amplification products when said nucleotides 803 to 1168 of SEQ ID NO: 1 are present in the nucleic acid sample by adding at least one polymerase activity to the biological sample containing the first and second oligonucleotide primers, wherein the amplification products comprises the region within nucleotides 803 to 1168 of SEQ ID NO: 1 to which the entire nucleotide sequence of at least one of the first or the second oligonucleotide primers hybridizes;
    (c) immobilizing the plurality of amplification products;
    (d) combining an oligonucleotide probe with the immobilized plurality of amplification products to thereby permit the probe to hybridize to at least one immobilized amplification product;
    (e) detecting whether a signal results from hybridization between the oligonucleotide probe and at least one amplification product, and
    (f) detecting expression of ERG8 mRNA in the biological sample if the signal is detected in step (e), wherein the biological sample is obtained from a subject suspected of having prostate cancer.

2. The method of claim 1, wherein the entire sequence of the first oligonucleotide primer hybridizes to a first region within said nucleotides 803 to 1168 of SEQ ID NO:1 and the entire sequence of the second oligonucleotide primer hybridizes to a nucleic acid strand complementary to a second region within said nucleotides 803 to 1168 of SEQ ID NO:1.

3. A method of detecting the expression of Ets Related Gene 8 (ERG8) mRNA in a biological sample comprising nucleic acid isolated from human prostate epithelial cells, the method comprising:
    (a) combining the nucleic acid isolated from human prostate epithelial cells with at least a first and a second oligonucleotide primer under hybridizing conditions;
    (b) amplifying a plurality of amplification products when a ERG8 target sequence is present in the nucleic acid sample by adding at least one polymerase activity to the biological sample containing the first and second oligonucleotide primers, wherein the ERG8 target sequence consists of nucleotides 803 to 1168 of SEQ ID NO: 1;
    (c) detecting the plurality of amplification products; and
    (d) detecting expression of ERG8 mRNA in the biological sample if the plurality of amplification products is detected in step (c), wherein the biological sample is obtained from a subject suspected of having prostate cancer.

4. The method of claim 3, wherein detecting the plurality of amplification products comprises:
    (a) immobilizing the plurality of amplification products;
    (b) combining an oligonucleotide probe with the immobilized plurality of amplification products to thereby permit the probe to hybridize to at least one immobilized amplification product; and
    (c) detecting whether a signal results from hybridization between the oligonucleotide probe and at least one amplification product.

5. The method of claim 3, wherein the first oligonucleotide primer contains a sequence that hybridizes to either a first sequence in the target sequence or a second sequence in a nucleic acid strand complementary to the target sequence.

6. The method of claim 5, wherein the first oligonucleotide primer contains a sequence that hybridizes to the first sequence in the target sequence and the second oligonucleotide primer contains a sequence that hybridizes to a second sequence in a nucleic acid strand complementary to the target sequence, wherein the first sequence does not overlap with the second sequence.

* * * * *